(12) United States Patent
Zheng et al.

(10) Patent No.: US 9,643,184 B2
(45) Date of Patent: May 9, 2017

(54) E-PETRI DISHES, DEVICES, AND SYSTEMS HAVING A LIGHT DETECTOR FOR SAMPLING A SEQUENCE OF SUB-PIXEL SHIFTED PROJECTION IMAGES

(75) Inventors: Guoan Zheng, Pasadena, CA (US);
Samuel Yang, San Dimas, CA (US);
Seung Ah Lee, Pasadena, CA (US);
Shuo Pang, Pasadena, CA (US);
Changhuei Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 827 days.

(21) Appl. No.: 13/411,302

(22) Filed: Mar. 2, 2012

(65) Prior Publication Data

US 2012/0223217 A1 Sep. 6, 2012

Related U.S. Application Data

(63) Continuation-in-part of application No. 13/281,287, filed on Oct. 25, 2011, now Pat. No. 9,426,429.

(60) Provisional application No. 61/406,916, filed on Oct. 26, 2010, provisional application No. 61/482,531, (Continued)

(51) Int. Cl.
| | | |
|---|---|---|
| *B01L 3/00* | (2006.01) | |
| *C12M 1/22* | (2006.01) | |
| *G01N 21/03* | (2006.01) | |
| *G01N 21/25* | (2006.01) | |
| *G01N 21/27* | (2006.01) | |

(52) U.S. Cl.
CPC ............. *B01L 3/508* (2013.01); *C12M 23/10* (2013.01); *G01N 21/03* (2013.01); *G01N 21/25* (2013.01); *G01N 21/272* (2013.01); *B01L 3/502792* (2013.01); *B01L 2300/0654* (2013.01); *G01N 2201/10* (2013.01)

(58) Field of Classification Search
CPC ................................ G02B 21/06; B01L 3/508
USPC ............................................. 348/79; 250/215
See application file for complete search history.

(56) References Cited

U.S. PATENT DOCUMENTS

| | | | |
|---|---|---|---|
| 3,736,432 A | 5/1973 | Sweet | |
| 5,225,057 A | 7/1993 | LeFebvre et al. | |
| 5,349,191 A | 9/1994 | Rogers | |

(Continued)

FOREIGN PATENT DOCUMENTS

| | | |
|---|---|---|
| CN | 1588163 A | 3/2005 |
| CN | 101655463 A | 2/2010 |

(Continued)

OTHER PUBLICATIONS

Cui et al. Lensless high-resolution on-chip optofluidic microscopes for canenorhabdits elegans and cell imaging, May 13, 2008, pp. 10670-10675.*

(Continued)

*Primary Examiner* — Jay Patel
*Assistant Examiner* — Irfan Habib
(74) *Attorney, Agent, or Firm* — Sheila Martinez-Lemke; Weaver Austin Villeneuve & Sampson LLP

(57) ABSTRACT

An e-Petri dish comprising a transparent layer having a specimen surface and a light detector configured to sample a sequence of sub-pixel shifted projection images of a specimen located on the specimen surface. The sub-pixel shifted projection images associated with light from a plurality of illumination angles provided by an illumination source.

40 Claims, 17 Drawing Sheets

Related U.S. Application Data filed on May 4, 2011, provisional application No. 61/448,964, filed on Mar. 3, 2011.

(56) References Cited

U.S. PATENT DOCUMENTS

| | | | |
|---|---|---|---|
| 5,420,959 A | 5/1995 | Walker et al. | |
| 5,495,337 A | 2/1996 | Goshorn et al. | |
| 5,545,561 A | 8/1996 | Lleonart Aliberas | |
| 5,684,906 A | 11/1997 | Sugawara | |
| 5,796,112 A | 8/1998 | Ichie | |
| 5,892,577 A | 4/1999 | Gordon | |
| 6,058,209 A | 5/2000 | Vaidyanathan et al. | |
| 6,147,798 A | 11/2000 | Brooker et al. | |
| 6,194,718 B1 * | 2/2001 | Dotan | H01J 37/222 250/307 |
| 6,215,114 B1 | 4/2001 | Yagi et al. | |
| 6,519,313 B2 | 2/2003 | Venkataramani et al. | |
| 6,555,816 B1 | 4/2003 | Sawahata et al. | |
| 6,608,717 B1 | 8/2003 | Medford et al. | |
| 6,717,726 B2 | 4/2004 | Boehm et al. | |
| 6,784,417 B2 | 8/2004 | Sonoki | |
| 6,903,820 B2 | 6/2005 | Wang | |
| 6,937,323 B2 | 8/2005 | Worthington et al. | |
| 6,944,322 B2 | 9/2005 | Johnson et al. | |
| 7,005,654 B2 | 2/2006 | Seyfried | |
| 7,133,130 B2 | 11/2006 | Storz et al. | |
| 7,142,296 B2 | 11/2006 | Cunningham et al. | |
| 7,250,598 B2 | 7/2007 | Hollingsworth et al. | |
| 7,253,947 B2 * | 8/2007 | Bromage | G02B 21/008 248/432 |
| 7,323,681 B1 | 1/2008 | Oldham et al. | |
| 7,369,234 B2 | 5/2008 | Beaglehole | |
| 7,418,118 B2 * | 8/2008 | Furnas | G02B 21/365 382/128 |
| 7,705,331 B1 | 4/2010 | Kirk et al. | |
| 7,892,168 B2 | 2/2011 | Sano | |
| 7,986,824 B2 | 7/2011 | Suzuki et al. | |
| 8,139,106 B2 | 3/2012 | Maiya | |
| 8,337,786 B2 * | 12/2012 | McLellan et al. | B01L 3/508 422/547 |
| 8,345,351 B2 * | 1/2013 | Takeuchi | G02B 21/0008 359/363 |
| 8,355,133 B2 * | 1/2013 | Dultz | G01N 21/253 356/445 |
| 8,490,469 B2 | 7/2013 | Superfine et al. | |
| 8,498,681 B2 | 7/2013 | Wang et al. | |
| 8,501,435 B2 | 8/2013 | Gustafsson et al. | |
| 8,526,006 B2 | 9/2013 | Nebosis et al. | |
| 8,624,968 B1 * | 1/2014 | Hersee | B82Y 15/00 348/79 |
| 8,730,574 B2 | 5/2014 | Araya et al. | |
| 8,837,045 B2 | 9/2014 | Popescu et al. | |
| 8,866,063 B2 * | 10/2014 | Ozcan | G02B 21/00 250/216 |
| 8,928,890 B2 | 1/2015 | Nebosis et al. | |
| 8,964,017 B2 | 2/2015 | Vertikov et al. | |
| 8,993,961 B2 | 3/2015 | Tsuneta et al. | |
| 9,105,102 B1 | 8/2015 | Walther et al. | |
| 9,280,707 B2 | 3/2016 | Ishihara | |
| 9,291,998 B2 * | 3/2016 | Huys | G03H 1/0402 |
| 9,333,503 B2 * | 5/2016 | Zantl | B01L 3/508 |
| 9,343,494 B2 * | 5/2016 | Lee | H01L 27/14621 |
| 9,426,429 B2 | 8/2016 | Zheng et al. | |
| 9,569,664 B2 | 2/2017 | Judkewitz et al. | |
| 2002/0070350 A1 | 6/2002 | Rushbrooke et al. | |
| 2002/0080240 A1 * | 6/2002 | Omi | G02B 21/365 348/207.99 |
| 2003/0012277 A1 | 1/2003 | Azuma et al. | |
| 2003/0032039 A1 | 2/2003 | Cunningham et al. | |
| 2004/0135079 A1 | 7/2004 | Moellmann | |
| 2004/0146965 A1 | 7/2004 | Brayton | |
| 2004/0264637 A1 * | 12/2004 | Wang | G21K 7/00 378/43 |
| 2005/0013478 A1 | 1/2005 | Oba et al. | |
| 2005/0078362 A1 | 4/2005 | Borlinghaus | |
| 2006/0007436 A1 * | 1/2006 | Kurosawa | G01N 21/47 356/237.4 |
| 2006/0077535 A1 | 4/2006 | Luther et al. | |
| 2006/0092503 A1 * | 5/2006 | Saunders | G02B 21/0008 359/368 |
| 2006/0124870 A1 | 6/2006 | Bobanovic et al. | |
| 2006/0227328 A1 | 10/2006 | Vanwiggeren et al. | |
| 2007/0046924 A1 | 3/2007 | Chang | |
| 2007/0052953 A1 | 3/2007 | Hill | |
| 2007/0058054 A1 | 3/2007 | Kagayama et al. | |
| 2007/0081200 A1 | 4/2007 | Zomet et al. | |
| 2007/0207061 A1 | 9/2007 | Yang et al. | |
| 2007/0229852 A1 | 10/2007 | Wack et al. | |
| 2007/0236782 A1 | 10/2007 | Sano | |
| 2008/0056610 A1 | 3/2008 | Kanda | |
| 2008/0144029 A1 | 6/2008 | Li | |
| 2008/0158566 A1 | 7/2008 | Suzuki et al. | |
| 2008/0174862 A1 | 7/2008 | Focht | |
| 2008/0204551 A1 * | 8/2008 | O'Connell | G02B 21/0008 348/79 |
| 2008/0213141 A1 | 9/2008 | Pinchot | |
| 2008/0214412 A1 | 9/2008 | Stahler et al. | |
| 2008/0259345 A1 | 10/2008 | Fukutake | |
| 2009/0086314 A1 | 4/2009 | Namba et al. | |
| 2009/0091811 A1 | 4/2009 | Asundi et al. | |
| 2009/0122070 A1 | 5/2009 | Aragaki et al. | |
| 2009/0166518 A1 | 7/2009 | Tay et al. | |
| 2009/0180179 A1 * | 7/2009 | Ryu | G02B 21/367 359/383 |
| 2009/0225309 A1 | 9/2009 | Demou | |
| 2009/0225319 A1 | 9/2009 | Lee et al. | |
| 2009/0237502 A1 | 9/2009 | Maiya | |
| 2009/0268280 A1 | 10/2009 | Osawa et al. | |
| 2009/0273829 A1 | 11/2009 | Terakawa et al. | |
| 2009/0276188 A1 | 11/2009 | Cui et al. | |
| 2010/0033561 A1 | 2/2010 | Hersee | |
| 2010/0045955 A1 | 2/2010 | Vladimirsky et al. | |
| 2010/0108873 A1 * | 5/2010 | Schwertner | G01B 11/2504 250/252.1 |
| 2010/0308427 A1 | 12/2010 | Lenchenkov | |
| 2011/0001815 A1 | 1/2011 | Nakano et al. | |
| 2011/0063592 A1 | 3/2011 | Ezura et al. | |
| 2011/0069382 A1 | 3/2011 | Toomre et al. | |
| 2011/0098950 A1 | 4/2011 | Carr | |
| 2011/0102888 A1 | 5/2011 | Honda et al. | |
| 2011/0234757 A1 | 9/2011 | Zheng et al. | |
| 2011/0266181 A1 * | 11/2011 | Morozov | B01L 3/508 206/456 |
| 2012/0086995 A1 | 4/2012 | Gerchberg et al. | |
| 2012/0098950 A1 | 4/2012 | Zheng et al. | |
| 2012/0099803 A1 | 4/2012 | Ozcan et al. | |
| 2012/0157160 A1 | 6/2012 | Ozcan et al. | |
| 2012/0218379 A1 | 8/2012 | Ozcan et al. | |
| 2012/0223214 A1 | 9/2012 | Lee et al. | |
| 2012/0228475 A1 | 9/2012 | Pang et al. | |
| 2012/0248292 A1 | 10/2012 | Ozcan et al. | |
| 2012/0258525 A1 | 10/2012 | Iizumi et al. | |
| 2012/0275681 A1 | 11/2012 | Honda et al. | |
| 2014/0133702 A1 | 5/2014 | Zheng et al. | |

FOREIGN PATENT DOCUMENTS

| | | |
|---|---|---|
| DE | 202 14 835 U1 | 1/2003 |
| EP | 1 956 360 | 8/2008 |
| FR | 2 602 241 | 2/1988 |
| JP | 2010-020151 A | 1/2010 |
| JP | 2013-542468 A | 11/2013 |
| JP | 2014-515179 A | 6/2014 |
| WO | WO 91/09300 | 6/1991 |
| WO | WO 2009/113544 | 9/2009 |
| WO | WO 2010/141702 | 12/2010 |
| WO | WO 2011/119678 | 9/2011 |
| WO | WO 2011/139641 | 11/2011 |
| WO | WO 2012/058233 | 5/2012 |

(56) References Cited

FOREIGN PATENT DOCUMENTS

| WO | WO 2012/094523 | 7/2012 |
|---|---|---|
| WO | WO 2012/119094 | 9/2012 |
| WO | WO 2012/119114 | 9/2012 |

OTHER PUBLICATIONS

United States Patent and Trademark Office (USPTO) Non-Final Office Action in U.S. Appl. No. 13/069,651 dated on Mar. 28, 2014.
United States Patent and Trademark Office (USPTO) Final Office Action in U.S. Appl. No. 13/069,651 dated on Nov. 25, 2014.
United States Patent and Trademark Office (USPTO) Non-Final Office Action in U.S. Appl. No. 13/281,287 dated on Oct. 31, 2013.
United States Patent and Trademark Office (USPTO) Final Office Action in U.S. Appl. No. 13/281,287 dated on Mar. 12, 2014.
United States Patent and Trademark Office (USPTO) Office Action in U.S. Appl. No. 13/281,287 dated on Nov. 6, 2014.
United States Patent and Trademark Office (USPTO) Office Action in U.S. Appl. No. 14/072,652 dated on Mar. 23, 2015.
United States Patent and Trademark Office (USPTO) Non-Final Office Action in U.S. Appl. No. 13/411,103 dated on Mar. 11, 2014.
United States Patent and Trademark Office (USPTO) Final Office Action in U.S. Appl. No. 13/411,103 dated on Oct. 2, 2014.
PCT International Search Report dated Dec. 7, 2011 issued in PCT/US2011/029542.
PCT International Preliminary Report on Patentability and Written Opinion dated Oct. 4, 2012 issued in PCT/US2011/029542.
Chinese First Office Action dated Jan. 23, 2014 issued in CN 201180012251.6.
Chinese Second Office Action dated Oct. 8, 2014 issued in CN 201180012251.6.
Chinese Third Office Action dated Apr. 27, 2015 issued in CN 201180012251.6.
European Search Report dated Jun. 25, 2014 issued in EP 11 760 112.0.
PCT International Search Report dated May 8, 2012 issued in PCT/US2011/057735.
PCT International Preliminary Report on Patentability and Written Opinion dated May 10, 2013 issued in PCT/US2011/057735.
Chinese First Office Action [no translation] dated Jan. 20, 2015 issued in CN 201180048639.1.
European Search Report dated Jun. 25, 2014 issued in EP 11 836 959.
European Office Action dated Jul. 3, 2014 issued in EP 11 836 959.4.
Japanese Office Action [with translation] dated Oct. 28, 2014 issued in JP 2013536747.
PCT International Search Report and Written Opinion dated Sep. 25, 2012 issued in PCT/US2012/027575.
PCT International Preliminary Report on Patentability and Written Opinion dated Sep. 12, 2013 issued in PCT/US2012/027575.
Chinese First Office Action dated Feb. 28, 2015 issued in CN201280003668.
European Search Report dated Jun. 25, 2014 issued in EP 12 75 2493.
PCT International Search Report and Written Opinion dated Sep. 21, 2012 issued in PCT/US2012/027522.
PCT International Preliminary Report on Patentability and Written Opinion dated Sep. 12, 2013 issued in PCT/US2012/027522.
European Supplementary Search Report dated Jun. 25, 2014 issued in EP 12 75 2808.
Bishara et al., (May 24, 2010) "Lensfree on-chip microscopy over a wide field-of-view using pixel super-resolution," opticsinfobase. org, *Opt. Expr.* 18(11):11181-11191.
Cui, Xiquan, et al., (Aug. 5, 2008) "Lensless high-resolution on-chip optofluidic microscopes for *Caenorhabditis elegans* and cell imaging," *Proceedings of the National Academy of Sciences of the United States of America*, 105(31):10670-10675.
Elad, M., and Hel-Or, Y., (Dec. 1998) "A Fast Super-Resolution Reconstruction Algorithm for Pure Translational Motion and Common Space—Invariant Blur," *IEEE Transactions on Image Processing*, 10:1187-1193.
Farsiu, S. et al., (Jan. 2004) "Advances and challenges in super-resolution," *Wiley Periodicals*, 14:47-57.
Farsiu, S., et al., (Oct. 2004) "Fast and robust multiframe super resolution," *IEEE Transactions on Image Processing*, 13(10):1327-1344.
Gillette, J., et al., (1995) "Aliasing reduction in staring infrared imagers utilizing subpixel techniques," *Optical Engineering*, 34:3130.
Hardie Russell C., et al., (Apr. 1997) "High resolution image reconstruction from a sequence of rotated and translated frames and its application to an infrared imaging system," *Optical Engineering*, 27 pp.
Heng, Xin, et al., (2006) "Characterization of light collection through a subwavelength aperture from a point source," *Optics Express*, 14:10410-10425.
Heng, Xin, et al., (Jul. 17, 2006) "Optofluidic Microscopy: A Novel High Resolution Microscope-on-a-Chip," *Leos Summer Topical Meetings, 2006 Digest of the Quebec City, QC, Canada Jul. 17-19 2006, Piscataway, NJ, USA, IEEE*, 6(10):15-16.
Kapur, J., et al., (1985) "A New Method for Gray-Level Picture Thresholding Using the Entropy of the Histogram," *Computer vision, graphics, and image processing*, 29:273-285.
Lee, Seung Ah, et al., (Oct. 2011) "Color Capable Sub-Pixel Resolving Optofluidic Microscope and Its Application to Blood Cell Imaging for Malaria Diagnosis," *PLoS One* 6(10):e26127, 6 pages.
Lee, Seung, Ah, et al., (Mar. 20, 2012) "On-chip continuous monitoring of motile microorganisms on an ePetri platform," *Lab on a Chip* 12(13):2385-2390.
Levin-Reisman, I., et al., (2010) "Automated imaging with ScanLag reveals previously undetectable bacterial growth phenotypes," *Nat Meth*, 7(9):737-739.
Liang, J. Z., et al., (Nov. 1997) "Supernormal vision and high-resolution retinal imaging through adaptive optics," *Journal of the Optical Society of America*, 14(11):2884-2892.
Lin, Z., and Shum, H.-Y., (2004) "Fundamental limits of reconstruction-based superresolution algorithms under local translation," *IEEE Transactions on Pattern Analysis and Machine Intelligence*, pp. 83-97.
Miao, Qin, et al., (2009) "Dual Modal three-dimensional Imaging of Single Cells using Optical Projection Tomography Microscope," *Journal of Biomedical Optics*, 14:3 pages.
Moon, SanJun, et al., (Jul. 15, 2009) "Integrating Microfluidics and Lensless Imaging for point-of-care testing," *Biosensors and Bioelectronics*, 24(11):3208-3214.
Park, Sung Cheol, et al., (2003) "Super-resolution image reconstruction: a technical overview," *IEEE Signal Processing Magazine*, pp. 21-36.
Pastrana, Erika (Dec. 2011) *Nature Methods*, 8(12):999, 1 page [doi:10.1038/nmeth.1786].
Psaltis, Demetri, et al., (Jul. 2006) "Developing optofluidic technology through the fusion of microfluidics and optics," *Nature*, 442:381-386.
Schultz, R., et al., (1998) "Subpixel Motion Estimation for Super-Resolution Image Sequence Enhancement," *Journal of Visual Communication and Image Representation*, 9(1):38-50.
Shi, J., et al., (2006) "Small-kernel superresolution methods for microscanning imaging systems," *Applied Optics*, 45(6):1203-1214.
Su, Ting-Wei, et al., (Apr. 26, 2010) "Multi-angle lensless digital holography for depth resolved imaging on a chip," *Optics Express*, OSA, Washington DC, US 18(9):9670-9711, 22pp.
Tai, Y. C., et al., (2002) "Integrated micro/nano fluidics for mass-spectrometry protein analysis," *International Journal of Nonlinear Sciences and Numerical Simulation*, 3(3-4):739-741.
Wang et al., (2009) "Characterization of acceptance angles of small circular apertures," *Optics Express* 17(26):23903-23913.
Wu, J., et al., (Jul. 1, 2010) "Wide field-of-view microscope based on holographic focus grid illumination," *Optics Letters*, 35(13):2188-2190.

(56) References Cited

OTHER PUBLICATIONS

Yanowitz, et al., (2005) "Cyclin D involvement demarcates a late transition in *C. elegans* embryogenesis," *Developmental Biology*, 279:244-251.
Zheng, et al., (2010) "Sub-pixel resolving optofluidic microscope for on-chip cell imaging," *Lab on a Chip*, 10(2):3125-3129.
Zheng, et al., (2009) "Supplementary Information for: Sub-pixel resolving optofluidic microscope for on-chip cell imaging," *Supplementary Material (ESI) for Lap on a Chip*, 10:3 pages.
Zheng, et al., (Oct. 15, 2011) "Microscopy refocusing and dark-field imaging by using a simple LED array," *Optics Letters* 36(20):3987-3989.
Zheng et al., (2011) "The ePetri dish, an on-chip cell imaging platform based on subpixel perspective sweeping microscopy (SPSM)," 6 pages and "Supporting Information" 3 pages; *Proceedings of the National Academy of Science* 108(41):16889-94.
Zheng et al., (Jul. 28, 2013) "Wide-field, high-resolution Fourier ptychographic microscopy," *Nature Photonics | Advance Online Publication*, DOI: 10.1038/NPHOTON.2013.187, 19 pages.
United States Patent and Trademark Office (USPTO) Non-Final Office Action in U.S. Appl. No. 13/069,651 dated on Jul. 15, 2015.
United States Patent and Trademark Office (USPTO) Final Office Action in U.S. Appl. No. 13/281,287 dated on Jul. 1, 2015.
United States Patent and Trademark Office (USPTO) Office Action in U.S. Appl. No. 13/411,103 dated on Jun. 17, 2015.
European Examination Report dated Jun. 5, 2015 issued in EP 11 760 112.0.
European Office Action dated Jun. 5, 2015 issued in EP 11 836 959.4.
Japanese Office Action [with translation] dated Jun. 23, 2015 issued in JP 2013-536747.
European Examination Report dated Jun. 5, 2015 issued in EP 12 75 2493.
"Fresnel number," Wikipedia, last modified May 2, 2010, 2pp.
Confocal Raman Microscopy (Oct. 2006) "Optofluidic Microscope Enables Lensless Imaging of Microorganisms," *Biophotonics International*, 13(10):24.
"Zone plate," Wikipedia, last modified Apr. 2, 2009.
Aigouy, L., et al., (2007) "Near-field analysis of surface waves launched at nanoslit apertures," *Physical Review Letters*, 98:153902.
Biener, G., et al., (2011)"Combined reflection and transmission microscope for telemedicine applications infield settings, "*Lab Chip*, 11(16):2738-2743.
Blanco et al. (2006) "Microfluidic-optical integrated CMOS compatible devices for label-free biochemical sensing," *J. Micromech. Microeng.* 16:1006-1016.
Borenfreund, E. & Puerner, J. A., (1985) "Toxicity determined in vitro by morphological alterations and neutral red absorption, "*Toxicology Letters* 24:119-124.
Breslauer, D., et al., (Jul. 2009) "Mobile Phone Based Clinical Microscopy for Global Health Applications," *PLoS ONE*, 4(7):e6320, 7pp.
Cavanaugh, P.F. et al., (1990) "A semi-automated neutral red based chemosensitivity assay for drug screening, " *Investigational new drugs*, 8:347-354.
Cohen, A.R., Gomes, F. L.A.F., Roysam, B.& Cayouette, M., (Mar. 2010) "Computational prediction of neural progenitor cell fates," *Nature Methods*, 7(3):213, 10pp.
Costa, M. R. et al., (2011) "Continuous live imaging of adult neural stem cell division and lineage progression in vitro," *Development*, 138(6):1057-1068.
Crane, M., Chung, K., Stirman, J. & Lu, H., (2010) "Microfluidics-enabled phenotyping, imaging, and screening of multicellular organisms," *Lab on a Chip*, 10:1509-1517.
Denis, L., Lorenz, D., Thiébaut, E., Fournier, C., Trede, D., (2009) "Inline hologram reconstruction with sparsity constraints," *Opt Lett*, 34:3475-3477.
Dykstra, B. et al., (May 23, 2006) "High-resolution video monitoring of hematopoietic stem cells cultured in single-cell arrays identifies new features of self-renewal," *PNAS*, 103(21):8185-8190.
Eilken, H.M., Nishikawa, S.I. & Schroeder, T. (Feb. 2009) "Continuous single-cell imaging of blood generation from haemogenic endothelium," *Nature*, 457:896-900.
Farsiu S. et al., (Jan. 2006) "Multiframe Demosaicing and Super-Resolution of Color Images," *IEEE Transactions on Image Processing*, 15(1):141-159.
Farsiu, S., Robinson, D., Elad, M. & Milanfar, P., (2004) "Advances and Challenges in Super Resolution," *International Journal of Imaging Systems and Technology*, 14:47-57.
Fienup, J.R., (Jul. 1978) "Reconstruction of an object from the modulus of its Fourier transform, " *Opt Lett*, 3(1):27-29.
Garcia-Sucerquia, J., et al., (Feb. 2006) "Digital in-line holographic microscopy," *Appl. Opt.*, 45(5):836-850.
Hardie, R., Barnard, K., and Armsrong, E.E., (Dec. 1997) "Joint MAP Registration and High-Resolution Image Estimation Using a Sequence of Undersampled Images," *IEEE Transactions on Image Processing*, 6(12):1621-1633.
Heng, Xin, et al., (2006) "Optofluidic Microscopy—a method for implementing a high resolution optical microscope on a chip," *Lab Chip*, 6(10):1274-1276.
Hou, H., et al., (2010) "Deformability based cell margination—A simple microfluidic design for malaria infected erythrocyte separation," *Lab on a Chip* 10:2605-2613.
Isikman, S.O., et al., (May 3, 2011) "Lens-free optical tomographic microscope with a large imaging volume on a chip, " *PNAS USA*, 108(18):7296-7301.
Koren, G., Polack, F., Joyeux, D., (Mar. 1993) Iterative algorithms for twin-image elimination in in-line holography using finite-support constraints, *J Opt Soc Am A* 10:423-433.
Lai, S., King, B., Neifeld, M.A., (2000) "Wave front reconstruction by means of phase-shifting digital in-line holography, " *Opt Commun.*, 173:155-160.
Lange et al., (2005) "A microfluidic shadow imaging system for the study of the nematode *Caenorhabditis elegans* in space," *Sensors and Actuators B*, 107:904-914.
Li, W., Knoll, T., Thielecke, H., (2010) "On-chip integrated lensless microscopy module for optical monitoring of adherent growing mammalian cells," *Engineering in Medicine and Biology Society (EMBC)*, *2010 32nd Annual International Conference of the IEEE*, pp. 1012-1015.
Liu, G. and Scott, P., (Jan. 1987) "Phase retrieval and twin-image elimination for in-line Fresnel holograms," *J Opt Soc Am A*, 4(1):159-165.
Malek M., Aliano, D., Coëtmellec, S., Lebrun, D., (May 17, 2004) "Digital in-line holography: Influence of the shadow density on particle field extraction," *Opt. Express*, 12(10):2270-2279.
Medoro, G. et al. (2003) "A Lab-on-a-Chip for Cell Detection and Illumination," *IEEE Sensors Journal*, 3(3):317-325.
Miao, Q., Rahn, J.R., Tourovskaia, A., Meyer, M.G., Neumann, T., Nelson, A.C., and Seibel, E.J., (Dec. 21, 2009) "Dual-modal three dimensional imaging of single cells with isometric high resolution using an optical projection tomography microscope," *J. Biomed. Opt.*, 14(6):064034, 6pp.
Micó, V., Garcia, J., Zalevsky, Z., and Javidi, B., (Oct. 2010) "Phase-Shifting Gabor Holographic Microscopy, " *J Disp Technol*, 6(10):484-489.
Milanfar, P., (2010) "Super-Resolution Imaging," *CRC Press*, 9pp.
Mudanyali, O., et al., (Jun. 7, 2010) "Compact, light-weight and cost-effective Microscope based on Lensless Incoherent Holography for Telemedicine Applications," *Lab on a Chip*, 10:1417-1428, 25 pp.
Repetto, G., Del Peso, A. & Zurita, J.L., (2008) "Neutral red uptake assay for the estimation of cell viability/cytotoxicity," *Nature Protocols* 3(7):1125-1131.
Rodenburg, J.M., Hurst, A.C., Cullis, A.G., (2007) "Transmission microscopy without lenses for objects of unlimited size, " *Ultramicroscopy*, 107:227-231.
Schroeder, T., (2011) "Long-term single-cell imaging of mammalian stem cells," *Nature Methods Supplement*, 8(4):S30-S35.

(56) References Cited

OTHER PUBLICATIONS

Schultz, R.R., Meng, L., Stevenson, R.L., (1998) "Subpixel motion estimation for superresolution image sequence enhancement," *Journal of Visual Communication and Image Representation*, 9(1):38-50.

Seo, et al., (2009) "Lensfree holographic imaging for on-chip cytometry and diagnostics," *Lab on a Chip*, 9(6):777-787.

Xu, et al. (2001) "Digital in-line holography for biological applications," *PNAS* USA, 98:11301-11305.

Xu, L., Miao, J., Asundi, A., (Dec. 2000) "Properties of digital holography based on in-line configuration," *Opt Eng*, 39(12):3214-3219.

Zhang, F., Pedrini, G., and Osten, W., (2007) "Phase retrieval of arbitrary complex-valued fields through apertureplane modulation," *Phys Rev A*, 75:043805, 4pp.

United States Patent and Trademark Office (USPTO) Final Office Action in U.S. Appl. No. 13/069,651 dated on Mar. 3, 2016.

United States Patent and Trademark Office (USPTO) Final Office Action in U.S. Appl. No. 14/072,652 dated on Nov. 6, 2015.

United States Patent and Trademark Office (USPTO) Notice of Allowance in U.S. Appl. No. 13/411,103 dated on Jan. 4, 2016.

European Examination Report dated Feb. 2, 2016 issued in EP 12 75 2493.

Japanese Office Action dated Oct. 6, 2015 issued in JP 2013-556657.

United States Patent and Trademark Office (USPTO) Notice of Allowance in U.S. Appl. No. 13/281,287 dated on May 25, 2016.

Chinese Office Action [no translation] dated Nov. 3, 2014 issued in CN 201280011370.4.

United States Patent and Trademark Office (USPTO) Notice of Allowance in U.S. Appl. No. 13/069,651 dated on Oct. 12, 2016.

United States Patent and Trademark Office (USPTO) Notice of Allowance in U.S. Appl. No. 14/072,652 dated on Oct. 24, 2016.

United States Patent and Trademark Office (USPTO) Notice of Allowance in U.S. Appl. No. 14/072,652 dated on Jan. 12, 2017.

\* cited by examiner (a)            (b)

E-PETRI DISHES, DEVICES, AND SYSTEMS HAVING A LIGHT DETECTOR FOR SAMPLING A SEQUENCE OF SUB-PIXEL SHIFTED PROJECTION IMAGES

CROSS-REFERENCES TO RELATED APPLICATIONS

This non-provisional application is a continuation-in part application of U.S. patent application Ser. No. 13/281,287 entitled "Scanning Projective Lensless Microscope System," filed on Oct. 25, 2011, which is a non-provisional application of, and claims priority to, U.S. Provisional Patent Application No. 61/406,916 entitled "Scanning Projective Microscopy System for 2D and 3D Imaging," filed on Oct. 26, 2010, and U.S. Provisional Patent Application No. 61/482,531 entitled "ePetri: An On-Chip Cell Imaging Platform based on Sub-Pixel Perspective Sweeping Microscopy" filed on May 4, 2011. This non-provisional application is also a non-provisional application of, and claims priority to, U.S. Provisional Patent Application No. 61/482,531 entitled "ePetri: An On-Chip Cell Imaging Platform based on Sub-Pixel Perspective Sweeping Microscopy" filed on May 4, 2011 and U.S. Provisional Patent Application No. 61/448,964 entitled "Electronic Petridish with Bright Field and Fluorescence Imaging Capabilities for Cell Culture Monitoring" filed on Mar. 3, 2011. All of those applications are hereby incorporated by reference in their entirety for all purposes.

This non-provisional application is related to the following co-pending and commonly-assigned patent applications, which are hereby incorporated by reference in their entirety for all purposes:

U.S. patent application Ser. No. 13/069,651 entitled "Super Resolution Optofluidic Microscopes for 2D and 3D Imaging" filed on Mar. 23, 2011.

The following non-provisional application is being filed on the same day and is hereby incorporated by reference in its entirety for all purposes: U.S. patent application Ser. No. 13/411,103 entitled "Light Guided Pixel," filed on Mar. 2, 2012.

STATEMENT AS TO RIGHTS TO INVENTIONS MADE UNDER FEDERALLY SPONSORED RESEARCH OR DEVELOPMENT

This invention was made with government support under Grant No. AI096226 awarded by the National Institutes of Health. The government has certain rights in the invention.

BACKGROUND OF THE INVENTION

Embodiments of the present invention generally relate to high resolution, wide field-of-view microscopes and other imaging devices. More specifically, certain embodiments relate to e-Petri dishes (electronic petridishes), e-Petri devices, and e-Petri systems for high resolution, wide field-of-view imaging.

The miniaturization of biomedical imaging tools has the potential to change vastly methods of medical diagnoses and scientific research. More specifically, compact, low-cost microscopes could significantly extend affordable healthcare diagnostics and provide a means for examining and automatically characterizing a large number of cells, as discussed in Psaltis, D., et al., "*Developing optofluidic technology through the fusion of microfluidics and optics,*" Nature, Vol. 442, pp. 381-386 (2006), which is hereby incorporated by reference in its entirety for all purposes. For example, miniaturized imaging systems may provide a useful alternative to large microscopes in biology labs, allowing for parallel imaging of large number of samples. Some examples of compact microscopes can be found in Cui, X., et al., "*Lensless high-resolution on-chip optofluidic microscopes for Caenorhabditis elegans and cell imaging,*" Proceedings of the National Academy of Sciences, 105(31), p. 10670 (2008), Seo, S., et al., "*Lensfree holographic imaging for on-chip cytometry and diagnostics,*" Lab on a Chip, 2009. 9(6), pp. 777-787, Breslauer, D., et al., "*Mobile phone based clinical microscopy for global health applications,*" (2009), Zheng, G., et al., "*Sub-pixel resolving optofluidic microscope for on-chip cell imaging,*" Lab on a Chip, 2010. 10(22), pp. 3125-3129, which are hereby incorporated by reference in their entirety for all purposes. Conventional optical microscopes have bulky optics, and have proven to be expensive and difficult to miniaturize.

Rapid advances and commercialization efforts in complementary metal oxide semiconductor (CMOS) imaging sensor technology has led to broad availability of cheap, high-pixel-density imaging sensor chips. In the past few years, these imaging sensor chips enabled the development of new microscopy implementations that are significantly more compact and less expensive than conventional microscopy designs with bulky optics. The optofluidic microscope and the digital in-line holographic microscope are two examples of these new developments. Some examples of optofluidic microscope technologies can be found in Heng, X., et al., "*Optofluidic microscopy—method for implementing a high resolution optical microscope on a chip,*" Lab Chip, Vol. 6, pp. 1274-1276, Cui, Xiquan, et al., "*Lensless high-resolution on-chip optofluidic microscopes for Caenorhabditis elegans and cell imaging,*" Proceedings of the National Academy of Science, Vol. 105, p. 10670 (2008), and Zheng, G., Lee, S A., Yang, S., Yang, C., "*Sub-pixel resolving optofluidic microscope for on-chip cell imaging.* Lab Chip," Lab Chip, Vol. 10, pp. 3125-3129 (2010) ("Zheng"), which are hereby incorporated by reference in their entirety for all purposes. Some examples of digital in-line holographic microscopy can be found in Repetto, L., Plano, E., Pontiggia, C., "*Lensless digital holographic microscope with light-emitting diode illumination,*" Opt. Lett., Vol. 29, pp. 1132-1134 (2004), ("Repetto"), Mudanyali, O., et al., "*Compact, light-weight and cost-effective microscope based on lensless incoherent holography for telemedicine applications,*" Lab on a Chip, Vol. 10, pp. 1417-1428 (2010) ("Mudanyali"), Xu, W., Jericho, M., Meinertzhagen, I., Kreuzer, H., "*Digital in-line holography for biological applications,*" Proc Natl Acad Sci USA, Vol. 98, pp. 11301-11305 (2001) ("Xu"), Garcia-Sucerquia, J., et al., "*Digital in-line holographic microscopy,*" Appl. Opt., Vol. 45, pp. 836-850 (2006) ("Garcia-Sucerquia"), Malek M., Allano, D., Coëtmellec, S., Lebrun, D., "*Digital in-line holography: Influence of the shadow density on particle field extraction,*" Opt. Express, Vol. 12, pp. 2270-2279 (2004) ("Malek"), Isikman, S. O., et al., "*Lens free optical tomographic microscope with a large imaging volume on a chip,*" Proc Natl Acad Sci USA, Vol. 108, pp. 7296-7301 (2011), which are hereby incorporated by reference in their entirety for all purposes.

Both optofluidic and in-line holographic microscopy technologies are designed to operate without lenses and, therefore, circumvent their optical limitations, such as aberrations and chromaticity. Both technologies are suitable for imaging dispersible samples, such as blood, fluid cell cultures, and other suspensions of cells or organisms. However, neither can work well with confluent cell cultures or any sample in which cells are contiguously connected over a sizable length scale.

In the case of an optofluidic microscope device, imaging requires fluidic (e.g., microfluidic) flow of specimens across a scanning area. Adherent, confluent, or contiguously arranged specimens are usually incompatible with imaging in a fluidic mode. In addition, the field of view may be limited by the geometry of the fluid channel.

In digital in-line holographic microscopy, the interference intensity distribution of a target under controlled light illumination is measured and then an image reconstruction algorithm is applied to render microscopy images of the target. Two examples of algorithms can be found in Liu, G., Scott, P., "*Phase retrieval and twin-image elimination for in-line Fresnel holograms*," J Opt Soc Am A, Vol. 4, pp. 159-165 (1987) ("Liu"), Fienup, J R., "*Reconstruction of an object from the modulus of its Fourier transform*," Opt Lett, Vol. 3, pp. 27-29 (1978) ("Fienup"), Koren, G., Polack, F., Joyeux, D., "*Iterative algorithms for twin-image elimination in in-line holography using finite-support constraints*, J Opt Soc Am A, Vol. 10, pp. 423-433 (1993), which are hereby incorporated by reference in their entirety for all purposes. The image quality depends critically on the extent of the target, the scattering property and the signal-to-noise ratio (SNR) of the measurement processes, which are described in Mudanyali, and Garcia-Sucerquia, Malek, Fienup, and also in Lai, S., King, B., Neifeld, M A, "*Wave front reconstruction by means of phase-shifting digital in-line holography*," Opt Commun., Vol. 173, pp. 155-160 (2000) ("Lai"), and Rodenburg, J., Hurst, A., Cullis, A., "*Transmission microscopy without lenses for objects of unlimited size*," Ultramicroscopy, Vol. 107, pp. 227-231 (2007) ("Rodenburg"), which are hereby incorporated by reference in their entirety for all purposes. The method works well for well-isolated targets, such as diluted blood smear slides. However, such approaches appear to have not been applied to targets that occupy more than 0.1 mm2 in total contiguous area coverage with submicron resolution, as found in Repetto, Madanyali, Xu, Garcia-Sucerquia, and also in Biener, G., et al., "*Combined reflection and transmission microscope for telemedicine applications in field settings*," Lab Chip, Vol. 11, pp. 2738-2743 (2011), which is hereby incorporated by reference in its entirety for all purposes.

The reason for this limitation is well-known: the loss of phase information during the intensity recording process. In order to recover the phase information, object support has to be used in the iterative phase recovery algorithm, which involves the light field propagation back and forth between the imaging domain (where the intensity data are applied) and object domain (where a priori object constrains are applied), as discussed in Liu. When the test object is real or nonnegative, it is easy to apply the powerful nonnegativity support constraint to extract the phase information from the recorded diffraction intensity, as discussed in Liu. However, for digital in-line holography, light field in the object domain is complex valued and, therefore, the phase recovery is possible only if the support of the object is sufficiently isolated (i.e., sparsity constrains) or the edges are sharply defined (true boundary), as discussed in Rodenburg and Fienup and also in Denis, L., Lorenz, D., Thiébaut, E., Fournier, C., Trede, D., "*Inline hologram reconstruction with sparsity constraints*," Opt Lett, Vol. 34, pp. 3475-3477 (2009), Zhang, F., Pedrini, G., Osten, W., "*Phase retrieval of arbitrary complex-valued fields through aperture-plane modulation*," Phys Rev A, Vol. 75, p. 043805 (2007), which are hereby incorporated by reference in their entirety for all purposes. Furthermore, the interference nature of the technique implies that coherence-based noise sources, such as speckles and cross-interference, would be present and would need to be addressed, as discussed in Garcia-Sucerquia and Malek, and also in Xu, L., Miao, J., Asundi, A., "*Properties of digital holography based on in-line configuration*," Opt Eng, Vol. 39, pp. 3214-3219 (2000), which is hereby incorporated by reference in its entirety for all purposes. Methods for mitigating problems in digital in-line holographic microscopy have been reported in Lai, Rodenburg and Micó, V., García, J., Zalevsky, Z., Javidi, B., "*Phase-Shifting Gabor Holographic Microscopy*," J Disp Technol, Vol. 6, pp. 484-489 (2010), which is hereby incorporated by reference in its entirety for all purposes. The generated images based on these mitigating methods have artifacts that may arise from interference, and are identifiably different and of lower quality than images acquired with conventional microscopes due to coherence based noise sources.

Embodiments of the invention are directed to systems that are improvements over conventional optofluidic and in-line holographic systems that use bulky optics.

BRIEF SUMMARY OF THE INVENTION

Embodiments of the present invention relate to e-Petri dishes, e-Petri devices, and e-Petri systems for high resolution, wide field-of-view imaging. The e-Petri dish includes a specimen surface and well for receiving and containing a specimen being imaged. The e-Petri dish also includes a light detector such as a CMOS imaging sensor chip with a sensing surface. The e-Petri dish also includes a transparent layer between the sensing surface and the specimen surface. The transparent layer may be part of the light detector. The e-Petri device includes the e-Petri dish and a structure for receiving the e-Petri dish. The e-Petri device also includes an illumination source (e.g., smartphone) for providing illumination from different illumination angles at different times to a specimen located on the specimen surface. The illumination from the different illumination angles generates projections of the specimen on the sensing surface. The light detector captures a sequence of sub-pixel shifted projection images of the specimen at the sensing surface. The e-Petri device also includes a processor as part of the light detector or separate from the light detector. The processor can reconstruct a higher resolution (HR) image from the sequence of sub-pixel shifted, lower resolution (LR) projection images captured by the light detector.

One embodiment is directed to an e-Petri dish comprising a transparent layer having a specimen surface and a light detector configured to sample a sequence of sub-pixel shifted projection images of a specimen located on the specimen surface. The sub-pixel shifted projection images are associated with light from a plurality of illumination angles provided by an illumination source.

Another embodiment is directed to an e-Petri device comprising a transparent layer having a specimen surface, an illumination source configured to provide light from a plurality of illumination angles to a specimen located on the specimen surface, and a light detector configured to sample a sequence of sub-pixel shifted projection images of the specimen. The sequence of sub-pixel shifted projection images corresponds to the plurality of illumination angles.

Another embodiment is directed to an e-Petri system comprising one or more e-Petri devices and a processor. Each e-Petri devices comprises a transparent layer having a specimen surface, an illumination source configured to provide light from a plurality of illumination angles to a specimen located on the specimen surface, and a light detector configured to sample a sequence of sub-pixel shifted projection images of the specimen. The sequence of sub-pixel shifted projection images corresponds to the plurality of illumination angles. The processor is configured to generate a sub-pixel resolution image of the specimen based on the sequence of sub-pixel shifted projection images from at least one of the one or more e-Petri devices.

Another embodiment is directed to a method of automatedly generating a sub-pixel resolution image of a specimen using an e-Petri system at intervals during an experiment. The method comprises introducing the specimen on a specimen surface of an e-Petri dish. During each interval, the method provides light from a plurality of illumination angles to the specimen. During each interval, the method also uses a light detector to capture a sequence of sub-pixel shifted projection images corresponding to the plurality of illumination angles. During each interval, the method also constructs a sub-pixel resolution image of the specimen based on the sequence of sub-pixel shifted projection images and a motion vector.

These and other embodiments of the invention are described in further detail below.

BRIEF DESCRIPTION OF THE DRAWINGS

FIG. 7(a) is a large field of view color HR image of a confluent HeLa cell specimen constructed by an SPLM system or an e-Petri system, according to embodiments of the invention.

FIG. 7(c1) is an LR projection image from a small region of FIG. 7(b1), captured by the light detector of an SPLM system or an e-Petri system, according to embodiments of the invention.

FIG. 7(b2) is a reconstructed HR image from the same small region of FIG. 7(a) constructed by an SPLM system or an e-Petri system, according to embodiments of the invention.

FIG. 7(c2) is a reconstructed HR image from a small region of FIG. 7(b2) constructed by an SPLM system or an e-Petri system, according to embodiments of the invention.

FIG. 7(d) is a conventional microscopy image of similar cells using a microscope with 40×, NA=0.66 objective lens.

FIG. 14 (a4) is the color image constructed based on the red, green, and blue images in FIG. 14 (a1), FIG. 14(a2), and FIG. 14(a3).

FIG. 14 (b1), FIG. 14(b2), and FIG. 14(b3) are reconstructed sub-pixel resolution images of a portion of HeLa cell sample as acquired by an e-Petri system under red, green, and blue light source scanning respectively, according to an embodiment of the invention.

FIG. 14 (b4) is the reconstructed sub-pixel resolution color image based on the red, green, and blue images in FIG. 14 (b1), FIG. 14(b2), and FIG. 14(b3), according to an embodiment of the invention.

DETAILED DESCRIPTION OF THE INVENTION

Figure 1:
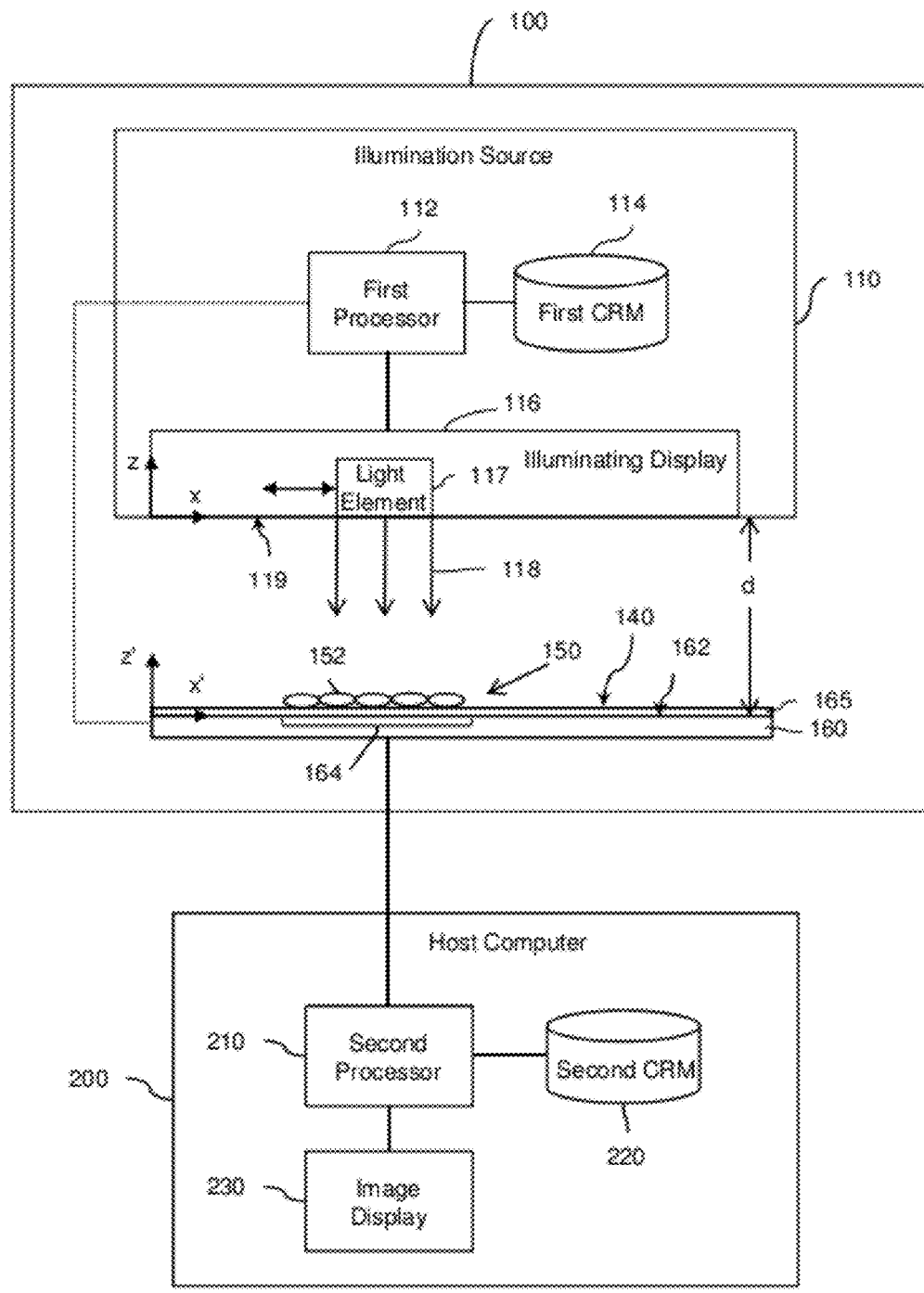
FIG. 1 is a schematic diagram of components of an SPLM system, according to embodiments of the invention.

The need for a high-resolution, wide-field-of-view, cost-effective microscopy solution for autonomously imaging growing and confluent specimens (e.g., cell cultures), especially in longitudinal studies, is a strong one, as discussed in Schroeder, T., "*Long-term single-cell imaging of mammalian stem cells,*" Nature Methods 8, pp. S30-S35 (2011), which is hereby incorporated by reference in its entirety for all purposes. Some examples of experiments that would benefit from such a solution include: 1) the determination of daughter fates before the division of neural progenitor cells, as discussed in Cohen, A. R., Gomes, F. L. A. F., Roysam, B. & Cayouette, M., "*Computational prediction of neural progenitor cell fates,*" (2010); 2) the existence of haemogenic endothelium, as discussed in Eilken, H. M., Nishikawa, S. I. & Schroeder, T., "*Continuous single-cell imaging of blood generation from haemogenic endothelium,*" Nature 457, pp. 896-900 (2009), 3) neural and hematopoietic stem and progenitor divisional patterns and lineage choice, as discussed in Costa, M. R. et al., "*Continuous live imaging of adult neural stem cell division and lineage progression in vitro,*" Development 138, 1057 (2011) and in Dykstra, B. et al., (National Acad Sciences); 4) the in-vitro tissue culture studies using the neutral red dye, as discussed in Repetto, G., del Peso, A. & Zurita, J. L., "*Neutral red uptake assay for the estimation of cell viability/cytotoxicity,*" Nature Protocols 3, 1125-1131 (2008); 5) detection of toxic compound, as discussed in Borenfreund, E. & Puerner, J. A., "*Toxicity determined in vitro by morphological alterations and neutral red absorption,*" Toxicology Letters 24, pp. 119-124 (1985); and 6) drug screening, as discussed in Cavanaugh, P. F. et al., "*A semiautomated neutral red based chemosensitivity assay for drug screening,*" Investigational new drugs 8, pp. 347-354 (1990). These cited references are hereby incorporated by reference in their entirety for all purposes. The labor intensive nature of the experiments and the challenge of efficiently imaging large assays have plagued the experiment formats in these examples and others. Embodiments of the invention may address these and other challenges.

Embodiments of the invention include e-Petri dish and SPLM devices and systems that provide a chip-scale, lensless microscopy methodology that can automadedly image growing and confluent specimens (e.g. cell cultures) over a wide field-of-view with sub-pixel (e.g., subcellular) resolution. In one embodiment, for example, an e-Petri device can image a specimen with an area of 6 mm×4 mm at 660 nm resolution. These e-Petri and SPLM devices and systems can be automated to periodically or otherwise repeatedly image specimens over time. These devices and systems can also be used image color stained specimens. Since e-Petri and SPLM devices may be compact, multiple devices can be placed in an incubator to image and track specimen changes such as cell culture growth directly within the incubator.

With these capabilities and others, this self-imaging microscopy methodology may significantly improve petri-based experiments (e.g., cell cultures) and other real-time imaging procedures in medicine and scientific disciplines. For example, by using this compact, low-cost microscopy imaging methodology, petri-dish based experiments may be transformed from the traditionally labor-intensive process to an automated and streamlined process. Further, this methodology may cut down on lab equipment usage and contamination risks. This possible technological shift from an inert petri-dish to a self-imaging petri-dish may be timely as well, because, the cost of high performance CMOS imaging sensors (which are widely used in cellphone cameras and webcams) has recently reached a price point where they can be used as recyclable or disposable components. With these capabilities, the e-Petri and SPLM devices and systems provide a smart petri-dish platform that may be well suited for long-term (cell culture) imaging and tracking applications. For example, the e-Petri and SPLM devices and systems may be used to explore time-resolved information in studying systems biology, cell growth, and in-vitro drug screening, where the counting and tracking individual cells in an in-situ and parallel manner is difficult with conventional methods such as bulky microscopes or plate readers.

These embodiments of the e-Petri and SPLM devices and systems and others will be described below with reference to the accompanying drawings. Embodiments include an e-Petri system, which includes one or more e-Petri devices having an e-Petri dish with a specimen surface and well for receiving and containing a specimen being imaged. The e-Petri system may also include an incubator, external processor, and/or other components according to embodiments of the invention. The e-Petri dish also includes a light detector (e.g., CMOS imaging sensor chip) having a sensing surface and a transparent layer between the sensing surface and the specimen surface. The e-Petri device includes an e-Petri dish along with an illumination source (e.g., smartphone) for providing illumination from different illumination angles at different times to a specimen located on the specimen surface of the e-Petri dish. The illumination from the different illumination angles generates projections of the specimen on the sensing surface. The light detector captures a sequence of sub-pixel shifted projection images at the sensing surface of the specimen. The e-Petri system also includes a processor, which may or may not be incorporated with any component of the system. The processor can reconstruct a higher resolution image from the sequence of sub-pixel shifted projection images captured by the light detector. Other embodiments include an SPLM device having a specimen surface for receiving a specimen being imaged, an illumination source, a light detector having a sensing surface, a transparent layer between the sensing surface and the specimen surface, and a processor.

The e-Petri and SPLM devices and systems use the same general imaging method. First, a specimen is located on the specimen surface of the device. During an illumination cycle, an illumination source provides light from different illumination angles to the specimen. For example, if an LCD is used, the light element may be in the form of different sets of light pixels that illuminate at different times to change the position of the light element. The positions of the different sets of light emitting component can be in a pattern designed to generate sub-pixel shifted projections of the specimen at the sensing surface of the light detector. The light detector can capture a sequence of these sub-pixel shifted projection images (frames) at the sensing surface. A processor can calculate the motion vector of the sub-pixel shifted projections using a suitable estimation algorithm. The processor can then use a super resolution algorithm to construct a sub-pixel resolution or other HR image of the specimen from the sequence of sub-pixel shifted projection images and the calculated motion vector. Under different imaging schemes, the e-Petri and SPLM devices/systems can generate HR monochromatic 2D images, HR monochromatic 3D images, HR color 2D images, and/or HR color 3D images. In a digital focusing scheme, these devices/systems can focus a HR image of the specimen at a plane through the specimen using a motion vector calculated at that plane to construct an HR image.

This imaging method leverages the recent broad and cheap availability of high performance image sensor chips to provide a low-cost and automated microscopy solution. Unlike the two major classes of lensless microscopy methods, optofluidic microscopy and digital in-line holography microscopy, this imaging method is fully capable of working with cell cultures or any samples in which cells may be contiguously connected.

Embodiments of the invention provide one or more technical advantages. In embodiments, the illumination source is located at a larger distance from the sensing surface as compared with the distance between the specimen and the sensing surface. Thus, small translations of the light element correspond to larger translations of the projections on the sensing surface. With this geometry, the illumination source can easily and accurately control and maintain sub-pixel shifts of the projections. These devices can then generate an accurate sub-pixel resolution image based on the accurately controlled sub-pixel shifted projections. In some embodiments, the devices can generate images with a resolution compatible to conventional 20×-40× objective microscopes. This can provide an advantage over other systems, such as prior microscanning systems, that used actuators and controller to control sub-pixel movements of the object or a platform holding the object.

Other advantages of embodiments are that this method may provide an autonomous, cost effective, high resolution microscopic solution for high resolution imaging of confluent specimens and other specimens in which objects in the specimen may be contiguously connected over a sizable length. One advantage is that the systems and devices may be made compact (e.g., on the chip-scale) and at lower cost than convention microscopy. Since these systems and devices may be compact and low cost, multiple devices can easily be used in parallel to image many specimens. For example, several e-Petri devices may be placed in a single incubator and monitored using the display on single laptop computer. With this compact platform, lab testing may become more streamlined and require less lab equipment allocation. Another advantage is that the systems and devices can automatedly image and produce other data, which may reduce the human labor involved in lab experiments. Some benefits of automated imaging can be found in Levin-Reisman, I., et al., "*Automated imaging with ScanLag reveals previously undetectable bacterial growth phenotypes*," Nat Meth, 7(9), pp. 737-739 (2010), which is hereby incorporated by reference in its entirety for all purposes. Due to the automated nature of the imaging used by the devices of embodiments, contamination risks may be reduced. Also, experimental procedures may be significantly streamlined and may be more accurate.

Components of the SPLM systems and devices are discussed in detail in Section I, which also describes some components of e-Petri systems and devices. The imaging method used by the SPLM and e-Petri systems and devices is discussed in Section II. Components of the e-Petri systems and devices are discussed in detail in Section III. Some components of e-Petri systems and devices are also described in detail in Section I.

I. Scanning Projective Lensless Microscope (SPLM) System

FIG. 1 is a schematic diagram of components and partial components of an SPLM system 10, according to embodiments of the invention. The SPLM system 10 includes an SPLM device 100 and a host computer 200.

The SPLM device 100 includes a specimen surface 140 for receiving a specimen (e.g., confluent sample). The SPLM system 10 can image at least a portion of the specimen 150. In the illustrated example, a specimen 150 with five objects 152 (e.g., cells) is located on the specimen surface 140. Although five objects 152 are shown, the specimen 150 may have any suitable number (e.g., 1, 2, 10, 100, 1000, etc.) or portion(s) of objects 152.

The SPLM device 100 also includes a scanning illumination source 110 having a first processor 112, a first computer readable medium (CRM) 114, and an illuminating display 116 (e.g., an LCD, a light emitting diode (LED) display, etc.). The first processor 112 is in electronic communication with the illuminating display 116 and with the first CRM 114. The illuminating display 116 includes a light element 117 (e.g., one or more pixels of an LCD or LED display)) capable of generating illumination 118 (e.g., incoherent light). The illuminating display 116 also includes a display surface 119. The light element 117 is located at the display surface 119 in the illustrated example. In other embodiments, a transparent layer may be located between the display surface 119 and the light element 117. Also, a transparent layer may be located outside the display surface 119 in some embodiments. The scanning illumination source 110 also includes an x-axis, a y-axis (not shown), and a z-axis. The x-axis and y-axis lie in a plane at the display surface 119. The z-axis is orthogonal to this plane.

Figure 3:
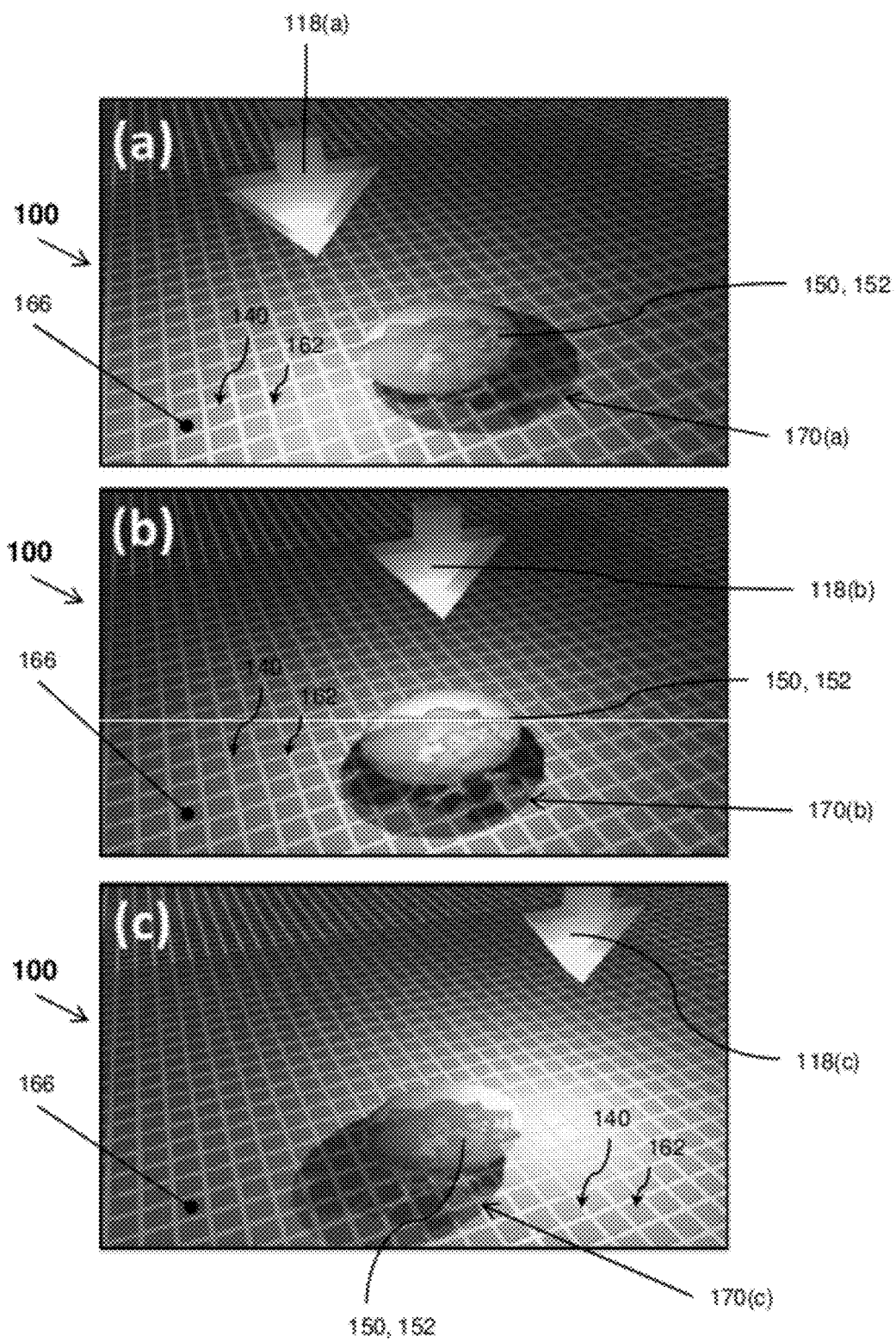
FIGS. 3(a), 3(b), and 3(c) are drawings of perspective views of components and partial components of an SPLM device or an e-Petri device during an illumination cycle of an imaging run, according to embodiments of the invention.

The scanning illumination source 110 can scan (sweep) or otherwise translate the light element 117 to different scanning locations across the display surface 119 in order to provide illumination 118 to the specimen 150 from different illumination angles. The shifting light element 117 (source) of the illumination 118 generates shifting projections 170 (as shown in FIG. 3) of a specimen 150 on the sensing surface 162. In FIG. 1, the light element 117 is shown at a scanning position at a time, t during the scanning cycle of an imaging run. Each scanning cycle of an SPLM device 100 can refer to a time interval during which the scanning illumination source 110 scans or otherwise translates the light element 117 to the scanning locations in that particular scanning cycle. An imaging run of an SPLM device 100 can refer a time interval during which one or more operations of the SPLM system 10 generates an HR image based on light data collected during one or more scanning cycles. In embodiments, the light element 117 may shift during a scanning cycle to n×m scanning locations in a two-dimensional (n×m) array of scanning locations: $(x_{i=1 \text{ to } n}, y_{j=1 \text{ to } m})$ on the display surface 119.

The SPLM device 100 also includes a light detector 160 for capturing projection images. The light detector 160 includes a sensing surface 162 having a sensing area 164. The sensing surface 162 is located at a distance, d, from the display surface 119. The light detector 160 also includes a transparent layer 165 (e.g., thin transparent passivation layer) located between the specimen surface 140 and the sensing surface 162. During a scanning cycle, the illumination 118 from the light element 117 generates projections 170 (shown in FIG. 3) of the specimen 150 on the sensing surface 162. The light detector 160 can sample (capture) one or more sequences of sub-pixel shifted LR projection images of the specimen 150 during a scanning cycle. Each sub-pixel shifted LR projection image can refer to an LR projection image that has shifted a sub-pixel distance from a neighboring LR projection image in the sequence. Neighboring LR projection images in a sequence can refer to two LR projection images that are proximal in distance. In some cases, neighboring LR projection images may also be projection images that have been sequentially captured in time during a scanning cycle.

As shown by a dotted line, the light detector 160 may optionally be in electronic communication with the first processor 112 for synchronization of sampling by the light detector 160 with scanning by the scanning illumination source 110. The light detector 160 also includes an x'-axis, a y'-axis (not shown), a z'-axis. The x'-axis and y'-axis lie in a plane at the sensing surface 162 of the light detector 160. The z'-axis is orthogonal to this plane.

The SPLM system 10 also includes a host computer 200 having a second processor 210, a second CRM 220 in electronic communication with the second processor 210, and an image display 230 in electronic communication with the second processor 210. The second processor 210 can receive data associated with one or more sequences of sub-pixel shifted LR projection images from the light detector 150. The second processor 210 can also determine a motion vector of the projections 170 at the sensing surface 162 based on the data. The second processor 210 can then use a suitable super resolution algorithm (SR algorithm) to generate one or more HR (e.g., sub-pixel resolution) images of the specimen 150 based on the motion vector and data of one or more sequences of sub-pixel shifted LR projection images. The second processor 210 is in electronic communication with the second processor 210 to display the HR images and/or other images.

In an exemplary imaging run of the SPLM system 10 of FIG. 1, the scanning illumination source 110 scans or otherwise translates the light element 117 to a two-dimensional (n×m) array of n×m scanning positions having the coordinates ($x_{i=1 \text{ to } n}$, $y_{j=1 \text{ to } m}$) on the display surface 119. The scanning illumination source 110 scans (sweeps) or otherwise translates the light element 117 to scanning positions according to a scanning pattern. Illumination 118 from the light element 117 at the different scanning locations generates shifted projections 170 of the specimen 150 on the sensing surface 162 of the light detector 160. During scanning, the light detector 160 captures one or more sequences of sub-pixel shifted LR projection images at the sensing area 164. The second processor 210 receives data for at least one of the sequences from the light detector 160. The second processor 210 can determine a motion vector of the sub-pixel shifted projections 170 at the sensing surface 162 from the data. The second processor 210 can also construct one or more HR images of the specimen 150 using a suitable super-resolution algorithm with the data from at least one of the sequences of sub-pixel shifted LR projection images of the specimen 150 and/or the determined motion vector.

Figure 2:
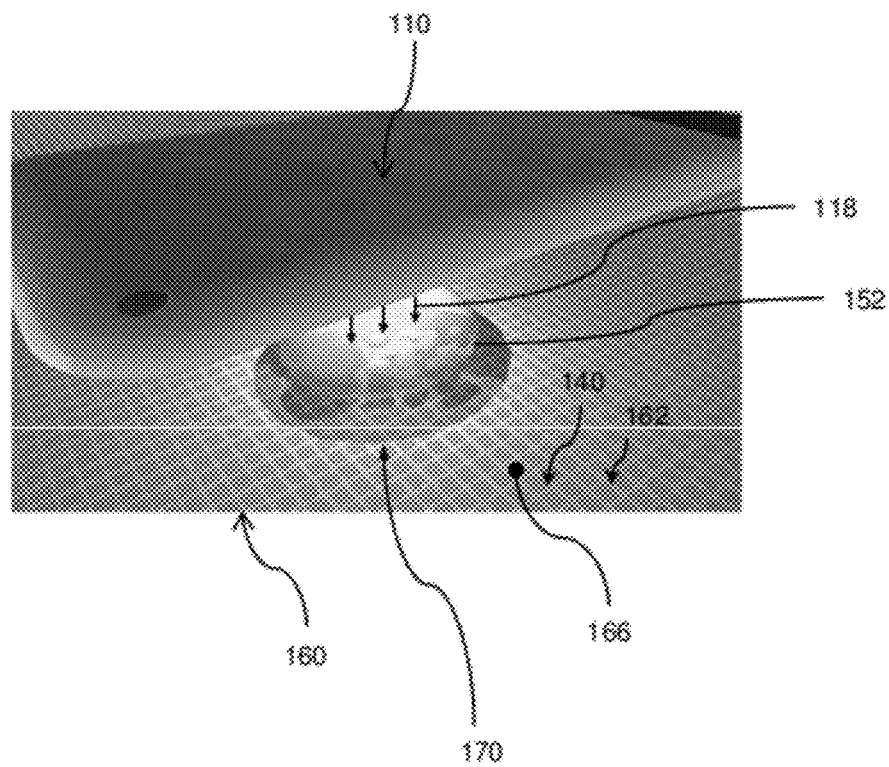
FIG. 2 is a drawing of a perspective view of components and partial components of an SPLM device or an e-Petri device, according to embodiments of the invention.

FIG. 2 is a drawing of a perspective view of components and partial components of an SPLM device 100 or an e-Petri device, according to embodiments of the invention. The SPLM device 100 or an e-Petri device includes a scanning illumination source 110 in the form of a mobile communication device (e.g., cell phone, tablet, etc.) and a light detector 160 in the form of a two-dimensional array of light detecting elements 166 (e.g., CMOS imaging sensor). The light detector 160 has a sensing surface 162 and a thin transparent layer 165. A specimen 150 comprising a single object 152 (e.g., cell) is located on the specimen surface 140 (not shown). The thin transparent layer 165 lies between the sensing surface 162 and the specimen surface 140. In this example, scanning illumination device 110 includes an illuminating display 116 (not shown) in the form of an LCD. The LCD includes a two-dimensional array of light emitting components (e.g., pixels). The scanned light element 117 is in the form of subsequent sets of light emitting components on the LCD 116 providing illumination 118 according to a scanning pattern. Each set may include one or more light emitting components. The subsequent sets of light emitting components provide illumination 118 at the two-dimensional (n×m) array of n×m scanning locations at ($x_{i=1 \text{ to } n}$, $y_{j=1 \text{ to } m}$) on the display surface 119. In FIG. 2, the light element 117 is shown at a single scanning location in the scanning cycle. The illumination 118 from the light element 117 generates a single projection 170 of the object 152 on the sensing surface 162 of the light detector 160.

FIGS. 3(a), 3(b), and 3(c) are drawings of perspective views of components and partial components of an SPLM device 100 or an e-Petri device during a scanning cycle of an imaging run, according to embodiments of the invention. The SPLM device 100 or an e-Petri device includes a scanning illumination source 110 providing illumination 118 and a light detector 160 in the form of a two-dimensional array of light detecting elements 166. The light detector 160 has a sensing surface 162 and a thin transparent layer 162. A specimen 150 comprising a single object 152 (e.g., cell) is located on the specimen surface 140. The thin transparent layer 165 lies between the sensing surface 162 and the specimen surface 140. The SPLM device 10 or an e-Petri device also includes an x-axis, a y-axis, and a z-axis. The x-axis and y-axis lie in the plane at the sensing surface 162 of the light detector 160. The z-axis is orthogonal to this plane. The light element (not shown) 117 provides illumination 118 and generates light spots on the light detector 160.

In FIGS. 3(a), 3(b), and 3(c), the light element 117 (not shown) is located at three scanning positions along the x'-axis at times: $t=t_a$, $t_b$, and $t_c$ (a>b>c), respectively. Illumination 118 is shown from three different scanning position to generate three shifted projections 170(a), 170(b), and 170(c) on the sensing surface 162, respectively. With certain shifts of the light element 117, the object's projection (shadow) can be shifted at sub-pixel (i.e. smaller than pixel size) increments across the light detecting elements 166 (e.g. sensor pixels) of the light detector array. At times: $t=t_1$, $t_2$, and $t_3$, the light detector 160 captures a sequence of three LR projection images corresponding to the three projections 170(a), 170(b), and 170(c), respectively. Any suitable number of sub-pixel shifted projections may have been captured at scanning times between times, $t_a$ and $t_b$ or between times, $t_b$ and $t_c$. A motion vector of the projections 170(a), 170(b), and 170(c) at the sensing surface 162 can be determined based on the data from a sequence of sub-pixel shifted LR projection images. An HR image of the object 152 can be constructed using a suitable SR algorithm and based on the data from a sequence of sub-pixel shifted LR projection images captured by the light detector 160.

Any suitable specimen 150 may be imaged by the SPLM system 10 or the SPLM device 100. In most cases, the specimen 150 is stationary during a scanning cycle. An example of a suitable specimen 150 is a confluent sample (e.g., confluent cell cultures) having one or more objects 152 (e.g., cells). Another example of a suitable specimen 150 is a sample in which the objects 152 are contiguously connected. The specimen 150 being imaged may include any suitable type(s) of object(s) 150 and may include any suitable number (e.g., 1, 10, 100, 1000, etc.) of objects 150 or portion(s) of an object 150. Suitable types of objects 150 can be biological or inorganic entities. Examples of biological entities include whole cells, cell components, microorganisms such as bacteria or viruses, cell components such as proteins, etc. Inorganic entities may also be imaged by embodiments of the invention.

As used herein, a scanning illumination source 110 can refer to any suitable device or combination of devices capable of scanning or otherwise translating a light element 117 to n scanning positions to generate sub-pixel shifted projections 170 of a specimen 150 being imaged at a sensing surface 162 of a light detector 160. Any number, n, of scanning positions can be used (n=1, 2, 3, 4, 5, 10, 20, 100 etc.). By moving the light element 117, the scanning illumination source 110 changes the illumination angles of the illumination 118 provided to the specimen 150. In embodiments, the scanning illumination source 110 moves the light element 117 to scanning locations that generate a small range of illumination angles (e.g., +/−2 degrees) in X/Y around the normal to the sensing surface or other plane of interest.

An example of a suitable scanning illumination device 110 is a mobile communication device (e.g., cell phone, tablet, etc.). Suitable scanning illumination sources 110 commercially available. Illustrated examples of a suitable scanning illumination device 110 in the form of a smartphone are shown in FIGS. 2 and 4. Another example of a suitable scanning illumination device 110 may be a tomographic phase microscope that uses a spatial light modulator to scan illumination.

In embodiments, the scanning illumination source 110 may include an illuminating display 116 for scanning the light element 117 to generate sub-pixel shifted projections 170 at the sensing surface 162. An illuminating display 116 can refer to any suitable display capable of translating a light element 117 to scanning locations across at least a portion of a display surface 119. Suitable illuminating displays 116 are commercially available. Some examples of suitable illuminating displays 116 include monochromatic, color, or grayscale LCDs, LED displays (e.g., display panels), television screens, LCD matrixes, etc. In these embodiments, the illuminating display 116 may include a two-dimensional array of light emitting components (e.g., pixels). The array of light emitting components may have any suitable dimension (e.g., 1000×1000, 1000×4000, 3000×5000 etc.). The display surface 119 can refer to a surface of the illuminating display 116 that provides illumination 118. For example, the scanning illumination source 110 may be in the form of a smartphone with an illuminating display 116 in the form of an LCD screen, as shown in FIGS. 2 and 4. In other embodiments, the scanning illumination source 110 may include another device or combination of devices capable of scanning the light element 117 to generate sub-pixel shifted projections 170 at the sensing surface 162.

The scanning illumination source 110 may be held at a fixed position relative to the light detector 160 and the transparent layer 165 during scanning in some embodiments. In these embodiments, the SPLM 100 may include a suitable structure (e.g., platform, frame, etc.) or structures to hold the scanning illumination source 110 and light detector 160 in a fixed position. In some cases, such as the illustrated example of FIG. 1, the scanning illumination source 110 may be held such that the display surface 119 is kept approximately parallel to the sensing surface 162 of the light detector 160 and at a distance, d, from the sensing surface 162 during scanning. In these cases, the illuminating display 116 may provide illumination 118 at angles normal to the display surface 119. In other cases, the scanning illumination source 110 may be held so that the display surface 119 may be tilted at an angle from normal. At this angle, projections 170 from more extreme illumination angles to be captured, leading to a more complete 3D reconstruction in some cases. In one embodiment, the scanning illumination source 110 may include actuator(s) and controller(s) or other mechanism to reposition the illuminating display 116 (e.g., LCD array) at an angle from normal.

A light element 117 can refer to a suitable device capable of providing illumination 118. The properties of the illumination 118 generated by the light element 117 can have any suitable values. Some properties of the illumination 118 include intensity, wavelength, frequency, polarization, phase, spin angular momentum and other light properties associated with the illumination 118 generated by the light element 117. In embodiments, the illumination 118 is incoherent light. The component or components of the light element 117 can change over time. For example, in the case of an LCD, different pixels may illuminate at different times to change the position of the light element 117.

In embodiments with an illuminating display 116 in the form of a two-dimensional array of light emitting components (e.g., pixels), a light element 117 at a particular scanning time, t may be a set of a suitable number (e.g., 1, 5, 10, 100, etc.) of illuminated light emitting components (e.g., LCD lit/pixel) in the two-dimensional array (e.g., LCD array). Each light emitting component may have a scanning location denoted as $(x_i, y_j)$ where i=1 ... N; and j=1 ... N. The light element 117 may be the illuminated pixels in the array at a scanning time in the scanning cycle. The scanning location of a light element 117 can refer to the coordinates of the center of the set of illuminated light emitting components in this case. In these embodiments, sequentially illuminated sets of light emitting components(s) on an illuminating display 116 can generate light elements 117 at different scanning locations during a scanning cycle.

The properties (e.g., size, properties of the illumination 118, shape, etc.) of the light element 117 may have any suitable value. In embodiments, one or more properties of the light element 117 may vary at different scanning locations in a scanning cycle. In other embodiments, the properties of the light element 117 may be constant during the scanning cycle. Some examples of suitable shapes of a light element 117 are a rectangle, circle, spot, bar, etc. In embodiments with an illuminating display 116 in the form of a two-dimensional array of light emitting components, the properties of the light element 117 can be varied by varying the number of light emitting components in the set of light emitting components (e.g., pixels) forming the light element 117. For example, the intensity of the illumination 118 generated by the light element 117 can be varied by changing its number of light emitting components (e.g., pixels). In embodiments, one or more properties of the illumination 118 generated by the light element 117 may change at different scanning locations.

In embodiments, the intensity of the illumination 118 generated by the light element 117 may be controlled by varying the size of the light element 117. In one embodiment, the size of the light element 117 may vary at different scanning locations to generate light at approximately the same intensity at a single point at the plane of the sensing surface 162. In this embodiment, the size, S of the light element 117 at a scanning location can be proportional to the distance, L, from the scanning location to a suitable location such as: a) the center of the array of scanning locations, or b) the center of an illuminating display 116 such as the center of an LCD on a smartphone. For example, the size, S of the light element 117 at a scanning location may be defined as: $S=S_{center} \times (1+L)$, where $S_{center}$ is the size of the light element 117 at the center of the array of scanning locations. In this way, the light intensity received at a location at the sensing surface 162 normal to the center of the scanning locations on the display surface 119 can be kept about constant in some cases. As another example, the size S of the light element 117 at a scanning location in a scanning cycle may be defined as: $S=S_A \times (1+A)$, where $S_A$ is the size of the light element 117 at a location A of an illuminating display 116, A is the distance from the scanning location to the location A.

In one embodiment, the light element 117 can provide illumination 118 of n different wavelengths $\lambda_1, \ldots, \lambda_n$ at different scanning times during a scanning cycle. The illumination 118 may be sequentially cycled through a series of different wavelengths as the light element 117 moves through scanning locations in a scanning cycle in some examples. In one example, the light element 117 can provide RGB illumination of three wavelengths $\lambda_1$, $\lambda_2$, and $\lambda_3$ corresponding to red, green, blue colors, respectively. The light element 117 may provide illumination 118 of the three wavelengths $\lambda_1$, $\lambda_2$, and $\lambda_3$ sequentially during scanning times of a scanning cycle. In one case, at a scanning time $t_1$ illumination 118 may have a wavelength of $\lambda_1$, at $t_2$ illumination 118 may have an wavelength of $\lambda_2$, at $t_3$ illumination 118 may have a wavelength of $\lambda_3$, at $t_4$ illumination 118 may have a wavelength of $\lambda_1$, at $t_5$ illumination 118 may have a wavelength of $\lambda_2$, etc.

A scanning location can refer to the center of the light element 117. Any suitable number (e.g., 1, 100, 1000, etc.) of scanning locations may be used in a scanning cycle. As a group, the scanning locations in a scanning cycle may cover any suitable area. In embodiments with a display surface 119, the scanning locations may cover the entire display surface 119 or may cover a portion of the display surface 119.

To shift projections 170 of the specimen 152 at the sensing surface 162, the scanning illumination source 110 can translate the light element 117 to different scanning locations generating different illumination angles. To generate a sequence of sub-pixel shifted projections 170 of the specimen 152 at the sensing surface 162 in some embodiments, the scanning illumination source 110 may move the light element 117 to a plurality of scanning locations designed to generate sub-pixel shifted projections 170. In this case, neighboring scanning locations in the plurality of scanning locations correspond to a sub-pixel shift of neighboring projections images 170 in the sequence of projection images. Neighboring scanning locations can refer to two scanning locations that are proximal in distance. In some cases, neighboring scanning locations may also be locations that are sequential in time having sequential scanning times during a scanning cycle.

The scanning locations may form any suitable arrangement (e.g., array, circle, square, triangle, etc.). In embodiments, the scanning locations may be in the form of an array (e.g., one-dimensional array, two-dimensional array, or combination of one-dimensional and two-dimensional arrays) of scanning locations. In these embodiments, the array of scanning locations may have any suitable dimension (e.g. 1×100, 1×10, 100×100, 3000×20, 400×300 etc.). For example, the scanning locations may be arranged in a two-dimensional (n×m) array of n×m scanning locations at $(x_{i=1 \text{ to } n}, y_{j=1 \text{ to } m})$.

In embodiments with an illuminating display 116 (e.g., LCD display) in the form of a two-dimensional array of light emitting components (e.g. pixels), the scanning locations of the light element 117 can refer to subsequently illuminated light emitting components in the two-dimensional array. In these embodiments, the scanning locations of the light element 117 may be located at the display surface 119. For example, the scanning locations may be in the form of a two-dimensional (n×m) array of n×m scanning locations at $(x_{i=1 \text{ to } n}, y_{j=1 \text{ to } m})$ on the display surface 119.

In embodiments, the scanning illumination source 110 the light element 117 during a scanning cycle according to a scanning pattern. A scanning pattern can refer to a description of the scanning locations (i.e. locations of the light element 117) at different times during a scanning cycle and properties (e.g., size, shape, etc.) of the light element 117 at each scanning location in the scanning cycle. For example, a scanning pattern may include a two-dimensional array of scanning locations and a description that the light element 117 moves through each row sequentially at a constant rate. In another example, the scanning pattern may include a two-dimensional array of scanning locations and a description that the element moves through each column sequentially at a constant rate. As another example, the scanning pattern may include a two-dimensional array of scanning locations and a description that the element moves through the array randomly. The scanning pattern may also include the amount of sub-pixel shift desired between subsequent LR projection images. The scanning pattern may also include the total number of LR projection images and/or HR images desired. The scanning pattern may be stored as code on the first CRM 114 or the second CRM 220. In embodiments with a scanning illumination source 110 in the form of a smartphone such as in FIG. 4, the scanning pattern may be an application (App) stored in the memory of the smartphone.

In embodiments such as the illustrated example of FIG. 1, the SPLM device 100 also includes a transparent layer 165 located between the specimen surface 140 and the sensing surface 162. The transparent layer 165 can separate the specimen 150 from the light sensitive region of the light detector 160. The transparent layer 165 may be made of any suitable material such as Polydimethylsiloxane (PDMS). The transparent layer 165 may have any suitable thickness (e.g., thickness in the range of several hundred nanometers to microns). In some cases, the transparent layer 165 may be a layer placed on the light detector 160. For example, the transparent layer 165 may be a passivation layer coated or deposited on top of an imaging sensor chip. In other cases, the transparent layer 165 may be separate from the light detector 160. In other embodiments, the SPLM device 100 does not have a transparent layer 165 and the sensing surface 162 is coincident with the specimen surface 140. The transparent layer may also be comprised of multiple layers. For example, the transparent layer may be comprised of a passivation layer proximal the light detector 160 and a protective coating.

The distance between neighboring projections 170 is proportional to the thickness of the transparent layer 165 and the tilt/shift extent of the light element 117. The tilt/shift extent of the light element 117 can refer to the distance or illumination angle change between neighboring scanning locations. In some embodiments, the distance between neighboring scanning locations in a plurality of the scanning locations of a scanning cycle can be designed to generate sub-pixel shifted projections 170. In these cases, the distance between the neighboring scanning locations can be determined based on the thickness of the transparent layer 165 and the required incremental sub-pixel shifts between neighboring projections 170.

In embodiments, the distance between neighboring scanning locations in a plurality of scanning locations may be determined to generate sub-pixels shifts between neighboring projections 170 in a sequence of projection images. In these embodiments, the determined distance between neighboring scanning locations in the plurality of scanning locations directly corresponds to a sub-pixel shift of a projection 170 at the sensing surface 162. In these embodiments, the plurality of scanning locations directly corresponds to a sequence of sub-pixel shifted projection images.

In embodiments, the distance between neighboring scanning locations may be a suitable value. In some cases, the distance between neighboring scanning locations in a given scanning cycle may be constant. In other cases, it may vary.

A scanning rate can refer to the rate of shifting between sequential scanning locations in a scanning cycle per unit in time. A sampling rate can refer to a rate of projection images (frames) captured by the light detector 160 per unit in time such as frames per second. The sampling/scanning rate may be constant in some embodiments and may vary in other embodiments. In embodiments, the scanning rate and sampling rate are synchronized.

Figure 4A:
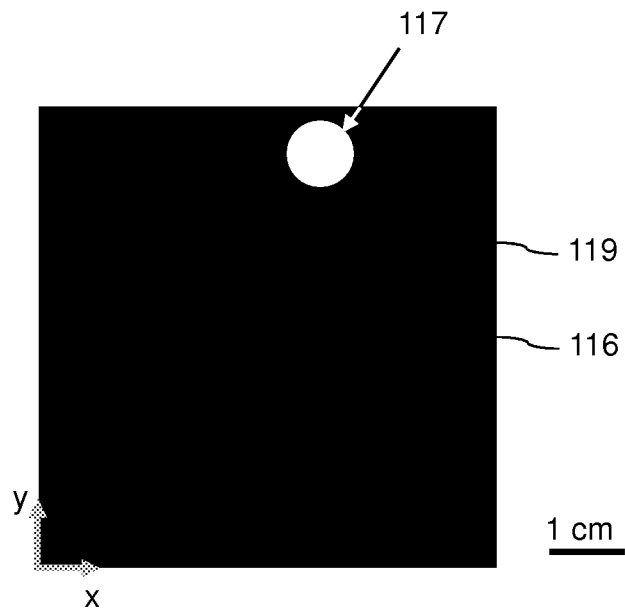
FIG. 4(a) and FIG. 4(b) are diagrams illustrating a scanning pattern on an illuminating display, according to embodiments of the invention.
Figure 4B:
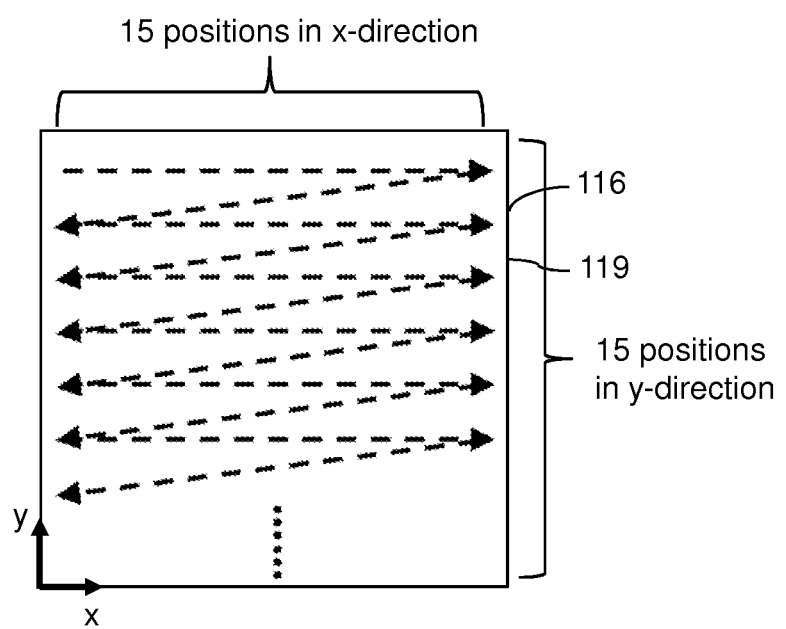

FIG. 4(a) and FIG. 4(b) are diagrams illustrating a scanning pattern on an illuminating display 116, according to embodiments of the invention. In this example, the scanning illumination source 110 is in the form of a smartphone and the illuminating display 116 is in the form of an LCD screen of the smartphone. The LCD screen includes a two-dimensional array of pixels of a 640×640 pixel size. During scanning, the smartphone may be located at a suitable distance, d above the light detector 160 (e.g., image sensor chip). The display surface 119 of the illuminating display 116 and the sensing surface 162 of the light detector 160 may be kept approximately parallel. The smartphone may be located so that the center of the display surface 119 of the illuminating display 116 is above the sensing area 164 of the sensing surface 162 of the light detector 160. The illuminating display 116 includes an x-axis and a y-axis. The x-axis and y-axis lie in the plane at the display surface 119 of the illuminating display 116.

FIG. 4(a) shows a light element 117 comprising a set of about 640 pixels in the form of a bright circular spot of about 1 cm in diameter on the illuminating display 116. The light element 117 is shown at a scanning location at a scanning time during a scanning cycle. The light element 117 may be located at the display surface 119 of the illuminating display 116.

In FIG. 4(b), the diagram of the scanning pattern includes a 15×15 array of scanning locations (steps) of the light element 117 during the scanning cycle. The scanning locations are shown at locations along the x-axis and y-axis in the plane of the display surface 119 of the illuminating display 116. In the illustrated example, the scanning pattern includes 15 scanning locations in the x-direction and 15 scanning locations in the y-direction. In this example, the light detector 160 may capture 225 LR projection images based on the 225 scanning locations in the scanning patter. The array of scanning positions may be centrally located within the illuminating display 116. The arrows in FIG. 4(b) designate the order of the scanning locations during the scanning cycle. In this case, the light element 117 moves sequentially through each row of the two-dimensional array of scanning locations in the scanning pattern. If the light element 117 remains a constant size as it moves away from the center of the display surface 119, the intensity readout from the light detector 160 (e.g., image sensor chip) will decrease because of the large incident angle. To maintain a more constant intensity readout, the size of the light element 117 (e.g., bright spot size) can be linearly increased as it moves away from the center of the illuminating display 116 (e.g., smartphone screen) in one embodiment.

Returning to FIG. 1, the scanning illumination source 110 includes a first processor 112 in electronic communication with the illuminating display 116 and a first CRM 114 in communication with the first processor 112. The first processor 112 (e.g., microprocessor) can execute code stored on the first CRM 114 (e.g., memory) to perform some of the functions of the scanning illumination source 110. For example, the first processor 112 may execute code with a scanning pattern stored on the first CRM 114. The CRM 114 may include, for example, code with a scanning pattern, other code for scanning a light element 117, and other codes for other functions of the scanning illumination source 110. The first CRM 114 may also include code for performing any of the signal processing or other software-related functions that may be created by those of ordinary skill in the art. The code may be in any suitable programming language including C, C++, Pascal, etc.

In embodiments, the light detector 160 may be in electronic communication with the first processor 112 of the scanning illumination source 110 to synchronize sampling of the light detector 160 with the light element 117 being located at a scanning position. In these embodiments, the sampling rate of the light detector 160 may be synchronized with the scanning rate of the scanning illumination source 110 to capture at least one projection image 170 at each scanning location. In one embodiment, an electronic start sampling signal may be sent to the light detector 160 from scanning illumination source 110 to capture an LR projection image when the light element 117 is at a scanning location.

The SPLM device 100 also includes a light detector 160 (e.g., CMOS imaging sensor). As used herein, a light detector 160 can refer to any suitable device or combination of devices capable of capturing projection images 170 and generating one or more signals with data associated with the projection images 160 captured and other data associated with imaging. The signals with data may be in the form of an electrical current from the photoelectric effect.

The light detector 160 includes a sensing surface 162. As used herein, a sensing surface 162 can refer to the active sensing layer of the light detector 160. The sensing surface 162 includes a sensing area 164. The sensing area 164 refers to a suitable area of the sensing surface 162 that actively captures projections 170 during a scanning cycle. In some cases, the entire area of a sensing surface 162 is the sensing area 164. In embodiments, the specimen 150 being imaged may be located in an area of the specimen surface 140 proximal the sensing area 162. The light detector 160 also includes a local x' axis and y' axis at a plane of the sensing surface 162.

In embodiments, the light detector 160 includes discrete light detecting elements 166 (e.g., pixels) in the form of a two-dimensional array of light detecting elements 166, as shown in FIGS. 2 and 3. The light detecting elements 166 may be located on or within a surface layer of the light detector 160 at the sensing surface 162. Although the two-dimensional array of light detecting elements 166 is oriented so that the x'-axis is parallel to the x-axis of the illuminating display 116 as shown in FIGS. 2 and 3, the two-dimensional array may be oriented at any suitable angle in other embodiments.

Any suitable light detector 160 can be used. Some examples of suitable light detectors 160 having two-dimensional arrays of light detecting elements 166 include a charge coupled device (CCD) array, a CMOS imaging sensor array, an avalanche photo-diode (APD) array, a photo-diode (PD) array, and a photomultiplier tubes (PMT) array. These light detectors 160 and others are commercially available. Also, the light detector 160 can be a monochromatic detector or a color detector (e.g., RGB detector).

The light detecting elements 166 may be of any suitable size (e.g., 1-10 microns) and any suitable shape (e.g., circular, rectangular, square, etc.). For example, a CMOS or CCD light detecting element 166 may be 1-10 microns and an APD or PMT light detecting element 166 may be as large as 1-4 mm.

Due to the scattering angle of light 118 passing through a specimen 150 being imaged, projection image quality can be degraded if the specimen 150 is located away from the sensing surface 162 of the light detector 160. In embodiments, the light detector 160 does not have a color filter and microlens layer in order to decrease the acceptance angle of each light detecting element and the distance between the object 152 and the sensing surface 120 (i.e. the active sensing layer). If the light detector 160 (e.g., a CMOS imaging sensor chip) was prefabricated with a color filter and a microlens layer, these components may be removed to decrease the acceptance angle of each pixel and the distance between the object 152 and the surface layer.

In embodiments, the transparent layer 165 may be placed, during fabrication, on the light detector 160. Semiconductor and/or micro/nanofabrication procedures may be used to place the transparent layer 165 on the light detector 160. In some cases, the transparent layer 165 may be placed on the light detector 160 after the color filter and microlens layer have been removed. In one case, the color filter and microlens layer may be removed by treating the pre-fabricated imaging sensor under oxygen plasma for a period of time (e.g., 10 minutes at 80 W). The transparent layer 165 may be placed onto the imaging sensor after the removal of the color filter and microlens layer or may be placed on a light detector with the layer. In one case, the transparent layer 165 may be prepared by mixing 1:10 with base and curing agent, then spin coated on a 3 in. silicon wafer followed by baking at 80 degrees C.

Light data can refer to any suitable information related to the one or more projections 170 captured by the light detecting elements 166 of the light detector 160. For example, light data may include information about the properties of the projection light received such as the intensity(ies) of the light, the wavelength(s) of the light, the frequency or frequencies of the light, the polarization(s) of the light, the phase(s) of the light, the spin angular momentum(s) of the light, and/or other light properties associated with the light received by the light detecting element 166. Light data may also include the location of the receiving light detecting element(s) 166, the time that the light was received (sampling time or scanning time), or other information related to the projection 170 received. In embodiments, each light detecting element 166 can generate a signal with light data based on light associated with the projection 170 and received by the light detecting element 166.

An LR projection image (frame) can refer to a snapshot image sampled (captured) by the light detector 160 at a sampling time occurring during a scanning cycle. In embodiments, the light detector 160 captures an LR projection image at each scanning time. Each LR projection image sampled by the light detector 160 can be used to display a 2D, LR projection image. In embodiments with a color light detector 160, the LR projection image may be a color image.

In embodiments with a monochromatic light detector 160, the LR projection image may be a black and white image.

Each sequence of sub-pixel shifted LR projection images can refer to n LR projection images sampled at n sampling times where neighboring projection images in time are separated by less than a pixel size (i.e. sub-pixel shift). During a scanning cycle, n LR projection images ($I_1, \ldots, I_n$) may be captured at n sequential sampling times ($t_1, \ldots t_n$). Any suitable number, n (e.g., 1, 3, 5, 10, 100, etc.) of LR projection images may be captured during a scanning cycle. Also, any suitable number (e.g., 1, 3, 5, 10, 100, etc.) of sequences of sub-pixel shifted LR projection images may be captured by the light detector 160 during a scanning cycle. If multiple sequences are captured, the sequences can include different groups of LR projection images or the sequences can overlap sharing one or more LR projection images. In one example, 9 LR projection images ($I_1, I_2, I_3, I_4, I_5, I_6, I_7, I_8, I_9$) may be captured at 9 sequential sampling times ($t_1, t_2, t_3, t_4, t_5, t_6, t_7, t_8, t_9$). In an overlapping case of the above example, sequences could be: 1) $I_1, I_2, I_6$, and $I_8$, and, 2) $I_6, I_7, I_8$, and $I_9$. In a non-overlapping case, sequences could be: 1) $I_1, I_2, I_3$, and $I_4$, and 2) $I_5, I_6, I_7$, and $I_8$. In others examples, a sequence of sub-pixel shifted LR projection images may be based on non-sequential sampling times. For example, 9 LR projection images ($I_1, I_2, I_3, I_4, I_5, I_6, I_7, I_8, I_9$) may be captured at 9 sequential sampling times ($t_1, t_2, t_3, t_4, t_5, t_6, t_7, t_8, t_9$) and the sequence of projection images may be ($I_6, I_2, I_9, I_1$).

In embodiments, the light detector 160 may capture an LR projection image at each scanning time during a scanning cycle. For example, a light detector 160 may capture an LR projection image associated with each scanning location in the scanning pattern shown in FIG. 4(b). In this example, the light detector 160 may capture a projection image at each scanning time as the light element 117 moves through each row sequentially of the two-dimensional array of scanning locations in the scanning pattern. If scanning locations in each row are associated with sub-pixel shifted projections 170, the light detector 160 may capture 15 sequences of sub-pixel shifted projection images during the scanning cycle. In this case, each sequence is associated with a row of scanning locations in the scanning pattern.

A motion vector can refer to the translational motion of projection images in a sequence of LR projection images, collectively termed the motion vector of the sequence of LR projection images. The motion vector is based on the amount of shifting of the projection images at a plane. A motion vector of a sequence of sub-pixel shifted LR projection images can be calculated from the associated projection images captured by the light detector 160. The motion vector may be calculated at any plane of interest. For example, the motion vector can be determined at the plane at the sensing surface 162. In this example, the motion vector is determined in terms of the local x'-axis and y'-axis at the sensing surface 162 of the light detector 160. As another example, the motion vector can be calculated at other planes through an object 152 being examined. The planes through the object 152 may be parallel to the plane of the sensing surface 162 in some cases.

In embodiments, an HR image of a specimen 150 can be constructed using a suitable super resolution (SR) algorithm based on data associated with a sequence of sub-pixel shifted LR projection images and a motion vector of the sub-pixel shifted LR projections in the sequence. An example of image resolution obtainable by embodiments of the SPLM system 10 may be about 0.66 micron.

An SR algorithm can refer to an image processing technique that constructs a HR image (e.g., sub-pixel resolution image) from a sequence of sub-pixel shifted LR projection images. Any suitable SR algorithm can be used by embodiments of the SPLM system 10. An example of a suitable SR algorithm is a shift-and-add pixel SR algorithm. Some examples of suitable SR algorithms can be found in Lange, D., Storment, C. W., Conley, C. A., and Kovacs, G. T. A., "*A microfluidic shadow imaging system for the study of the nematode Caenorhabditis elegans in space*," Sensors and Actuators B Chemical, Vol. 107, pp. 904-914 (2005) ("Lange"), Wei, L., Knoll, T., and Thielecke, H., "*On-chip integrated lensless microscopy module for optical monitoring of adherent growing mammalian cells*," Engineering in Medicine and Biology Society (EMBC), 2010 Annual International Conference of the IEEE, pp. 1012-1015 (2010) ("Wei"), Milanfar, P., "*Super-Resolution Imaging*", CRC Press, (2010) ("Milanfar"), and Hardie, R., Barnard, K., and Armstrong, E., "*Joint MAP registration and high-resolution image estimation using a sequence of undersampled images*," IEEE Transactions on Image Processing 6, pp. 1621-1633 (1997) ("Hardie"), which are hereby incorporated by reference in their entirety for all purposes. An example of a suitable super algorithm is the general pixel super resolution model and solution described in Section II.

The SPLM system 10 of FIG. 1 also includes a host computer 200 communicatively coupled to the light detector 160. The host computer 200 comprises a second processor 210 (e.g., microprocessor), a second CRM 220, and an image display 230. The image display 230 and the second CRM 220 are communicatively coupled to the second processor 210. Alternatively, the host computer 200 can be a separate device from the SPLM system 10. The host computer 200 can be any suitable computing device (e.g., smartphone, laptop, tablet, etc.)

The second processor 230 executes code stored on the second CRM 220 to perform some of the functions of SPLM 10 such as, for example: interpreting data from one or more sequences of sub-pixel shifted LR projection images captured and communicated in one or more signals from the light detector 160, determining a motion vector of a sequence of sub-pixel shifted projections, constructing a 2D HR image from data associated with a sequence of sub-pixel shifted LR projection images, constructing a 3D HR image from data associated with a sequence of sub-pixel shifted LR projection images, displaying one or more HR images on the image display 230, etc.

The second processor 210 can receive one or more signals with light data and other data from the light detector 160. For example, the processor 210 can receive one or more signals with light data associated with one or more sequences of sub-pixel shifted LR projection images sampled at a corresponding sequence of n scanning times ($t_1, t_2, t_3, \ldots t_n$). The second processor 210 can also determine a motion vector based on the sequence of sub-pixel shifted LR projection images. The second processor 210 can also construct HR images and associated image data based the determined motion vector and data associated with at least one sequence of sub-pixel shifted LR projection images. In some cases, the constructed HR image of the object 150 is a black and white 2D/3D image. In other cases, the constructed HR image of the object 150 is a color 2D/3D image.

In one embodiment, a HR color image can be generated by using different wavelengths of illumination 118 at different sampling times to generate a multiple sequences of sub-pixel shifted LR projection images at a light detector 160. Each sequence is associated with a different wavelength. The second processor 210 can generate HR color image and associated image data based on the different sequences associated with different wavelengths. For example, three wavelengths of light (e.g., wavelengths associated with red, green, blue (RGB) colors) can be sequentially generated by a light element 117 to generate three sequences of sub-pixel shifted projection images associated with three wavelengths of light. The processor 210 can combine the image data from the sequences associated with the different wavelengths to generate multi-wavelength or color image data (e.g., RGB color image data). The multi-wavelength or color HR image data can be used to generate a multi-wavelength or color HR image on the image display 230.

The second CRM (e.g., memory) 220 can store code for performing some functions of the SPLM system 10. The code is executable by the second processor 210. For example, the second CRM 220 of embodiments may include: a) code with a SR algorithm, b) code with a tomography algorithm, c) code for interpreting light data received in one or more signals from the light detector 160, d) code for generating a 3D HR image, e) code for constructing a color sub-pixel image, f) code for displaying SR two-dimensional and/or three-dimensional images, g) and/or any other suitable code for performing functions of the SPLM system 10. The second CRM 220 may also include code for performing any of the signal processing or other software-related functions that may be created by those of ordinary skill in the art. The code may be in any suitable programming language including C, C++, Pascal, etc.

The SPLM system 10 also includes an image display 230 communicatively to the processor 210 to receive data and provide output such as HR images to a user of the SPLM system 10. Any suitable display may be used. For example, the image display 230 may be a color display or a black and white display. In addition, the image display 230 may be a two-dimensional display or a three-dimensional display. In one embodiment, the image display 230 may be capable of displaying multiple views of an object 150.

Modifications, additions, or omissions may be made to SPLM system 10 or the SPLM device 100 without departing from the scope of the disclosure. In addition, the components of SPLM 10 or SPLM device 100 may be integrated or separated according to particular needs. For example, the second processor 210 may be integrated into the light detector 160 so that the light detector 160 performs one or more of the functions of the second processor 160 in some embodiments. As another example, the second processor 160, second CRM 220, and image display 230 may be components of a computer separate from the SPLM system 10 and in communication with the SPLM system 10. As another example, the second processor 160, second CRM 220, and/or image display 230 may be integrated into parts of the SPLM device 100. For example, the image display 230 may be part of the illumination display 116, the first processor 112 and second processor 210 may be integrated into a single processor, and/or the first CRM 114 and second CRM 220 may be integrated into a single CRM.

II. Imaging Method Used by SPLM and e-Petri

A. Principle and Resolution

Nyquist criterion considerations dictate that the raw projection (shadow) image resolution from an image sensor (e.g., CMOS image sensor) may be no better than two times the pixel size. The SPLM and e-Petri systems of embodiments of embodiments use a high sampling rate in the time domain to offset the sub-Nyquist rate sampling in the spatial domain of the projection images, combining work done in super resolution imaging with advanced sensor (e.g., CMOS) technology to produce a low cost, HR microscopy device with significant resolution enhancement.

The SPLM and e-Petri systems of embodiments include a thin transparent layer 165 between the light detector 160 and the object 152 being imaged. The transparent layer 165 separates the objects 152 (e.g., cells) from the actual light sensitive region of the light detector 160 (e.g., sensor chip). During scanning, the scanning illumination source 110 shifts/scans or otherwise moves a light element 117 to different positions to provide illumination 118 (e.g., incoherent light) from different illumination angles above the specimen 150. The light detector 160 acquires one or more sequences of LR projection images. With the movement of the illumination 118, the projection image shifts across the light detecting elements 166 (e.g., sensor pixels), as shown in FIG. 3. The amount of shadow shift is proportional to the thickness of the transparent layer 165 and the tilt/shift extent of the light element 117. As long as the shift between each raw projection image in each sequence of LR projection images is smaller than the physical size of the light detecting element (e.g., pixel size), the information from multiple sub-pixel-shifted LR shadow images can be used to create a single HR (sub-pixel resolution) image with a suitable super-resolution algorithm.

In previous super resolution microscanning systems, a specimen was mounted to a stage and the stage was scanned in sub-pixel increments. In this prior approach, the position of the stage needed to be accurately controlled in precise sub-pixel steps. Typically, controllers and actuators were used to control the required precise position of the stage. High precision meant high cost of setup and alignment was required by these systems.

In a previous super resolution optofluidic system, optofluidics are incorporated to generate HR images from LR projection images in a high throughput manner. In this system, an optofluidic sample-delivery scheme is employed to capture a sequence of images of the sample translating across a CMOS imaging sensor (pixel) array. The system uses super-resolution processing techniques to achieve HR images from the sequences of LR projection images as described in U.S. patent application Ser. No. 13/069,651, which is hereby incorporated by reference in its entirety for all purposes, and described in Zheng. This method relies upon capturing a sequence of LR projection images of objects (e.g., cells) as they flow through a fluid channel, across a light detector (e.g., CMOS imaging sensor array). However, imaging in this system requires fluidic (e.g., microfluidic) flow of specimens across a scanning area. Adherent, confluent, or contiguously arranged specimens are simply incompatible with imaging in a fluidic mode. For example, in order to make an object flow across the fluid channel, an object cannot attach to the surface of image pixel (i.e. there is distance between the object and the image pixel). Such a distance results in a blurry image of the object. In addition, the field of view can be limited by the geometry of the fluid channel.

The SPLM and e-Petri systems and devices use a scanning illumination source 110 to position a light element 117 over the specimen 150. In this approach, there may be no need for precise alignment. The scanning illumination source 110 is located at a larger distance from the sensing surface 162 than the object 152. Thus, shifts of the light element 117 correspond to smaller shifts of the projections 170 on the sensing surface 162. The scanning illumination source 110 can control the sub-pixel shifts of the projections at the sensing surface 162 directly with more controllable larger shifts of the light element 117 at the scanning illumination source 110. In this way, the scanning illumination source 110 can easily and accurately keep the projection shifts at sub-pixel values than previous systems such as microscanning systems, optofluidic systems, etc. Moreover, without the need of mechanical scanning or microfluidic flow, the speed of scanning can be much faster. The scanning illumination source 110 can scan light at speeds up to the range of kHz. This is two orders of magnitude higher than prior mechanical microscanning schemes. In addition, the cost of the devices can be much lower since it uses a scanning illumination source 110 such as a LED screen or LED matrix.

Figure 5:
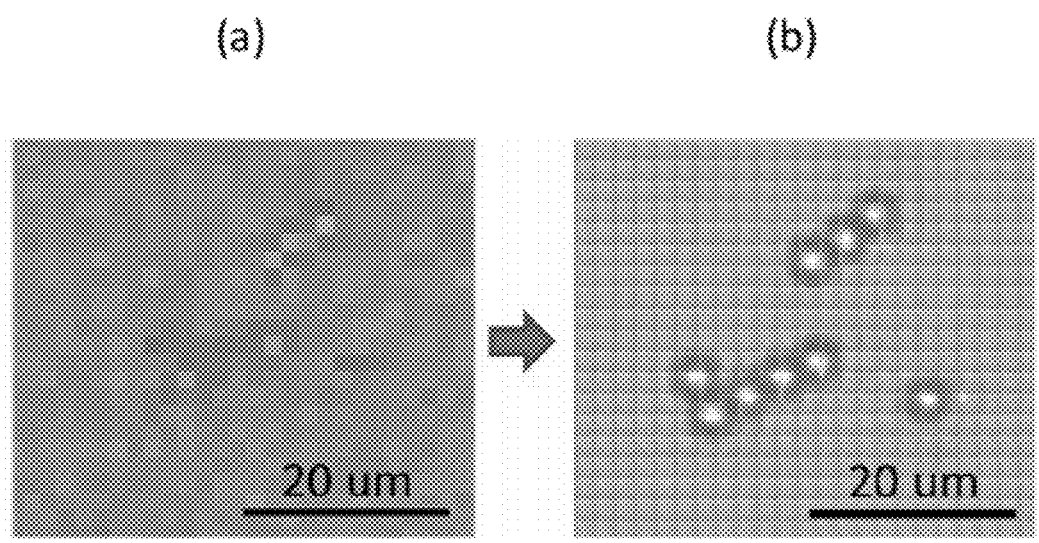
FIG. 5(a) is an LR projection image captured by a light detector of an SPLM system or an e-Petri system at a single sampling time, according to embodiments of the invention.
FIG. 5(b) is an HR image reconstructed by the SPLM system or an e-Petri system, according to embodiments of the invention.

FIG. 5(a) is a projection image captured by a light detector 160 of an SPLM system 10 or an e-Petri system at a single sampling time, according to embodiments of the invention. In this example, the specimen 150 being imaged includes a group of 3 μm microspheres. FIG. 5(b) is an HR image reconstructed by the SPLM system 10 or the e-Petri system, according to embodiments of the invention. The system reconstructed the HR image based on data from a sequence of sub-pixel shifted LR projection images including the LR projection image shown in FIG. 5(a).

Figure 6:
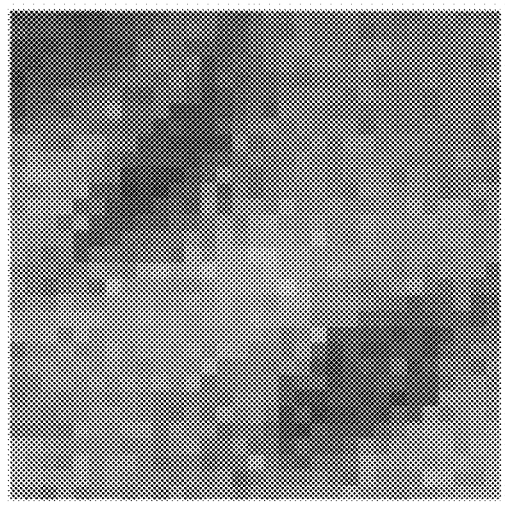
FIG. 6(a) is an LR projection image of a portion of a HeLa cell specimen captured by a light detector of an SPLM system or an e-Petri system at a single sampling time, according to embodiments of the invention.
FIG. 6(b) is an HR image reconstructed by the SPLM system or an e-Petri system, according to embodiments of the invention.
Figure 6:
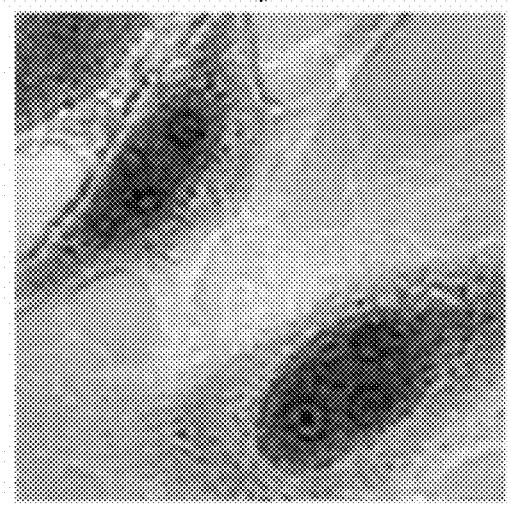

FIG. 6(a) is an LR projection image of a portion of a HeLa cell specimen captured by a light detector 160 of an SPLM system 10 at a single sampling time, according to embodiments of the invention. FIG. 6(b) is an HR image reconstructed by the SPLM system 10 or the e-Petri system, according to embodiments of the invention. The SPLM system 10 or the e-Petri system reconstructed the HR image based on data from a sequence of 225 sub-pixel shifted LR projection images including the LR projection image shown in FIG. 6(a).

Figure 7:
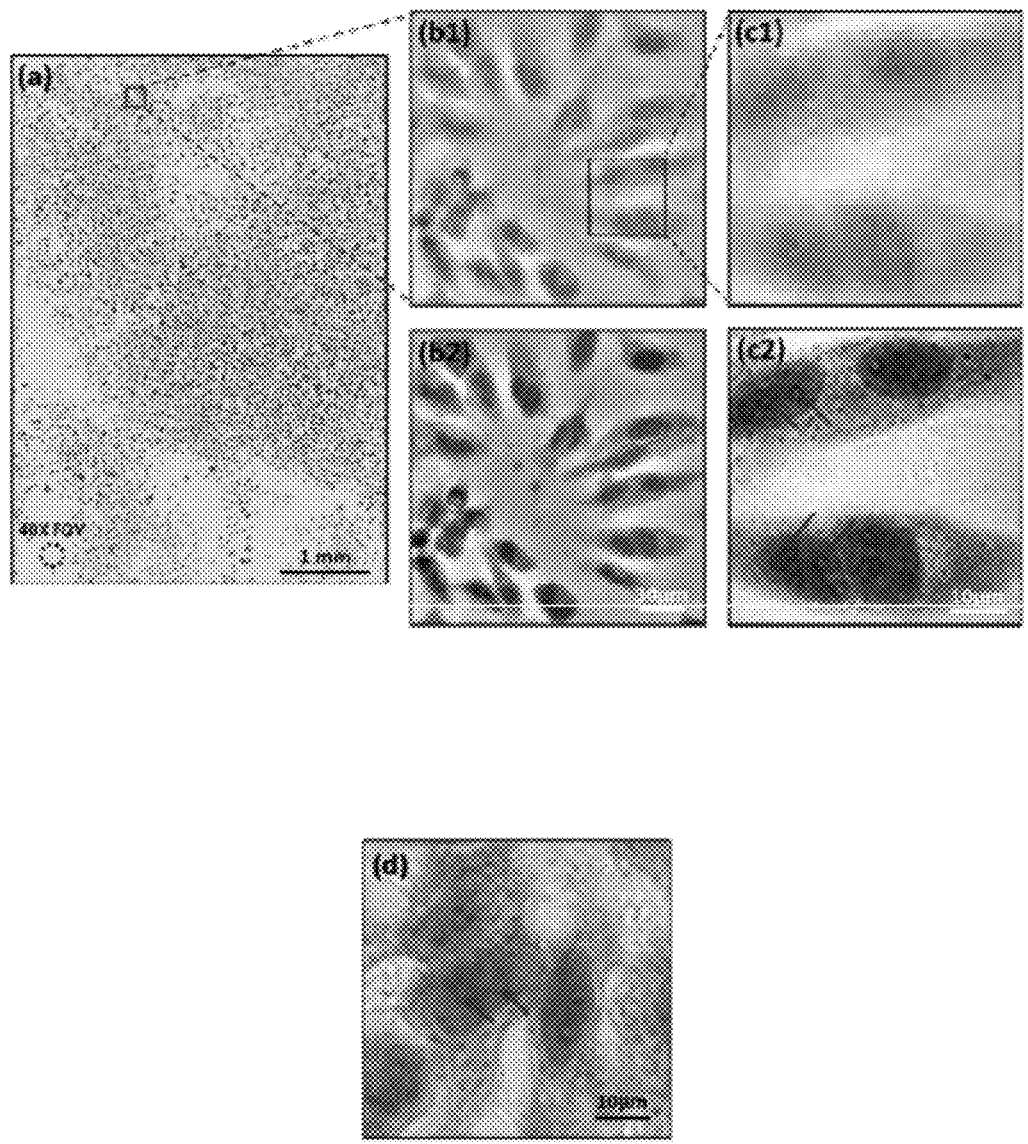
FIG. 7(b1) is an LR projection image from a small region of FIG. 7(a), captured by the light detector of an SPLM system or an e-Petri system, according to embodiments of the invention.

FIG. 7(a) is a large field of view color HR image of a confluent HeLa cell specimen 150 constructed by an SPLM system 10 or an e-Petri system, according to embodiments of the invention. The specimen 150 was stained with Giemsa. During reconstruction, each pixel at the LR projection image level (2.2 μm) was enhanced into a 13×13 pixel block in the reconstructed HR image. The color HR image contains about $8.45 \times 10^8$ pixels. The sensing area 164 (image area) was 6 mm×4 mm. A 15×15 array of scanning locations for each color illumination 118 was used. FIG. 7(b1) is an LR projection image from a small region of FIG. 7(a) and FIG. 7(c1) is an LR projection image from a small region of FIG. 7(b1), captured by the light detector 160 of an SPLM system 10 or an e-Petri system, according to embodiments of the invention. FIG. 7(b2) is a reconstructed HR image from the same small region of FIG. 7(a) and FIG. 7(c2) is a reconstructed HR image from a small region of FIG. 7(b2) constructed by an SPLM system 10 or an e-Petri system, according to embodiments of the invention. FIG. 7(d) is a conventional microscopy image of similar cells using a microscope with 40×, NA=0.66 objective lens. From the reconstructed HR images in FIGS. 7(b2) and 7(c2), organelles within the HeLa cell can be discerned such as multiple nuclear granules (indicated by red arrows), and the nucleus. The reconstructed HR images also closely corresponded to conventional microscopy images acquired from similar cells.

Figure 8:
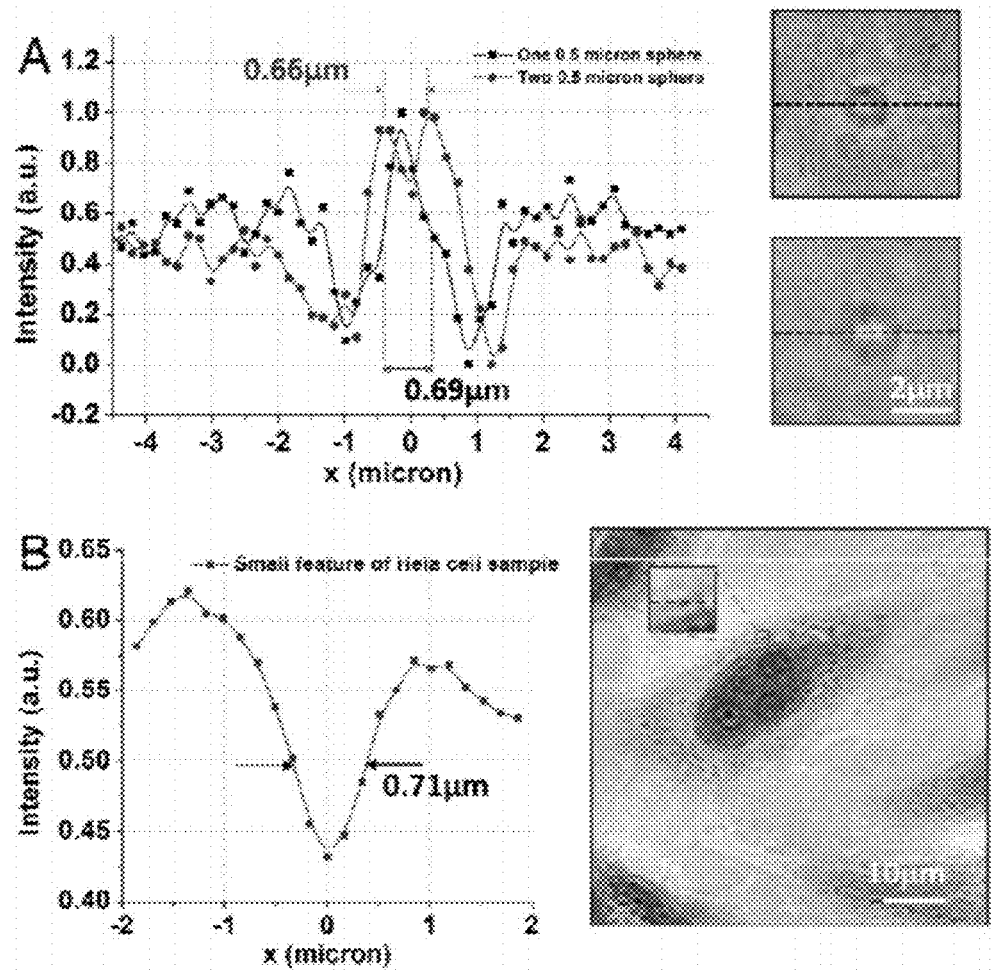
FIG. 8(a) is an HR image of a specimen having 500 nm microspheres (Polysciences) as constructed by an SPLM system or an e-Petri system, according to embodiments of the invention.
FIG. 8(b) is an HR image of a magnified small feature of the stained HeLa cell specimen of FIG. 7 as constructed by an SPLM system or an e-Petri system, according to embodiments of the invention.

FIG. 8(a) is an HR image of a specimen 150 having 500 nm microspheres (Polysciences) as constructed by an SPLM system 10 or an e-Petri system, according to embodiments of the invention. The imaging process used to construct the HR image was identical the one used to construct the HR images in FIG. 7. For a single 500 nm microsphere, the bright center of the microsphere was clearly resolved as shown in FIG. 8(a), with the full-width at half maximum (FWHM) of 690 nm. FIG. 8(b) is an HR image of a magnified small feature of the stained HeLa cell specimen 150 of FIG. 7 as constructed by an SPLM system 10 or an e-Petri system, according to embodiments of the invention.

Since microscopy resolution may be defined in some cases based on a given microscope's ability to resolve two closely spaced feature points, the case of two closely spaced microspheres can be analyzed to establish a resolution of an SPLM system 10 or an e-Petri system of embodiments. FIG. 8(a) shows the reconstructed images of two closely packed 500 nm microspheres with center-to-center distance of 660 nm. The data trace in FIG. 8(a) shows a valley between the two peaks and, thus, establishes that the resolution may be 660 nm or better in some embodiments. To further verify this point, FIG. 8(b) shows the magnified small feature of the stained HeLa cell specimen of FIG. 7 and the FWHM of this feature was estimated to be about 710 nm.

B. Concept

In embodiments such as the example shown in FIG. 1, the specimen 150 is placed on a specimen surface 140 located slightly above the active sensing area 164 of the sensing surface 162. The illuminating display 116 (e.g., a monochromatic or color LCD) of a scanning illumination device 110 (e.g., mobile communication device) is located at a distance, d, (e.g., about 5-10 mm) away from the sensing surface 162. A light element 117 (e.g., one or more light emitting components (e.g., pixels)) of the illuminating display 117 provide illumination 118 (e.g., incoherent light). The illumination 118 generates a projection 170 (shadow) on the light detector 162. The light detector 160 can capture an LR projection image. This LR projection image is the best achievable given the size limitations (e.g., pixel size limitations) of the light detecting elements 166 (as shown in FIG. 2), but "low resolution" in that features sizes of the specimen 150 may be much smaller than the size (e.g., pixel size) of the light detecting element 166.

In embodiments, to improve the resolution, a sequence of sub-pixel shifted LR projection images is captured, for which light emitting components (e.g., pixels) on the illuminating display 116 (e.g., an LCD) provide illumination 118. Each of these LR projection images is a sub-pixel shifted projection image of the specimen 150. The sequence of sub-pixel shifted LR projection images can be based on the scanning locations of the light element 117 during a scanning cycle. For a known sub-pixel displacement, these sub-pixel shifted LR projection images can be used to create a HR (e.g., sub-pixel resolution) 2D image using pixel super-resolution techniques. This HR image can further be deconvolved with the point spread function of the pixel and optical system to recover a focused image of the specimen. SPLM system 10 e-Petri systems made possible precise scanning of the light element 117 in conjunction with pixel super-resolution image processing techniques.

Furthermore, this concept of imaging can be extended beyond two dimensions. Computed tomography using different incident angles of light to generate multiple projections can be used to create a three dimensional reconstruction of the object. An example of using tomography to generate a 3D image can be found in Miao, J. R. R. Qin, Tourovskaia, Anna, Meyer, Michael G., Neumann, Thomas, Nelson, Alan C., and Seibel, Eric J., "*Dual-modal three-dimensional imaging of single cells with isometric high resolution using an optical projection tomography microscope*," J. Biomed., Opt., Vol. 14, 064034 (Dec. 21, 2009), which is hereby incorporated by reference in its entirety for all purposes. In our scheme, the shifting light element 117 (e.g., sets of pixels) across the illuminating display 116 (e.g. LCD) can provide different angles of incident light necessary for 3D imaging.

C. Operating Principles

In one operation, the specimen 150 is placed slightly (e.g., in the range of several hundred nanometers to microns) above the sensing surface 162 (e.g., outer surface) of the light detector 160 (e.g., CMOS imaging sensor array). Individuals or small sets of light emitting components 166 (e.g., pixels) on the illuminating display (e.g., an LCD) are illuminated in succession to illuminate the specimen 150 at distance (e.g. 5 mm-10 mm) away, allowing the light detector 160 to record one or more sequences of sub-pixel-shifted LR projection images, which are "pixilated." One or more sequences of sub-pixel shifted LR projection images can be processed using super resolution techniques to combine many LR projection images to create a smaller sequence of HR images. An example of a super resolution technique can be found in Richard, L. M., Shultz, R., Stevenson, Robert L., "*Subpixel motion estimation for superresolution image sequence enhancement*," Journal of Visual Communication and Image Representation (1998), which is hereby incorporated by reference in its entirety for all purposes.

Super resolution or super resolution techniques refer to a general name for the many promising new techniques for imaging processing that can involve creating a single HR image from a sequence of lower resolution images. Some super resolution techniques can be found in Park, Sung Cheol, Park, and Min Kyu, Kang, Moon Gi, "*Super-resolution image reconstruction: a technical overview*," IEEE Signal Processing Magazine, pp. 21-36 (May 2003) ("Park"), which is hereby incorporated by reference in its entirety for all purposes. The general principle involves taking a sequence of LR projection images in which the target is sampled at below the Nyquist rate, but for which subsequent frames involve a slight sub-pixel translational shift. This principle can be found in Russell, K. J. B., Hardie, C., Bognar, John G., Armstrong, and Ernest E., Watson, Edward A., "*High resolution image reconstruction from a sequence of rotated and translated frames and its application to an infrared imaging system*," Optical Engineering (1997), which is hereby incorporated by reference in its entirety for all purposes. If this translational shift is known, then a system of matrix equations can be established from the lower resolution sequence to solve for sub-pixel values to create a single HR image. In general, the original HR image can theoretically be recovered even from a significantly decimated, blurred, translated, and rotated lower resolution image sequence; resolution is limited only by the diffraction limit and noise, as described in Park.

D. Flowchart of Exemplary Method of Operation

Figure 9:
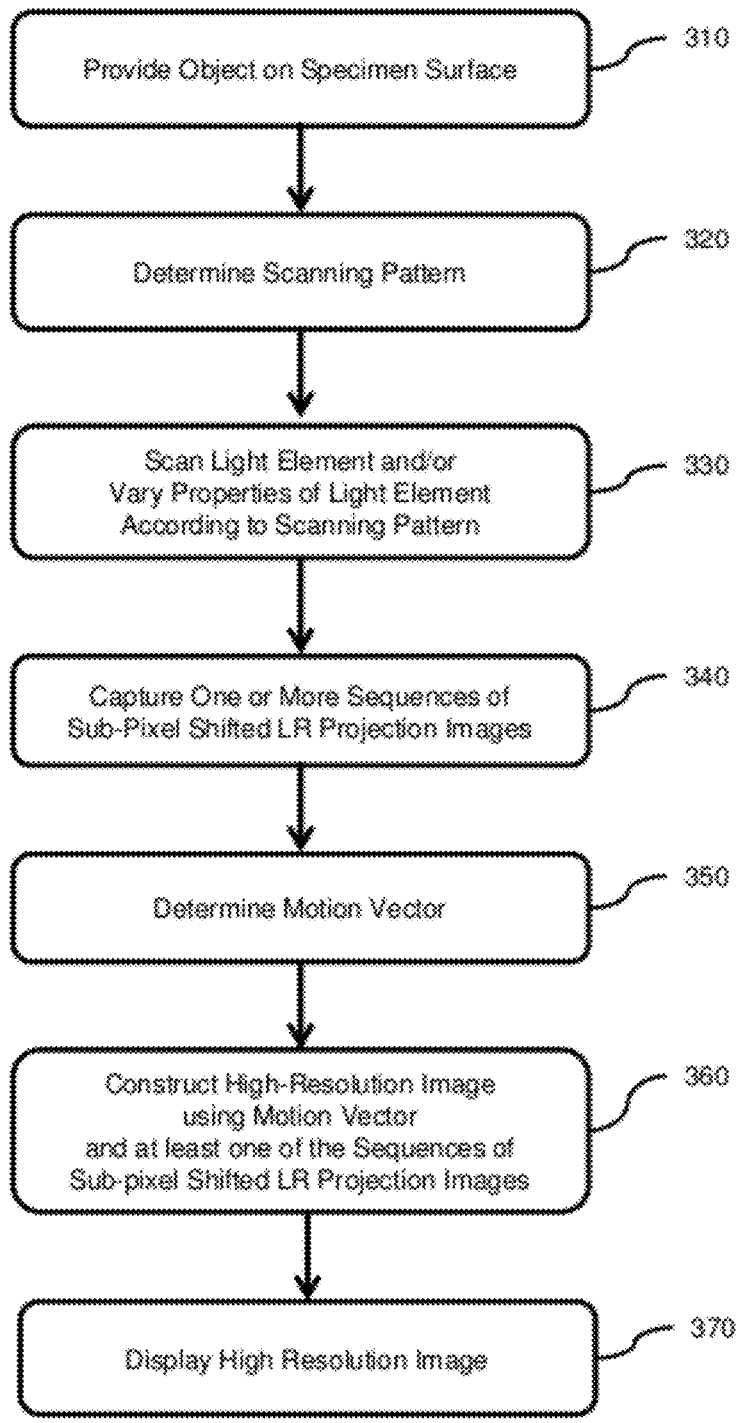
FIG. 9 is a flow chart of an exemplary operation of an SPLM device or an e-Petri device, according to embodiments of the invention.

FIG. 9 is a flow chart of an exemplary operation of an SPLM device 100 or an e-Petri device, according to embodiments of the invention. The SPLM device 100 and e-Petri device include a scanning illumination source 110 for shifting or otherwise positioning a light element 117 to provide illumination from different illumination angles to an object 152 being imaged. Although imaging of an object 152 is described in this section, the method can be used to image a specimen 150 having any suitable number of objects 152. The SPLM device 100 and the e-Petri device also include a specimen surface 140, a light detector 160 having a sensing surface 162, a thin transparent layer 165 between the sensing surface 162 and the specimen surface 140, and a processor (first processor 112 and/or second processor 210). The scanning illumination source 110 is located at a distance, d, from the sensing surface 162. This exemplary operation includes an imaging run having a single scanning (illumination) cycle. Other embodiments may have an imaging run with multiple scanning (illumination) cycles.

In step 310, the object 152 is placed onto the specimen surface 140 of the SPLM 100 or the e-Petri device. The object 152 may be located proximal a sensing area 164 of the sensing surface 162 at the active layer of the light detector 160.

In step 320, the processor determines a scanning pattern. An example of a scanning pattern is shown in FIGS. 4(a) and 4(b). The scanning pattern may include scanning locations at different times during a scanning cycle and properties (e.g., wavelength(s) of light used, the size and shape of the light element, the intensity(ies) of the light element, etc.) of the light element 117 at different scanning locations, the amount of sub-pixel shift desired between subsequent LR projection images, the total number of LR projection images desired in the scan and/or in the sequence of LR projection images, the total number of HR images desired in an imaging run, and other suitable information related to the operation of the SPLM system 10 or e-Petri system. The processor may retrieve a predetermined scanning pattern from the CRM (first CRM 114 or second CRM 220) or the processor may determine a scanning pattern based on input from a user of the SPLM system 10 or the e-Petri system. For example, the user may provide information such as properties of the light element, the amount of sub-pixel shift desired between subsequent LR projection images, the total number of HR images desired, and other suitable input.

The scanning locations in the scanning pattern can be determined to generate a sequence of sub-pixel shifted projections at the sensing surface 162. The shift of a projection 170 is proportional to the thickness of the transparent layer 165 and the tilt/shift extent (i.e. distance or illumination angle change between neighboring scanning locations). The amount of translation of the light element 170 between neighboring scanning positions that will result in sub-pixel shifting of the projections 170 can be determined based on the thickness of the transparent layer 165 and the required sub-pixel shift value. The scanning locations in the scanning pattern can be based on the amount of translation of the light element 170 between neighboring scanning positions.

In step 330, the scanning illumination source 110 scans or otherwise positions the light element 117 and modifies the properties of the light element 117 according to the scanning pattern. In one embodiment, the scanning illumination source 110 (e.g., smartphone) has an illuminating display 116 in the form of an LCD. In this example, the scanning pattern may include a two-dimensional array of scanning positions and the scanning times associated with the scanning positions. During scanning the light element 117 may be a set of light emitting components (e.g. pixels) in the LCD which are sequentially illuminated to shift the light element 117 through each row/column of the two-dimensional array of scanning locations. The properties of the light element 117 may vary at different locations. For example, the size (number of light emitting components) of the light element 117 may vary to maintain approximately the same intensity level at a location at the sensing surface 162.

In one embodiment, the light element 117 can provide illumination 118 of n different wavelengths $\lambda_1, \ldots, \lambda_n$ at different times during a scanning cycle to obtain a sequence of projection images for each wavelength. Any suitable number of wavelengths may be used (e.g., n=1, 2, 3, 4, 5, ..., 20). In one embodiment, the light element 117 may provide illumination 118 of three wavelengths $\lambda_1, \lambda_2,$ and $\lambda_3$ corresponding to red, green, blue colors at different sampling times. In some cases, the illumination 118 from one scanning location to a neighboring scanning location may have different wavelengths. In other cases, the illumination 118 may have a first wavelength during a first series of scanning positions, and then provide illumination 118 of a second wavelength during a second series of scanning positions, and so forth until n sequences of projection images corresponding to n different wavelengths have been captured.

In step 340, the light detector 160 captures one or more sequences of sub-pixel shifted LR projection images of the object 152 as the light element 117 translates to different scanning positions. The light detector 160 captures an LR projection image for each scanning location. Any suitable number of images (e.g., 3, 5, 10, 50, 100, etc.) may be in each sequence. In one example, the scanning locations may be in the form of a two-dimensional array of scanning positions, where each row/column of scanning positions can generate a row of sub-pixel shifted projections 170. In this example, a sequence of sub-pixel LR projection images may be captured as the light element 117 shifts across each row/column in the two-dimensional array of scanning positions.

In step 350, the processor uses a suitable method to determine the motion vector of the projections 170 at the sensing surface 162. In some cases, the processor may also determine motion vectors of the projections 170 at other parallel planes through the object 152. Any suitable method of determining a motion vector can be used. In one example, the motion vector of the projections at the sensing surface 162 may be determined based on the distance between neighboring scanning positions and the thickness of the transparent layer 165. In another example, the motion vector of the projections at planes parallel to the sensing surface 162 may be determined based on the distance between neighboring scanning positions and the thickness of the transparent layer 165 and the distance between the plane and the sensing surface 162.

In step 360, the processor uses an appropriate SR algorithm to construct a HR image of the object 152 from data from a sequence of sub-pixel shifted LR projection images and corresponding motion vector(s). For example, the processor can construct a 2D image of the object 152 at a plane through the object 152 by using a motion vector at that plane. In one example, the processor can generate a 3D HR image by stacking the 2D HR images constructed based on motion vectors at different planes. If the light detector 160 is a monochromatic light detector, the HR image will be a monochromatic HR image (black and white HR image). If the light detector 160 is a color light detector (e.g., a color CMOS imaging sensor), the image resulting from this reconstruction is a color image.

In one embodiment, a shift-and-add SR algorithm may be used to construct an HR image with data from a sequence of sub-pixel shifted LR projection images. In this embodiment, an HR image grid is formed with an enhancement factor of n, where each n-by-n pixel area of the HR image grid corresponds to a 1-by-1 pixel area of the LR frame grid. Then, the HR image grid is filled with the corresponding pixel values from the sequence of sub-pixel shifted LR projection images. The mapping of the pixels within the n-by-n grid is determined from the known, estimated sub-pixel shift of each image from the motion vector determined. In other words, each LR projection image is shifted by the relative sub-pixel shift of the object 152 from its original position and then added together to form a HR image.

Finally, deblurring using the wiener deconvolution method may be used to remove blurring and noise in the final HR image.

In one embodiment, the light element 117 can provide illumination 118 of n different wavelengths $\lambda_1, \ldots, \lambda_n$ at different times during a scanning cycle to obtain a sequence of projection images for each wavelength. In this embodiment, the processor can use an appropriate SR algorithm to reconstruct an HR image for each wavelength or color based on each sequence of sub-pixel shifted LR projection images and the motion vector. The SPLM device 100 or e-Petri device can combine the HR images of different wavelengths or colors to obtain a computed color HR image. For example, an SPLM device 100 or e-Petri device using RGB illumination from can be used to construct a computed color (RGB) HR image.

In step 370, the processor can display one or more HR images to a suitable image display 230 (e.g., two-dimensional display (color or monochromatic), three-dimensional display (color or monochromatic)). Any suitable image generated by the SPLM device 10 or e-Petri device can be displayed. Some examples of suitable images include: LR projection images, 2D black and white HR images, 2D color HR images, 3D black and white HR images, and/or 3D color HR images.

E. A Super Resolution Model and Solution

Embodiments of the SPLM system 10 and the e-Petri system use a SR algorithm to reconstruct an HR image. One example of a SR algorithm is the general pixel super resolution model and solution described in this Section. This general pixel super resolution model and solution has a simple, fast and non-iterative method that preserves the estimation optimality in the Maximum-Likelihood sense. Some details of this super-resolution model and solution can be found in Hardie, Elad, M., and Hel-Or, Y., "*A fast super-resolution reconstruction algorithm for pure translational motion and common space-invariant blur*," IEEE Transactions on Image Processing, Vol. 10, pp. 1187-1193 (2001) ("Elad"), Farsiu, Sina, et al., *Fast and robust multiframe super resolution*," IEEE Trans Image Process, vol. 13, pp. 1327-1344 (2004), and Farsiu S, et al., "*Multiframe demosaicing and super-resolution of color images*," IEEE Trans Image Process, vol. 15, pp. 141-159 (2006), which are hereby incorporated by reference in their entirety for all purposes.

In an scanning cycle, a sequence of N captured LR projection images, $Y_k$ (k=1, 2 ... N) can be used to reconstruct an improved HR image, X. The images may be represented by lexicographically ordered column vectors. The LR projection image can be modeled by the following equation:

$$Y_k = DHF_k X + V_k (k=1,2 \ldots N) \quad \text{(Eqn. 1)}$$

The matrix $F_k$ stands for the sub-pixel shift operation for the image X. The matrix H is the pixel transfer function of the light detector 160 (e.g., CMOS image sensor). The matrix D stands for the decimation operation, representing the reduction of the number of observed pixels in the measured images. $V_k$ represents Gaussian additive measurement noise with zeros mean and auto-correlation matrix: $W_k = E\{V_k V_k^T\}$.

The Maximum-Likelihood estimation of X can be described as the following expression:

$$\hat{X} = \text{Arg}_X \text{Min}\left\{\sum_{k=1}^{N} (Y_k - DHF_k X)^T W_k^{-1} (Y_k - DHF_k X)\right\} \quad \text{(Eqn. 2)}$$

And the closed-from solution for $\hat{X}$ is shown to be:

$$\hat{X} = H^{-1} R^{-1} P \quad \text{(Eqn. 3)}$$

where, $R = \sum_{k=1}^{N} F_k^T D^T D F_k$, $P = \sum_{k=1}^{N} F_k^T D^T Y_k$

R can be a diagonal matrix and the computation complexity of this approach may be: O(n*log(n)).

F. Different Schemes for the SPLM and e-Petri Systems and Devices

Scheme 1-2D Monochromatic Imaging

In a first scheme, SPLM systems 10 or e-Petri systems of embodiments may be designed to generate 2D monochromatic HR images of a specimen 150 using a suitable SR algorithm based on a sequence of LR projection images and a motion vector. For this case, there is only the known translational shift and space invariant point spread function of the system, H, which is also known. Hence, more effective and computationally efficient super resolution techniques can be applied, such as the following as proposed in Elad. For an original HR image, X, of a specimen 150 that is the desired output of the SPLM system 10 or the e-Petri system, a lower resolution image sequence of the sample:

$$Y_k = DHF_k X + V_k (k=1,2 \ldots N) \quad \text{(Eqn. 4)}$$

is obtained, where $F_k$ is the translational shift, H is the point spread function of the optical system, $D_k$ is the downsampling of the original LR projection image and $V_k$ is white noise with auto-correlation: $W_k = E\{V_k V_k^T\}$. Hence, by minimizing the least square error, the computed HR image $\hat{X}$ is obtained from a sequence of N LR projection images as follows:

$$\hat{X} = \text{Arg}_X \text{Min}\left\{\sum_{k=1}^{N} (Y_k - D_k HF_k X)^T W_k^{-1} (Y_k - D_k HF_k X)\right\} \quad \text{(Eqn. 5)}$$

This optimization can be done computationally with iterative methods described in Elad. The end result of this optimization can be an in-focus HR image or sequence of HR images of the specimen generated from the original LR projection images captured by the light detector 160. (e.g., CMOS image sensor).

In embodiments, an SPLM system 10 or an e-Petri system may include an illuminating display 116 in the form of a pixel array (e.g., rectangular pixel array). For example, the illuminating display 116 may be a rectangular pixel array of an LCD. In these embodiments, the sub-pixel shifts between subsequent LR projection images of a sequence may be related by a characteristic sub-pixel spacing, α, related to the illumination scanning sequence, the detector array pixel sizes, and the distances between the specimen 150 and source/detector. The distance between the specimen 150 and the illumination source 110 may be the distance, d, between the top of the transparent layer 140 and the display surface 119. The distance between the specimen 150 and the light detector 160 may be the thickness of the transparent layer 165.

For an SPLM system 10 or e-Petri system having an illumination display 116 with a display surface 119 parallel to the sensing surface 162 of the light detector 160 and the specimen surface 140, the projection of a point on the plane of the specimen surface 140 onto the detection plane (i.e. plane of the sensing surface 162) will be shifted in increments related to sin θ. The angle, θ is the angle of a line from the light element 117 (e.g., the center of a set of illuminated pixels on an LCD) to the point of the specimen 150, with respect to the specimen surface plane normal vector. For small angles, the sub-pixel shifts can be approximated as equal and the solution for the motion vector of the LR sequence can be found by a simple one-dimensional optimization of, α. In cases where the illumination (LCD) plane and detector planes are parallel, the sub-pixel shifts should be 'exactly' equal.

Scheme 2—2D Color Imaging

In a second scheme, an SPLM system 10 or e-Petri system of embodiments may be designed to generate 2D color HR images of a specimen 150 using a suitable SR algorithm based on a sequence of LR color projection images captured by a color light detector 160. In this scheme, the SPLM system 10 or the e-Petri system includes a color light detector 112 (e.g., a color CMOS sensor) that can capture a sequence of sub-pixel shifted color LR projection images. The processor 210 can generate one or more SR color images using a suitable color super resolution technique with the sequence of sub-pixel shifted color LR projection images. The simplest technique involves using a monochromatic super resolution technique on each of the color components independently. In another example, a more complicated super resolution technique can be used that involves transforming to a different color space, such as the one found in Farsiu, Sina, et al., "Advances and challenges in super-resolution," Wiley Periodicals (2004), which is hereby incorporated by reference in its entirely for all purposes.

Scheme 3—2D Computed Color Imaging

In a third scheme, an SPLM system 10 or e-Petri system of embodiments may be designed to generate 2D color HR images of a specimen 150 using a suitable SR algorithm based on multiple sequences of LR frames, each sequence associated with a different wavelength or color of illumination 118. The SPLM system 10 or e-Petri system can construct a 2D color HR image based on each sequence associated with a different wavelength/color. The SPLM system 10 can combine the 2D color HR images associated with the different wavelengths to create a 2D multi-color HR image of the specimen 150. The SPLM system 10 or e-Petri system of these embodiments includes a scanning illumination source 100 with a color illumination display 116 (e.g., color LCD) or another device that can generate color illumination 118. Any suitable wavelengths and number of wavelengths may be used. In one example, wavelengths of light may be chosen that cover the widest viewable color range. In some cases, separate scans using different wavelengths/colors can be used to capture separate RGB sequences of projection images. In other cases, the light element 117 may sequentially alternate between the different wavelengths/colors in a single scan.

In one embodiment, the SPLM system 10 or e-Petri system may include a scanning illumination source 100 having a RGB illumination display 116 (e.g., a RGB LCD). In this embodiment, separate red, green, and blue (RBB) scans can be used to capture separate RGB sequences of LR projection images (i.e. red sequence, green sequence, and blue sequence). The SPLM system 10 or e-Petri system of this embodiment can generate an HR RGB image based each sequence. The SPLM system 10 or e-Petri system can combine the 2D color HR images based on each sequence to generate a RGB image.

Scheme 4—3D Imaging with 3D Display

In a fourth scheme, an SPLM system 10 or e-Petri system of embodiments may be designed for 3D imaging on a 3D display 230. In this scheme, the SPLM system 10 or e-Petri system can generate n 2D HR images at n different incidence angles to generate different views of the object 152 based on the different locations of the light element 117.

In this scheme, the scanning illumination source 110 scans the light element 117 to locations that generate illumination 118 from illumination angles in a range around each of the n different incidence angles of interest. For example, if a view of the object 152 from 30 is desired, the scanning illumination source 110 may scan the light element 117 to generate illumination 118 from illumination angles in the range of 30+/−2 degrees in X/Y. As another example, if a view of the object 152 from −30 degrees is desired, the scanning illumination source 110 may scan the light element 117 to generate illumination 118 from illumination angles in the range of −30+/−2 degrees in X/Y. The "angular" scan range for a single HR image may be constant and small (4 degrees in this example) relative to the large angle displacements used to get different views for 3D imaging. Each of the HR images is still obtained from reconstructing from an LR projection image sequence, captured by scanning the illumination, but at a much larger angle away.

The 2D HR images from different incidence angles can be combined and displayed on a 3D display 230 (e.g., 3D monitor), or as a rotating gif or video file. This can be achieved by using different regions of the illumination LCD to generate high resolution projection images of a sample, but from different angles.

In imaging schemes where a view at a plane parallel to the sensing surface may be desired, the scanning illumination source 110 may scan the light element 117 to locations that generate illumination 118 from illumination angles in a range around normal to the sensing surface. For example, the scanning illumination source 110 may scan the light element 117 to generate illumination 118 from illumination angles in the range of +/−2 degrees in X/Y.

Scheme 5—3D Focusing

In a fifth scheme, an SPLM system 10 or e-Petri system of embodiments may be designed to "focus" 2D HR images at different planes of interest through the specimen 150. The SPLM system 10 or e-Petri system can also stack the "focused" 2D HR images at different planes to generate a 3D HR image. For a three-dimensional specimen, the SPLM system 10 or e-Petri system can construct HR images from sequences of sub-pixel shifted LR projection images based on different motion vectors associated with different sub-pixel shifts in order to achieve "focusing" at different planes within the three-dimensional sample.

Under this scheme, the SPLM system 10 or e-Petri system can construct each focused 2D image at a plane based on a captured sequence of sub-pixel shifted LR projection images and the determined motion vector at the plane. For example, the SPLM system 10 or e-Petri system may create a 2D HD image of a slice of a specimen 150 at a plane. In this example, the SPLM system 10 or e-Petri system determines the motion vector of the LR projection images at that plane. The SPLM system 10 or e-Petri system constructs the focused 2D HD image based on the determined motion vector at the plane of interest and a sequence of sub-pixel shifted LR projection images captured by the light detector 160. The SPLM system 10 or e-Petri system can also refocus at multiple planes by constructing HR images using multiple motion vectors and the same sequence of sub-pixel shifted LR projection images.

Since the quality of the focus of the reconstructed image depends on the correct estimation of the sub-pixel shifts of the LR projection images, and these sub-pixel shifts depend on the distance of the specimen 150 between the light detector 160 and the illumination planes, using different sub-pixel shifts (i.e. motion vectors) in the reconstruction step can allow for refocusing to specific specimen planes above the light detector 160. This effectively allows for a single, extensive scan sequence of LR projection images to not only provide three dimensional data with projection images from different angles (previous scheme), but also focusing to specific three dimensional planes.

Figure 10:
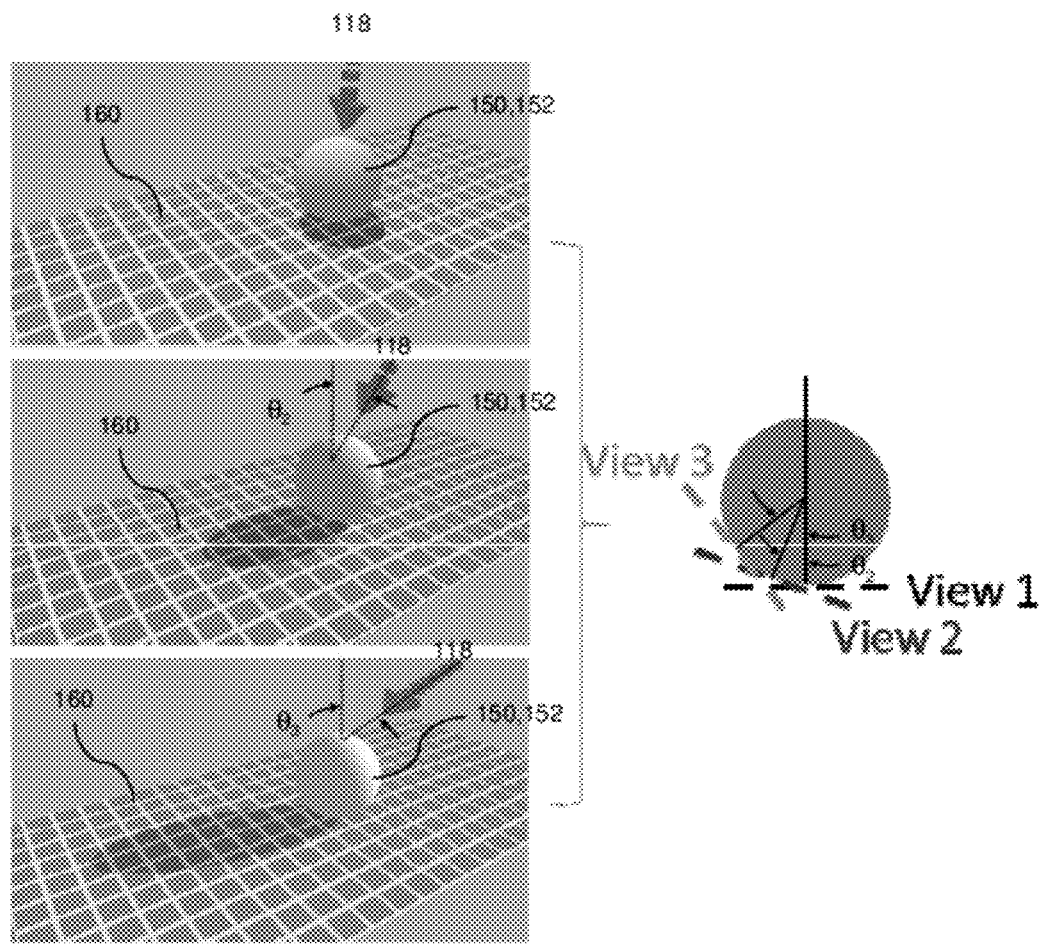
FIG. 10 is a schematic drawing of three projections on a light detector from three different illumination angles, $\theta_1$, $\theta_2$, and $\theta_3$, according to an embodiment of the invention.

In one embodiment, the scanning illumination device 110 sweep the light element 117 to generate illumination 118 between a wide range of illumination angles in order to generate an extensive scan sequence of LR projection images. FIG. 10 is a schematic drawing of three projections on a light detector 160 from three wide ranging incidence angles, $\theta_1$, $\theta_2$, and $\theta_3$, according to an embodiment of the invention. Changing the illumination angle of the light 118 from the light element 117 can generates a sequence of three projections associated with different views View 1, View 2, and View 3 of the object 152. In FIG. 10, $\theta_1$=0 degrees, and is in the direction of a negative z-axis. The light detector 160 can capture a sequence of LR projection images associated with the shifting projections. The light detector 160 can also capture multiple sequences of sub-pixels LR projection images associated with the illumination sweeping between the wide ranging incidence angles. This extensive scan sequence of LR projection images may be used to generate 3D data with projection images from the different views (previous scheme), but also to provide focusing to specific 3D planes.

III. E-Petri

Conceptually, the method of microscopy imaging used by the e-Petri system is simple to understand. Geometrically, a specimen (e.g., cells being cultured) is placed directly on the surface of a light detector (e.g. a CMOS image sensor) or on the surface of a transparent layer lying over the light detector. If an idealized image sensor with a high density grid of infinitesimally small pixels were used and the specimen were located directly on the image sensor surface, the idealized image sensor would be able to collect a shadow (projection) image of the specimen with excellent acuity. Unfortunately, currently available sensor chips have relatively large pixels (e.g., 2.2 microns). This implies that the direct shadow images of microscopic objects collected by conventional sensor chips are intrinsically coarse. Specifically, the raw shadow image resolution would be no better than two times the pixel size (as dictated by Nyquist criterion considerations). To address this, the following approach is taken to improve resolution or, more specifically, to generate a denser grid of smaller 'virtual' pixels.

First, it is noted that there may be a transparent layer (e.g., thin passivation layer) that separates the specimen from the actual light sensitive region of the sensor chip. With this recognition in mind, incoherent illumination is sequentially tilted/shifted above the specimen and a sequence of raw images may be acquired. With the incremental tilt/shift of the illumination, the target specimen's shadow will incrementally shift across the sensor pixels as shown in FIG. 3. The amount of shadow shift is proportional to the transparent layer thickness and the tilt/shift of the illumination source. As long as the shadow shift between each raw image frame is smaller than the physical pixel size, the information from sequence of sub-pixel-shifted shadow images can be combined to create a single HR image with a suitable pixel super-resolution algorithm. Some examples of super resolution imaging and super resolution algorithms can be found in Milanfar, P., "*Super-Resolution Imaging*," CRC Press, (2010), Hardie, R., Barnard, K. & Armstrong, E., "*Joint MAP registration and high-resolution image estimation using a sequence of undersampled images*," IEEE Transactions on Image Processing 6, pp. 1621-1633 (1997), Elad, M. & Hel-Or, Y., "*A fast super-resolution reconstruction algorithm for pure translational motion and common space-invariant blur*," IEEE Transactions on Image Processing 10, pp. 1187-1193 (2001), Farsiu, S., Robinson, M., Elad, M. & Milanfar, P., "*Fast and robust multiframe super resolution,*" IEEE Transactions on Image Processing," 13, pp. 1327-1344 (2004) ("Elad"), Farsiu, S., Robinson, D., Elad, M. & Milanfar, P., "*Advances and challenges in super resolution*," International Journal of Imaging Systems and Technology 14, 47-57 (2004), and Farsiu, S., Elad, M. & Milanfar, P., "*Multiframe demosaicing and super-resolution of color images*," IEEE Transactions on Image Processing 15, pp. 141-159 (2006), which are hereby incorporated by reference in their entirety for all purposes. An example of super resolution model and solution that uses a suitable super resolution algorithm is described in Section IIE.

A. E-Petri System

Figure 11:
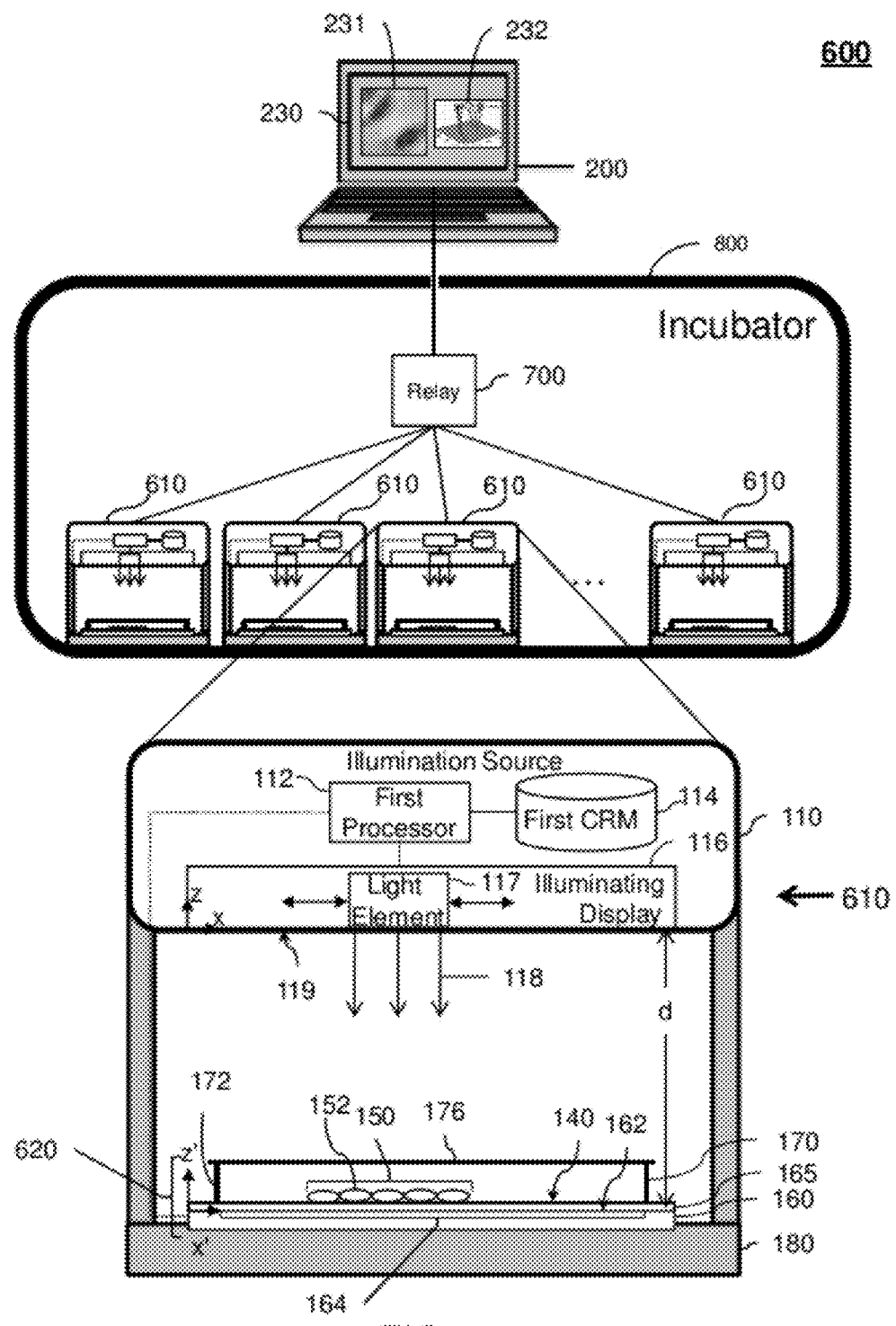
FIG. 11 is a schematic diagram of an e-Petri system having n e-Petri devices and an expanded view of one of the e-Petri devices, according to embodiments of the invention.

FIG. 11 is a schematic diagram of an e-Petri system 600 having n e-Petri devices 610 and an expanded view of one of the e-Petri devices 610, according to embodiments of the invention. n can be any suitable number such as 1, 2, 3, 4, 10, 20, etc. Each e-Petri device 610 of the e-Petri system 600 includes a scanning illumination source 110, an e-Petri dish 620, and support 180 for holding the scanning illumination source 110 in a fixed position relative to the light detector 160. The e-Petri system 600 also has a relay 700 (e.g., multiplexer), an incubator 800 for maintaining a predefined environment, and a host computer 200. The relay 700 is in electronic communication with the n e-Petri devices 610 to receive data. The host computer 200 is in electronic communication with the relay 700 to receive the data relayed and controlled (e.g., multiplexed) by the relay 700 from the n e-Petri devices 610. The n e-Petri devices 610 are located within a chamber formed by the walls of the incubator 800. The host computer 200 includes a second processor 210 (shown in FIG. 1), a second CRM 220 (shown in FIG. 1), and an image display 230. The image display 230 and the second CRM 220 in electronic communication with the second processor 210. In some cases, there may not be a second processor 210 or second CRM 220 and the functions of those components may be performed by one or more of the first processors 112 or first CRMs 114.

In FIG. 11, the e-Petri devices 610 include a scanning illumination source 110 capable of providing illumination 118 to a specimen 150 from a plurality of illumination angles. The scanning illumination source 110 includes a first processor 112, a first computer readable medium (CRM) 114, and an illuminating display 116 (e.g., an LCD, a light emitting diode (LED) display, etc.). In some cases, the first processor 112 and first CRM 114 may be separated from the scanning illumination source 110. The first processor 112 is in electronic communication with the illuminating display 116 and with the first CRM 114. The illuminating display 116 includes a light element 117 (e.g., a set of one or more illuminated pixels in an LCD/LED) providing illumination 118 (e.g., incoherent light). The illuminating display 116 also includes a display surface 119. The display surface 119 is located at a distance, d, from the sensing surface 162. The light element 117 is located at the display surface 119 in the illustrated example. In other embodiments, a transparent layer may be located between the display surface 119 and the light element 117 or may be located outside the display surface 119. The scanning illumination source 110 also includes an x-axis, a y-axis (not shown), and a z-axis. The x-axis and y-axis lie in a plane at the display surface 119.

The z-axis is orthogonal to this plane. As shown by a dotted line, the light detector 160 may optionally be in electronic communication with the first processor 112 of the scanning illumination source 110 to synchronize operations.

In FIG. 11, the e-Petri device 610 also includes an e-Petri dish 620. The e-Petri dish 620 includes a light detector 160 having a sensing surface 162 and a transparent layer 165 lying over the light detector 160 (e.g., commercially available CMOS image sensor having 2.2 micron pixels). In other cases, the transparent layer 165 may be part of the light detector 160. The sensing surface 162 includes a sensing area 164 (e.g., 6 mm×4 mm area). The transparent layer 165 includes a specimen surface 140 for receiving a specimen 150 (e.g., cell culture) and other materials (e.g., culture medium). The light detector 160 also has an x'-axis, a y'-axis (not shown), a z'-axis. The x'-axis and y'-axis lie in a plane at the sensing surface 162 of the light detector 160. The z'-axis is orthogonal to this plane. The e-Petri dish 620 also includes an optional well 170 having a peripheral wall 172 and an optional cover 176.

In FIG. 11, a specimen 150 with five objects 152 (e.g., cells) is located on the specimen surface 140 within the wall 172 of the well 170. Although five objects 152 are shown, the specimen 150 of other embodiments may have any suitable number (e.g., 1, 2, 10, 100, 1000, etc.) of objects 152 or portions (e.g., cell components) of objects 152.

The e-Petri system 600 in FIG. 11 may function as a multimodal on-chip imaging system with a multiplicity of functions, uses, and benefits. This system can be made in a low-cost and compact manner and can incorporate the ability to grow cells or other objects 152 on components of the system itself. For example, the e-Petri dish 620 can include a simple chamber design with a medium affixed to the light detector 160 where objects 152 (e.g. cells) can be cultured and stored. Multiple e-Petri devices 610 can be placed in a single incubator 800, to allow various functions to be performed, and different types of data to be generated, simultaneously. For example, different e-Petri devices 610 can use light elements 117 with different characteristics (e.g. wavelength, intensity), or filters to allow a user to image objects 152 in both bright-field and fluorescence simultaneously. Multiple arrays of chambers or a fluidic network can also be designed to provide control of chemical and mechanical environment (not shown). Thus, this imaging system may be able to replace imaging systems with conventional Petri dishes and well-plates in biology labs.

Figure 12:
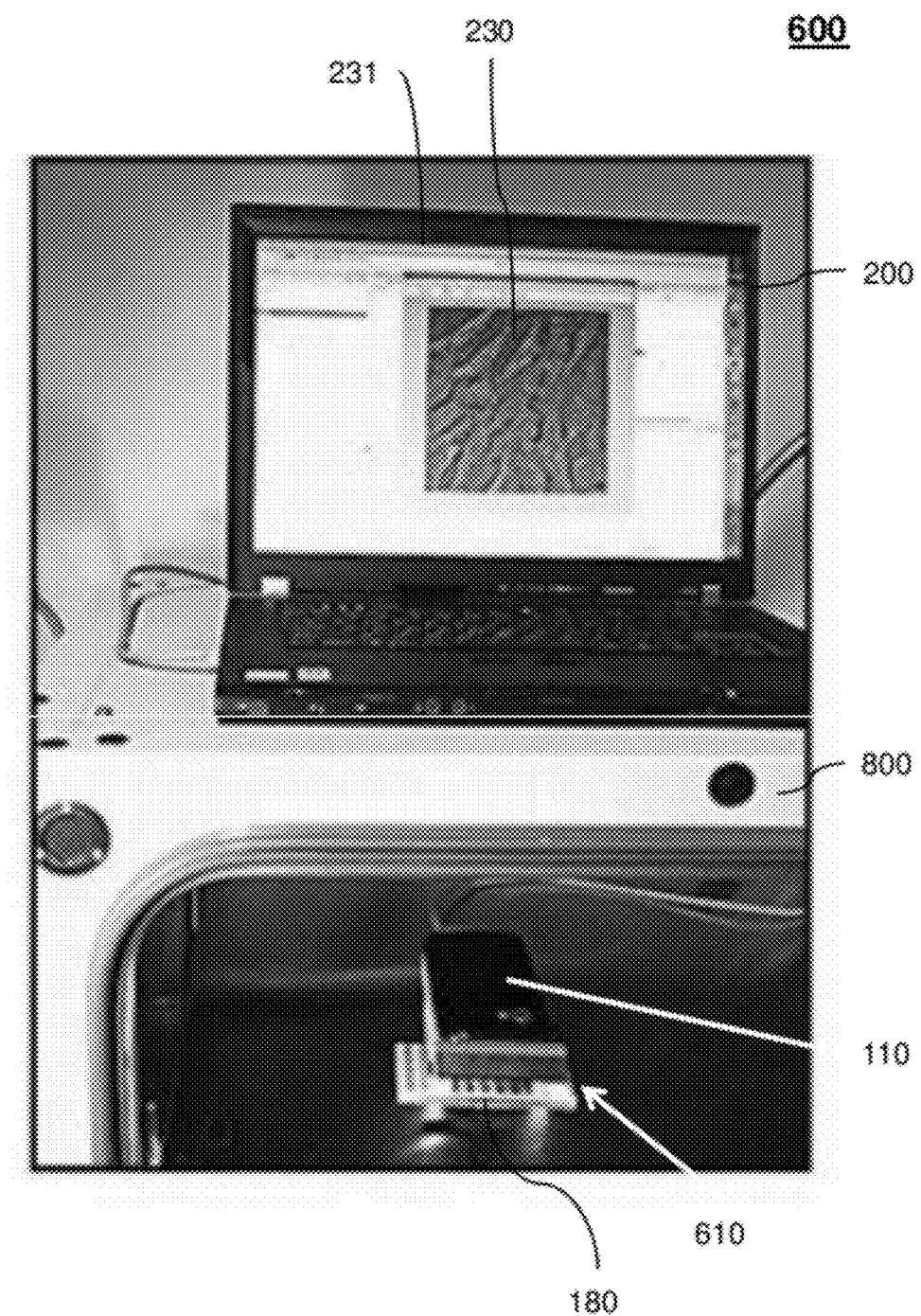
FIG. 12 is a photographic image of an e-Petri system having a single e-Petri device, according to embodiments of the invention.

FIG. 12 is a photographic image of an e-Petri system 600 having a single e-Petri device 610, according to embodiments of the invention. The e-Petri system 600 includes the e-Petri device 610, an incubator 800, and a host computer 200 in communication with the e-Petri device 610. The e-Petri device 610 includes a illumination source 110 in the form of a smartphone, an e-Petri dish 620 and a support 180 holding the illumination source 110 and the e-Petri dish 620. The e-Petri device 610 is located within the incubator 800 to control the environment. The host computer 200 includes a second processor 210 (shown in FIG. 1), a second CRM 220 (shown in FIG. 1), and an image display 230. The host computer 200 is in electronic communication with the e-Petri device 610 to receive image data to display an image 231 of a specimen 150 (not shown) on the display 230.

During an exemplary operation of an e-Petri system 600 of FIGS. 11 and 12, the illumination source 110 provides illumination 118 from different illumination angles at different illumination times to generate sub-pixel shifted light projections 170 (as shown in FIG. 3) of the specimen 150 at the sensing surface 162 of the light detector 160. The light detector 160 samples (captures) one or more sequences of sub-pixel shifted projection images of the specimen 150 at the different illumination times. The second processor 210 of the host computer 200 may receive data associated with the one or more sequences of sub-pixel shifted projection images. The data is relayed through the relay 700 from the light detector 150. The second processor 210 may determine motion vector of the projections 170 from one or more sequences of sub-pixel shifted projection images. The second processor 210 can use a suitable super resolution algorithm to generate one or more HR images of the specimen 150 based on the motion vector and data of one or more sequences of sub-pixel shifted projection images. The one or more HR images 230 and other related images 232 can be displayed on the display 230.

An imaging run of an e-Petri system 600 can refer to a time interval during which operations of the e-Petri system 600 generate a sub-pixel resolution image of a specimen 150 or a portion of a specimen 150 located at one or more of the e-Petri devices 610. An illumination cycle of an e-Petri device 610 can refer to the time interval during which the scanning illumination source 110 provides illumination 118 from a plurality of illumination angles corresponding to a plurality of illumination times. Any suitable number (e.g., 1, 10, 100, 1000, etc.) of illumination times and corresponding illumination angles can be used. The plurality of illumination angles may be designed to generate a sequence of sub-pixel shifted projections 170 (as shown in FIG. 3) of the specimen 150 on the sensing surface 162 of the light detector 160. The light detector 160 may sample a light projection 170 at sampling times corresponding to the illumination times. In FIG. 11, the light element 117 is shown at a single illumination time during an illumination cycle corresponding to a sampling time. In embodiments, an e-Petri system 600 can be designed to be automated to image (automatedly image) the specimen 150 periodically or otherwise repeatedly over a long term. In these cases, the e-Petri system 600 performs multiple imaging runs over a longer term. For example, the e-Petri system 600 may be designed to perform periodic imaging of a cell culture on an hourly basis over two-weeks.

FIG. 13(a) is a photographic image of an e-Petri dish 620 according to an embodiment of the invention, and a quarter for size comparison. The e-Petri dish 620 includes a light detector 160, a transparent layer 165, and a well 170. The light detector 160 is in the form of a commercially available CMOS image sensor chip with a 6 mm×4 mm imaging area filled with 2.2 micron pixels. The microlens layer and color filter on the image sensor chip were removed to provide direct access to the image sensor pixels (light detecting elements 166). The microlens layer and color filter were removed by treating the sensor chip under oxygen plasma for 10 min (80 W). The transparent layer 165 in the form of a thin PDMS layer was prepared by mixing 1:10 with base and curing agent, then spin coated onto the sensing surface 162 followed by baking at 80° C. for 1 hour. The well 170 is a plastic square well comprising a peripheral wall 172 glued at the inner edges to the transparent layer 165 of the light detector 160 with poly-dimethylsiloxane (PDMS). The e-Petri dish 620 also includes a cover 176 hinged to an outer edge of the peripheral wall 172. In FIG. 13(a) a pipette is shown introducing a specimen 150 into the well 170.

Figure 13:
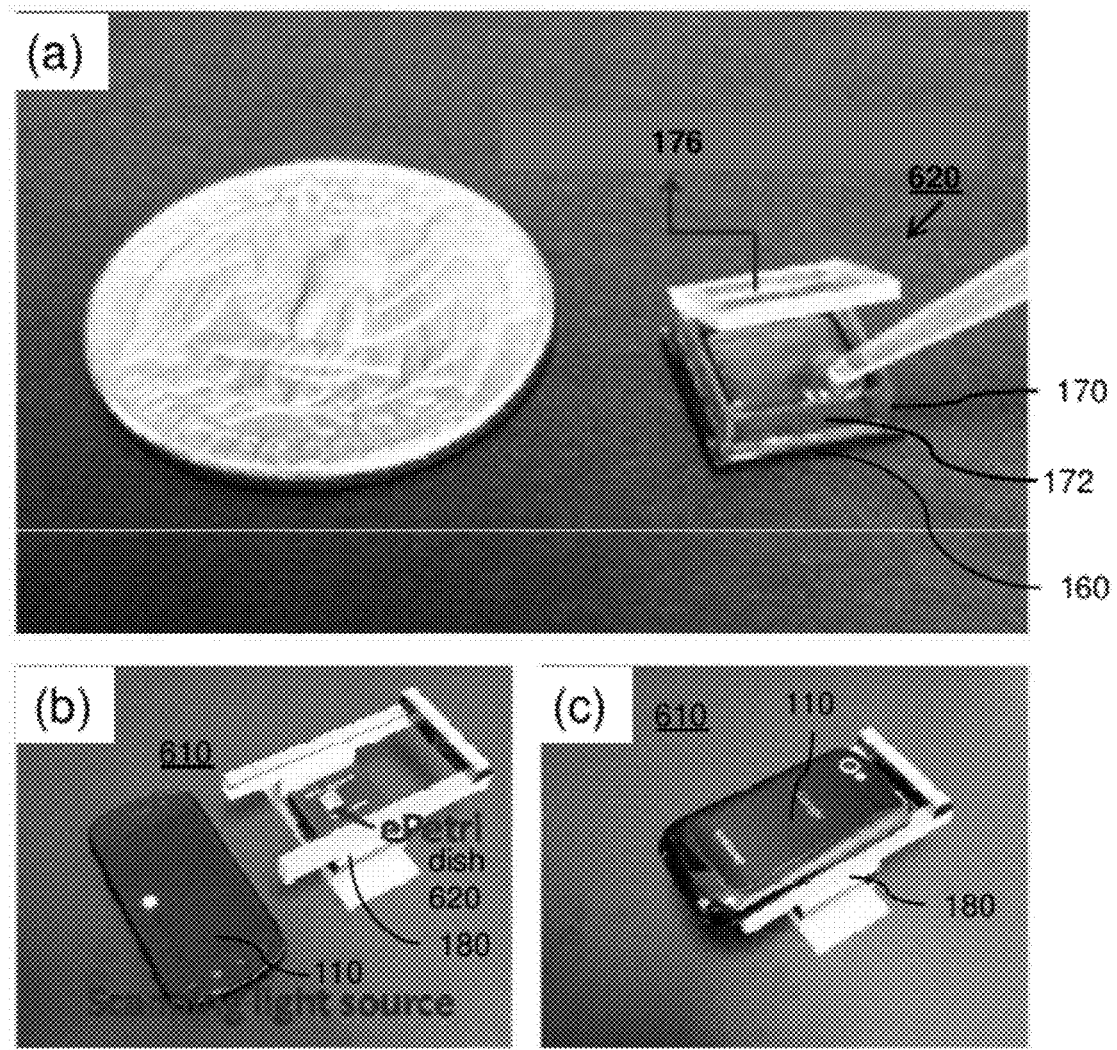
FIG. 13(a) is a photographic image of an e-Petri dish according to an embodiment of the invention, and a quarter for size comparison.
FIG. 13(b) is a photographic image of a partially disassembled e-Petri device having the e-Petri dish of FIG. 13(a), according to an embodiment of the invention.
FIG. 13(c) is a photographic of the assembled e-Petri device of FIG. 13(b), according to an embodiment of the invention.

FIG. 13(b) is a photographic image of a partially disassembled e-Petri device 610 having the e-Petri dish 620 of FIG. 13(a), according to an embodiment of the invention. As shown, the e-Petri device 610 includes a scanning illumination source 110 in the form of a smartphone with an illuminating display 116 in the form of a LED screen. The e-Petri device 610 also includes the e-Petri dish 620 of FIG. 13(*a*). The e-Petri device 610 also includes a support 180 for holding the scanning illumination source 110 in a fixed position at a distance 2.0 cm away from the light detector 160. In the illustrated example, the support 180 is made of building blocks that house the image sensor socket board and the smartphone. The parallel alignment between the display surface 119 and the sensing surface 162 may not be a critical consideration. In FIG. 13(*b*), e-Petri device 610 is shown partially disassembled with the illumination source 110 separate from the other components of the e-Petri device 610.

FIG. 13(*c*) is a photographic of the assembled e-Petri device 610 of FIG. 13(*b*), according to an embodiment of the invention. In FIG. 13(*c*), the illumination source 110 is located in the support 180. In an imaging run using the e-Petri device 610 of the illustrate example, the illumination source 110 provided illumination 118 from perspective illumination angles ranging from −60 degree to +60 degrees with respect to the sensing surface 162 of the light detector 160. The entire e-Petri device 610 can be placed in an incubator 800 for automatic long term cell imaging and tracking.

The e-Petri device 610 of embodiments is an on-chip imaging device where a specimen 150 such as cells and a culture medium can be stored and imaged. This device may be suitable to replace conventional microscopy devices having petridishes and well-plates in biology labs. The e-Petri device 610 of embodiments may include any suitable combination of structures and devices for storing and imaging the specimen 150. In FIGS. 11, 13(*a*), and 13(*b*), the e-Petri device 610 includes an illumination source 110, an e-Petri dish 620, and a support 180.

The e-Petri dish 620 of these embodiments is an on-chip design where the specimen 150 can be stored and in some cases imaged. This on-chip design may be suitable to replace conventional petridishes and well-plates in biology labs. The e-Petri dish 620 of embodiments may include any suitable combination of structures and devices for holding the specimen 150, maintaining the environment of the specimen 150, and/or imaging the specimen 150. For example, an e-Petri dish 620 may include a chamber design (e.g., well 170), which can be placed on an imaging sensor chip where cells and the culture medium can be stored. The chamber design can include an array of chambers. As another example, an e-Petri dish 620 may also include a fluidic network with one or more fluid channels. The fluidic network can also be designed to provide control of chemical and mechanical environment in the e-Petri dish 620. As another example, an e-Petri dish 620 may also include one or more dielectric cages for holding the specimen 150 or object(s) 152 in the specimen 150 in an area such as the sensing area 164. As another example, an e-Petri dish 620 may also include a support 180 for holding the e-Petri dish 620. In FIGS. 11, 13(*a*), and 13(*b*), the e-Petri dish 620 is comprised of a light detector 160 having a sensing surface 162, a transparent layer 165 having a specimen surface 140, and a well 170, and a cover 176.

The transparent layer 165 of the e-Petri dish 620 of embodiments may be any suitable material layer capable of separating the specimen 150 from the light sensitive region of the light detector 160. The transparent layer 165 may be a part of the light detector 160 or may be a separate layer (e.g., coating) lying over the light detector 160. The transparent layer 165 includes a specimen surface 140 for receiving the specimen 150. The transparent layer 165 may be made of any suitable material such as Polydimethylsiloxane (PDMS). The transparent layer 165 may have any suitable thickness (e.g., thickness in the range of several hundred nanometers to microns). In one example, the transparent layer 165 is 0.9 μm thick. In an embodiment where the transparent layer 165 is a layer lying over the light detector 160, the transparent layer 165 may be a passivation layer coated or deposited on top an imaging sensor chip. The transparent layer 165 may be comprised of multiple layers of different transparent materials in some cases. For example, the transparent layer 165 may be comprised of a thin passivation layer, a coating, and/or a culture medium.

The e-Petri dish 620 also includes a light detector 160 in the form of an imaging sensor chip capable of generating one or more signals with light data associated with the projection images 160 captured and other data associated with imaging. The light detector 160 can be a monochromatic detector or a color detector (e.g., RGB detector). Suitable imaging sensor chips are commercially available. In some cases, the light detector 160 includes a two-dimensional array of discrete light detecting elements 166 (shown in FIG. 2). Some examples of suitable light detectors 160 that have two-dimensional arrays of discrete light detecting elements 166 include a charge coupled device (CCD) array, a CMOS imaging sensor array, an avalanche photo-diode (APD) array, a photo-diode (PD) array, and a photomultiplier tubes (PMT) array. The arrays of light detecting elements can have any suitable orientation. Also, the light detecting elements 166 may be of any suitable size (e.g., 1-10 microns) and any suitable shape (e.g., circular, rectangular, square, etc.). For example, a CMOS or CCD light detecting element 166 may be 1-10 microns and an APD or PMT light detecting element 166 may be as large as 1-4 mm. The light detector 160 also includes a sensing surface 162 that has a sensing area 164, which can refer to an area of the sensing surface 162 that actively captures image projections 170. Although illustrated embodiments show the sensing area 164 covering a small portion of the sensing surface 162, in other embodiments, the sensing area may cover a larger portion or the entire sensing surface 162.

In some cases, the transparent layer 165 may be placed on the sensing surface 162 of an imaging sensor chip during fabrication of the chip using suitable fabrication procedures such as semiconductor and/or micro/nanofabrication procedures. In one case, the transparent layer 165 may be prepared by mixing 1:10 with base and curing agent, then spin coated on a 3 in. silicon wafer followed by baking at 80 degrees C. Due to the scattering angle of light 118 passing through the specimen 150, projection image quality can be degraded if the specimen 150 is located away from the sensing surface 162. For this reason, the transparent layer 160 may be a thin layer. Also, layers (e.g., color filter and a microlens layers) of the imaging sensor chip may be removed or omitted to decrease the acceptance angle of each light detecting element (pixel) and the distance between the specimen 152 and the sensing surface 162. To remove the color filter and a microlens layers from a pre-fabricated imaging sensor chip, the chip may be treated under oxygen plasma for a period of time (e.g., 10 minutes at 80 W).

In embodiments such as FIGS. 11 and 13(*a*), the e-Petri dish 620 also includes a well. The well 170 can refer to any suitable structure or structures capable of containing or holding a specimen 150 being imaged. The components of the well 170 such as the peripheral wall 172 may be made of any suitable material such as PDMS. In embodiments such as shown in FIG. 11, the well 170 includes a peripheral wall 172 directly coupled to the specimen surface 140. The peripheral wall 172 forms a square enclosure for containing the specimen 150. In other embodiments such as the embodiment shown in FIG. 13(*a*), the well 170 may be separate structure with a peripheral wall 172 and a transparent floor attached at a peripheral edge of the peripheral wall 172. The transparent floor may be coupled, removably or otherwise, to the specimen surface 140 or to the sensing surface 162 of the light detector 160. In other embodiments, the well 170 may include other structures such as an array of chambers. Each chamber capable of containing its own specimen 150.

In embodiments such as FIGS. 11 and 13(*a*), the e-Petri dish 620 also includes a cover 176 that can be placed over the well 170. The cover 176 may be any suitable structure that can provide suitable protection to the specimen 150. The cover 176 may be made of any suitable material (e.g., PDMS) and may have any suitable thickness (e.g., 100 μm). For example, a cover 176 may be a thin sheet of PDMS that prevents evaporation of the culture media while allowing for $CO_2$ exchange between the well 170 and the exterior. The cover 176 may be removable in some cases.

In embodiments such as FIGS. 11, 12, 13(*b*) and 13(*c*), the e-Petri device 610 may include a support 180. A support 180 can refer to suitable structures, devices or combination thereof capable of holding the scanning illumination source 110 in a fixed position relative to the light detector 160 and at a distance, d, from the specimen surface 140. The support 180 may be part of the e-Petri dish 620 in some cases. In FIG. 11 and FIG. 13(*b*), the support includes a bottom portion with an opening for receiving and/or coupling to the e-Petri dish 620. The support 180 of embodiments, such as shown in FIG. 13(*b*), also includes a portion for receiving the scanning illumination source 110. In some cases, such as the illustrated example of FIG. 11, FIGS. 13(*b*), and 13(*c*), the scanning illumination source 110 may be held such that the display surface 119 is kept approximately parallel to the sensing surface 162 of the light detector 160 and at a distance, d, from the sensing surface 162 during scanning. In these cases, the illuminating display 116 may provide illumination 118 at angles normal to the display surface 119. In other cases, the scanning illumination source 110 may be held so that the display surface 119 may be tilted at an angle from normal. At this angle, projections 170 from more extreme illumination angles to be captured, leading to a more complete 3D reconstruction in some cases. In one embodiment, the scanning illumination source 110 may include actuator(s) and controller(s) or other mechanism to reposition the illuminating display 116 (e.g., LCD array) at an angle from normal.

In embodiments, a specimen 150 located on the specimen surface 140 may be imaged by the e-Petri device 610 or the SMLM device 100. The specimen 150 may include any suitable number (e.g., 1, 2, 10, 100, 1000, etc.) of objects 152 or portions (e.g., cell components) of objects 152. The specimen 150 may also include other material such as a culture medium. In FIG. 11, a specimen 150 with five objects 152 (e.g., cells) is located on the specimen surface 140 within the wall 172 of the well 170. Any suitable specimen 150 may be imaged by the e-Petri system 600 or e-Petri device 610. For example, a suitable specimen 150 may be a confluent sample (e.g., cell culture) having one or more objects (e.g., cells). As another example, a suitable specimen 150 may be a sample in which the objects 152 are contiguously connected. The specimen 150 may include any suitable type of object 150. Suitable types of objects 150 can be biological or inorganic entities. Examples of biological entities include whole cells, cell components, microorganisms such as bacteria or viruses, cell components such as proteins, etc. Inorganic entities may also be imaged by embodiments of the invention.

In embodiments such as FIGS. 11, 12, 13(*b*) and 13(*c*), the e-Petri device 610 includes a scanning illumination source 110. The scanning illumination source 110 may include any suitable device or combination of devices capable of providing illumination 118 from different illumination angles to a specimen 150 located on the specimen surface 140 to generate sub-pixel shifted projections 170 of the specimen 150 at the sensing surface 162. Suitable scanning illumination sources 110 are commercially available. For example, a scanning illumination source may be a mobile communication device (e.g., smartphone, tablet, etc.) having an illuminating display 116. Illustrated examples of a suitable scanning illumination device 110 in the form of a smartphone are shown in FIGS. 2, 4, 12, 13(*b*), and 13(*d*). Another example of a suitable scanning illumination device 110 may be a tomographic phase microscope that uses a spatial light modulator to scan illumination 118. In illustrated embodiments, the scanning illumination source 110 is in the form of a mobile communication device.

In FIG. 11, the scanning illumination source 110 includes a first processor 112, a first CRM 114, and an illuminating display 116. The illuminating display 116 includes a display surface 119 and a light element 117 providing illumination 118 at the display surface 119.

The illuminating display 116 may be any suitable display capable of providing illumination 118. Suitable illuminating displays 116 are commercially available. Some examples of suitable illuminating displays 116 include monochromatic, color, or gray-scale LCDs, LED displays (e.g., display panels), television screens, LCD matrixes, etc. The illuminating display 116 may be in the form of a two-dimensional array of light emitting components (e.g., light pixels) with a dimension M×N of any suitable value (e.g., 1000×1000, 1000×4000, 3000×5000 etc.). Each light emitting component in the two-dimensional array may have a location denoted as $(x_i, y_j)$ where i=1 ... M; and j=1 ... N. The illuminating display 116 includes a display surface 119. The illuminating display 116 may be in any suitable position to provide illumination 118. In FIG. 11, the illuminating display 116 is positioned so that the display surface 119 is parallel to the sensing surface 162 and is at a distance, d, from the sensing surface 162.

A light element 117 can refer to any suitable device capable of providing illumination 118. In FIG. 11, the light element 117 is shown located at the display surface 119. In other embodiments, the light element 117 may be located below the display surface 119. In embodiments, the light element 117 can be a set of one or more illuminated light emitting elements (e.g., LCD lit/pixel) of the illuminating display 116 at a given illumination time during an illumination cycle. The set may have any suitable number (e.g., 1, 5, 10, 100, etc.) of light emitting components. In these embodiments, the light element 117 may be different sets of light emitting elements illuminated at different times during the illumination cycle. The light element 117 may be any suitable size and shape (e.g., rectangle, circle, spot, bar, etc.). In FIG. 4(*a*), the light element 117 has the shape of a circular spot comprising a set of 640 illuminated pixels of about 1 cm in diameter on the illuminating display 116. In addition to the position, the size and shape of the different sets of illuminated light emitting elements may vary over time. In other embodiments, the light element size and shape may be constant.

During an illumination cycle, the scanning illumination source 110 may provide the light element 117 at a plurality of positions at different times to provide illumination 118 to the specimen 150 from a plurality of illumination angles. For example, the light element 117 may be different sets of light emitting elements at a plurality of positions on an illumination display 116. The scanning illumination source 110 may change the light element 117 to the plurality of different positions by illuminating different sets of light emitting elements at different times. In this example, the position of each light element 117 can refer to the coordinates of the center of the set of illuminated light emitting components. As another example, the light element 117 may be tilted at a plurality of different angles at different times. As another example, the light element 117 may be a single light source that is moved to the plurality of positions. As another example, the light element 117 may be different sets of light sources at the plurality of positions in the incubator 800 that are illuminated at different times. The plurality of positions may include any suitable number, n, of positions (n=1, 2, 3, 4, 5, 10, 20, 100, 1000, etc.). The plurality of illumination angles may include suitable illumination angles that can generate sub-pixel shifted projections 170 of the specimen 150 at the sensing surface 162. In one case, the light element 117 may be positioned to generate a small range of illumination angles (e.g., +/−2 degrees) in X/Y around a normal to the sensing surface 162.

In FIGS. 11, 12, 13(*b*), and 13(*c*), different sets of one or more light emitting components (e.g., pixels) of the illuminating display 116 may be illuminated at different times to change the position of the light element 117 and/or properties of the illumination 118 from the light element 117. In these illustrated examples, the scanning illumination source 110 is in the form of a smartphone having an illuminating display 116 in the form of a two-dimensional array of light emitting components. Different sets of light emitting components in the two-dimensional array may be illuminated at different times during the illumination cycle.

In embodiments, the scanning illumination source 110 may position the light element 117 in any suitable plurality of positions and the light element 117 may have any suitable properties during the illumination cycle. In some cases, the plurality of positions may as a group form a pattern (e.g., array, circle, square, triangle, etc.). In one embodiment, the light emitting components of an illuminating display 116 may be illuminated during an illumination cycle according to a scanning pattern. A scanning pattern can refer to a description that includes the plurality of positions of the light element 117 at different illumination times during an illumination cycle and the properties (e.g., size, shape, etc.) of the light element 117 at each position. In one embodiment, a scanning pattern may be in the form of a two-dimensional array (n×m dimensions) of positions of the light element 117 at ($x_{i=1\ to\ n}$, $y_{j=1\ to\ m}$) of the illuminating display 116. The array may have any suitable dimension (e.g. 1×100, 1×10, 100×100, 3000×20, 400×300 etc.). In one example, a scanning pattern may include a two-dimensional array of scanning locations and a description that the light element 117 moves through each row sequentially at a constant rate. In another example, the scanning pattern may include a two-dimensional array of scanning locations and a description that the element moves through each column sequentially at a constant rate. As another example, the scanning pattern may include a two-dimensional array of scanning locations and a description that the element moves through the array randomly. The scanning pattern may also include the amount of sub-pixel shift desired between subsequent projection images. The scanning pattern may also include the total number of projection images and/or HR images desired.

FIG. 4(*b*) illustrates an example of a scanning pattern of an illumination cycle according to an embodiment. The scanning pattern is in the form of a graph of a 15×15 two-dimensional array of 225 positions of the light element 117 on the display surface 119 during an illumination cycle. The 225 positions are shown in terms of x and y locations along the x-axis and y-axis in the plane of the display surface 119 of the illuminating display 116. In the illustrated example, the scanning pattern includes 15 columns of positions in the x-direction and 15 rows of positions in the y-direction. At each position, the light detector 160 may capture a different projection image. The light detector 160 may capture as many as 225 different projection images based on the 225 different scanning positions in the scanning pattern. The projection images captured by the light detector 160 may comprise one or more sequences of sub-pixel shifted projection images. The arrows in the scanning pattern FIG. 4(*b*) designate the sequence in time of the positions during the illumination cycle. According to the illustrated arrows, the light element 117 moves sequentially through each row of the two-dimensional array in the scanning pattern.

The scanning pattern may be stored as code on the first CRM 114 or the second CRM 220 and executed by the first processor 112 or second processor 210. For example, the scanning pattern may be a video program (e.g., app on a smartphone) of a suitable format stored on the first CRM 114 that when executed displays a video of the light element 117 moving to different positions on the illuminated display 116 over time. An example of such a video is illustrated in FIG. 4(*a*). In this example, the light element 117 is in the form of a light spot moving across the illuminating display 116 over time according to positions defined in the scanning pattern in FIG. 4(*b*). In FIG. 4(*a*), the light element 117 is at one position in the scanning pattern shown in FIG. 4(*b*). In this example, the illuminating display 116 is centered over the e-Petri dish 620. The light element 117 can have constant or varied properties at different positions. In one case, the light element 117 may remain a constant size as it moves away from the center of the illuminating display 116. In this case, the intensity readout from the light detector 160 associated with the specimen 150 will decrease away from the center because of the large incident angle. In the illustrated case shown in FIGS. 4(*a*) and 4(*b*), to maintain a more constant intensity readout, the size of the light element 117 (e.g., bright spot size) is linearly increased as it moves away from the center of the illuminating display 116 (e.g., smartphone screen).

In embodiments, the properties (e.g., size, properties of the illumination 118, shape, etc.) of the light element 117 may vary at different positions during an illumination cycle. The properties of the light element 117 at different positions may be varied by changing the number of light emitting elements in the light element 117, the shape of the light element 117, and/or the properties of the light 118 from the light emitting elements in the light element 117. The light properties (e.g., intensity, wavelength, frequency, polarization, phase, spin angular momentum and other light properties) of the illumination 118 from a light element 117 at an illumination time during an illumination cycle have any suitable values. The illumination 118 may be incoherent light in some cases.

The light intensity requirement of the imaging schemes used by the e-Petri device are relatively low in embodiments. In one embodiment, a suitable intensity of illumination 118 can be the provided by illumination from a conventional smartphone screen. As a point of reference, a halogen-lamp based conventional microscope typically delivers a light intensity of 20 W/m² onto a specimen 150. In other embodiments, a suitable intensity of illumination 118 can be the provided by a LED display panel, a television screen or a LED matrix. A suitable light intensity received by a light detecting element 166 may be 0.015 W/m².

In an embodiment, the intensity of the illumination 118 generated by the light element 117 in an illuminating display 116 may be controlled by varying the size of the light element 117. In some cases, the size of the light element 117 at different positions during an illumination cycle may vary based on the distance between the position of the light element 117 and a point at the plane of the sensing surface 162 to generate light of approximately the same intensity at that point. In this case, the size, S of the light element 117 at a position can be proportional to the distance, L, from the position to a suitable location of a point such as: a) the center of the array of scanning locations, or b) the center of an illuminating display 116 such as the center of an LCD on a smartphone. For example, the size, S of the light element 117 at a position in the illumination cycle may be defined as: $S=S_{center}\times(1+L)$, where $S_{center}$ is the size of the light element 117 at the center of the array of positions. In this way, the light intensity received at the location at the sensing surface 162 normal to the center of the positions of the light elements 117 on the display surface 119 may be kept approximately constant. As another example, the size S of the light element 117 at any position of the light element 117 may be defined as: $S=S_A\times(1+A)$, where $S_A$ is the size of the light element 117 at a location A of an illuminating display 116, A is the distance from the position to the location A.

In an embodiment, the light element 117 can provide illumination 118 of n different wavelengths $\lambda_1, \ldots, \lambda_n$ at n different illumination times during an illumination cycle. The illumination 118 may be cycled through a series of different wavelengths as the light element 117 moves through different positions in an illumination cycle in some examples. In one example, the light element 117 can provide RGB illumination of three wavelengths $\lambda_1$, $\lambda_2$, and $\lambda_3$ corresponding to red, green, blue colors, respectively. The light element 117 may provide illumination 118 of the three wavelengths $\lambda_1$, $\lambda_2$, and $\lambda_3$ sequentially during illumination times of a illumination cycle. In one case, at a illumination time $t_1$ illumination 118 may have a wavelength of $\lambda_1$, at $t_2$ illumination 118 may have an wavelength of $\lambda_2$, at $t_3$ illumination 118 may have a wavelength of $\lambda_3$, at $t_4$ illumination 118 may have a wavelength of $\lambda_1$, at $t_5$ illumination 118 may have a wavelength of $\lambda_2$, etc. In this embodiment, the light detector During an illumination cycle, illumination 118 from the plurality of illumination angles generates a plurality of light projections 170 on the sensing surface 162. Each projection image (frame) can refer to a snapshot image sampled by the light detector 160 at a sampling time during an illumination cycle. In some cases, the light detector 160 may capture a projection image 170 at each illumination time. Each projection image sampled by the light detector 160 can be used to display a 2D projection image. In embodiments with a color light detector 160, the 2D projection image may be a color image. In embodiments with a monochromatic light detector 160, the projection image may be a black and white image.

A sequence of sub-pixel shifted projection images can refer to n projection images sampled at n sampling times where neighboring (in time or space) projection images are separated by less than a pixel size (i.e. sub-pixel shift). During an illumination cycle, n projection images ($I_1, \ldots, I_n$) may be captured at n sequential sampling times ($t_1, \ldots t_n$). Any suitable number (e.g., 1, 3, 5, 10, 100, etc.), n, of projection images may be captured by the light detector 160 during a illumination cycle. Also, any suitable number (e.g., 1, 3, 5, 10, 100, etc.) of sequences of sub-pixel shifted projection images may be captured by the light detector 160 during a illumination cycle. If multiple sequences are captured, the sequences can include different groups of projection images or the sequences can overlap sharing one or more projection images. In one example, 9 projection images ($I_1, I_2, I_3, I_4, I_5, I_6, I_7, I_8, I_9$) may be captured at 9 sequential sampling times ($t_1, t_2, t_3, t_4, t_5, t_6, t_7, t_8, t_9$). In an overlapping case of the above example, sequences could be: 1) $I_1$, $I_2$, $I_6$, and $I_8$, and, 2) $I_6$, $I_7$, $I_8$, and $I_9$. In a non-overlapping case, sequences could be: 1) $I_1$, $I_2$, $I_3$, and $I_4$, and 2) $I_5$, $I_6$, $I_7$, and $I_8$. In others examples, a sequence of sub-pixel shifted projection images may be based on non-sequential sampling times. For example, 9 projection images ($I_1, I_2, I_3, I_4, I_5, I_6, I_7, I_8, I_9$) may be captured at 9 sequential sampling times ($t_1, t_2, t_3, t_4, t_5, t_6, t_7, t_8, t_9$) and the sequence of projection images may be ($I_6, I_2, I_9, I_1$).

In embodiments, the light detector 160 may capture a projection image at each position of the light element 117 in a scanning pattern. For example, a light detector 160 may capture 225 projection images associated with the 15×15 array of positions in the scanning pattern shown in FIG. 4(b). In this example, the light detector 160 may capture a projection image at each position as the light element 117 moves through each row sequentially of the two-dimensional array of positions in the scanning pattern. If the positions in each row are associated with 15 sub-pixel shifted projections 170, the light detector 160 may capture 15 sequences of 15 sub-pixel shifted projection images during each illumination cycle. In this case, each of the 15 sequences captured is associated with a row of positions of the light element 117 in the scanning pattern.

In FIG. 11, the first processor 112 of the illumination source 110 is in electronic communication with the illuminating display 116, the first CRM 114, and the light detector 160. The first processor 112 (e.g., microprocessor) can execute code stored on the first CRM 114 (e.g., memory) to perform some of the functions of the scanning illumination source 110. For example, the first processor 112 may execute code with a scanning pattern stored on the first CRM 114. The CRM 114 may include, for example, code with a scanning pattern, other code for scanning a light element 117, and other codes for other functions of the scanning illumination source 110. The first CRM 114 may also include code for performing any of the signal processing or other software-related functions that may be created by those of ordinary skill in the art. The code may be in any suitable programming language including C, C++, Pascal, etc.

Light data can refer to any suitable information related to the one or more projections 170 captured by the light detecting elements 166 of the light detector 160. For example, light data may include information about the properties of the projection light received such as the intensity(ies) of the light, the wavelength(s) of the light, the frequency or frequencies of the light, the polarization(s) of the light, the phase(s) of the light, the spin angular momentum(s) of the light, and/or other light properties associated with the light received by the light detecting element 166. Light data may also include the location of the receiving light detecting element(s) 166, the time that the light was received (sampling time or scanning time), or other information related to the projection 170 received. In embodiments, each light detecting element 166 can generate a signal with light data based on light associated with the projection 170 and received by the light detecting element 166.

A motion vector can refer to the translational motion of projection images in a sequence of projection images, collectively termed the motion vector of the sequence of projection images. The motion vector is based on the amount of shifting of the projection images at a plane. A motion vector of a sequence of sub-pixel shifted projection images can be calculated from the associated projection images captured by the light detector 160. The motion vector may be calculated at any plane of interest. For example, the motion vector can be determined at the plane at the sensing surface 162. In this example, the motion vector is determined in terms of the local x'-axis and y'-axis at the sensing surface 162 of the light detector 160. As another example, the motion vector can be calculated at other planes through the specimen 150 being imaged. The planes through the specimen 150 may be parallel to the plane of the sensing surface 162 in some cases.

In embodiments of the e-Petri system 600, a sub-pixel resolution image of a specimen 150 can be constructed using a suitable SR algorithm based on data associated with a sequence of sub-pixel shifted projection images and a motion vector of the sub-pixel shifted projections in the sequence. An example of image resolution obtainable by embodiments of the e-Petri system 600 may be about 0.66 micron. Any suitable SR algorithm can be used. An example of a suitable SR algorithm is a shift-and-add pixel SR algorithm. Other examples of SR algorithms are discussed in Section II.

A sub-pixel resolution image generated based on a motion vector will be focused at a plane of interest associated with the motion vector. That is, if a motion vector is estimated based on a plane of interest, the sub-pixel resolution image will be a two-dimensional image focused at the plane of the interest used to estimate the motion vector. For example, if a motion vector is estimated based on a plane of interest at the sensing surface 162, the sub-pixel resolution image generated will be focused at the plane of the sensing surface 162. If the motion vector is estimated based on a plane through the specimen 150 being imaged, the sub-pixel resolution image will be a cross-sectional image of the specimen 150 focused at the plane through the specimen 150. In an embodiment, an e-Petri system 600 can generate a sub-pixel resolution image of a cross-section of the specimen 150 by modifying the value of the motion vector used to generate the sub-pixel resolution image to the plane at the cross-section. The e-Petri system 600 can vary the values of the motion vector to focus at various cross sections of the specimen 150. In an embodiment, an e-Petri system 600 can generate a three-dimensional sub-pixel resolution image based on multiple two-dimensional cross-sectional sub-pixel resolution images generated using multiple motion vector values associated with multiple planes through the specimen 150.

The e-Petri system 600 of FIG. 11 also includes a host computer 200 communicatively coupled to the light detector 160. The host computer 200 comprises a second processor 210 (e.g., microprocessor), a second CRM 220, and an image display 230. The image display 230 and the second CRM 220 are communicatively coupled to the second processor 210. Alternatively, the host computer 200 can be a separate device from the e-Petri system 600. The host computer 200 can be any suitable computing device (e.g., smartphone, laptop, tablet, etc.).

The second processor 230 executes code stored on the second CRM 220 to perform some of the functions of the e-Petri system 600 such as, for example: interpreting data from one or more sequences of sub-pixel shifted projection images captured and communicated in one or more signals from the light detector 160, determining a motion vector of a sequence of sub-pixel shifted projections, constructing a 2D HR image from data associated with a sequence of sub-pixel shifted projection images, constructing a 3D HR image from data associated with a sequence of sub-pixel shifted projection images, displaying one or more HR images on the image display 230, automatedly reconstruct images and display the reconstructed images on the display 230 for user monitoring, etc.

The second processor 210 can receive one or more signals with light data and other data from the light detector 160. For example, the processor 210 can receive one or more signals with light data associated with one or more sequences of sub-pixel shifted projection images sampled at a corresponding sequence of n illumination times ($t_1$, $t_2$, $t_3$, ... $t_n$). The second processor 210 can also determine a motion vector based on the sequence of sub-pixel shifted projection images. The second processor 210 can also construct HR images and associated image data based the determined motion vector and data associated with at least one sequence of sub-pixel shifted projection images. In some cases, the constructed HR image of the object 150 is a black and white 2D/3D image. In other cases, the constructed HR image of the object 150 is a color 2D/3D image.

In one embodiment, a HR color image can be generated by using different wavelengths of illumination 118 at different sampling times to generate a multiple sequences of sub-pixel shifted projection images at a light detector 160. Each sequence is associated with a different wavelength. The second processor 210 can generate HR color image and associated image data based on the different sequences associated with different wavelengths. For example, three wavelengths of light (e.g., wavelengths associated with red, green, blue (RGB) colors) can be sequentially generated by a light element 117 to generate three sequences of sub-pixel shifted projection images associated with three wavelengths of light. The processor 210 can combine the image data from the sequences associated with the different wavelengths to generate multi-wavelength or color image data (e.g., RGB color image data). The multi-wavelength or color HR image data can be used to generate a multi-wavelength or color HR image on the image display 230.

Second CRM (e.g., memory) 220 can store code for performing some functions of the e-Petri system 600. The code is executable by the second processor 210. For example, the second CRM 220 of embodiments may include: a) code with a SR algorithm, b) code with a tomography algorithm, c) code for interpreting light data received in one or more signals from the light detector 160, d) code for generating a 3D HR image, e) code for constructing a color sub-pixel image, f) code for displaying SR two-dimensional and/or three-dimensional images, g) code for a customized program to automatically reconstruct and display the reconstructed image onto the display 230 for user monitoring; and h) and/or any other suitable code for performing functions of the e-Petri system 600. The second CRM 220 may also include code for performing any of the signal processing or other software-related functions that may be created by those of ordinary skill in the art. The code may be in any suitable programming language including C, C++, Pascal, etc.

The e-Petri system 600 also includes an image display 230 communicatively to the processor 210 to receive data and provide output such as HR images to a user of the e-Petri system 600. Any suitable display may be used. For example, the image display 230 may be a color display or a black and white display. In addition, the image display 230 may be a two-dimensional display or a three-dimensional display. In one embodiment, the image display 230 may be capable of displaying multiple views of an object 150.

The e-Petri system 600 of embodiments also includes an incubator 800. An incubator can refer to any suitable device/structure or combination of devices and structures that can provide a pre-defined environment at the e-Petri dish 620 during a time interval of the experiment (e.g., long term study) being performed by the e-Petri system 600. The pre-defined environment may define environmental variables such as temperature, humidity, etc. Suitable incubators are commercially available. In some cases such as the illustrated example in FIGS. 11 and 12, the incubator 800 may include a chamber defined by a wall. The chamber may be designed to hold one or more e-Petri-devices 610.

The e-Petri system 600 of embodiments also includes a relay 700. A relay 700 can refer to a suitable device that can relay data from the one or more e-Petri devices 610 to the host computer 200. Suitable devices are commercially available. The relay 700 may include multiplexing functionality to combine signals from the one or more e-Petri devices 610 to a signal to the host computer 200. The relay 700 may also include demultiplexing functionality to extract data from a signal from the host computer 200 to send in a signal to one or more e-Petri devices 610. The relay 700 may transmit data wirelessly.

Modifications, additions, or omissions may be made to e-Petri system 600, e-Petri device 610 or e-Petri dish 620 without departing from the scope of the disclosure. For example, an e-Petri system 600 of other embodiments may omit the incubator 800 and/or the relay 700. As another example, an e-Petri device 610 of other embodiments may omit the support 180 or may have a single support 180 for multiple e-Petri devices 610. As another example, an e-Petri system 600 may omit the host computer 200. As another example, an e-Petri system 610 may omit the well 170 and wall 172.

In addition, components of the to e-Petri system 600, e-Petri device 610 or e-Petri dish 620 may be integrated or separated according to particular needs. For example, an e-Petri system 600 may have a single scanning illumination source 110 that provides illumination 118 to multiple e-Petri devices 610. As another example, the relay 700 may be located outside the incubator 800. As another example, the second processor 610 may be integrated into the light detector 160 so that the light detector 160 performs one or more of the functions of the second processor 160 in another e-Petri system 600. As another example, the second processor 160, second CRM 220, and image display 230 may be components of a computer separate from an e-Petri system 600 and in communication with the e-Petri system 600. As another example, the second processor 160, second CRM 220, and/or image display 230 may be integrated into parts of the e-Petri device 610. For example, the image display 230 may be part of the illumination display 116, the first processor 112 and second processor 210 may be integrated into a single processor, and/or the first CRM 114 and second CRM 220 may be integrated into a single CRM. As another example, more than one e-Petri dish 620 and/or the incubator 800 can be incorporated into the e-Petri device 610.

B. Wide Field-of-View Imaging Capabilities

The e-Petri device 610 of embodiments are capable of wide field-of-view imaging. By providing a wide field of view, the e-Petri device 610 of embodiments may be suitable to replace or improve upon conventional microscopes for cell culture analysis.

To demonstrate these capabilities, a specimen 150 having HeLa cells was cultured for 48 hours on a specimen surface 140 of an e-Petri-dish 620 of an e-Petri device 600 of an embodiment as shown in FIG. 13(c). To promote cell adhesion, the specimen surface 162 of the e-Petri dish 620 was treated with Poly-L-lysine (0.01%) for 15 min and washed 3 times with distilled water. The HeLa cells were first cultured in Dulbecco's modified eagle medium supplemented with 1-glutamine (4 mM), penicillin (100 units/ml), streptomycin (100 µg/ml) and 10% (v/v) fetal calf serum in culture dishes and maintained in 5% CO2 humidified atmosphere at 37° C. During the logarithmic growth period, the HeLa cells were harvested by trypsin (0.05% trypsin with EDTA*4Na), re-suspended in DMEM, and then seeded onto the ePetri dish 620.

The specimen 150 was then stained with Giemsa, which is a black precipitate formed from the addition of aqueous solutions of methylene blue and eosin, dissolved in methanol. The following steps were used to stain the cell culture: 1) fix the air-dried sample in absolute methanol by dipping the ePetri dish 620 briefly (two dips) in a Coplin jar containing absolute methanol; 2) remove and let air dry; 3) stain with diluted Giemsa stain (1:20, vol/vol) for 20 min.; and 4) wash by briefly dipping the ePetri dish 620 in and out of a Coplin jar of distilled water (one or two dips).

The e-Petri device 600 in FIG. 13(c) has an illumination source 110 in the form of a smartphone with an illuminating display 116 in the form of an LED display. During an exemplary illumination cycle, a video with a light element 117 in the form of a light spot was displayed on the LED display at a plurality of positions according to the 15×15 array scanning pattern shown in FIG. 4(b). FIG. 4(a) is illustrated example of the light spot 117 at one position. The light element 117 provided illumination 118 of three wavelengths $\lambda_1$, $\lambda_2$, and $\lambda_3$ corresponding to red, green, blue colors at different positions during the video. The imaging run included a single illumination cycle. The sampling rate (i.e. image capture rate) of the light detector 160 was set to capture 10 frames per second with a pixel clock of the light detector 160 running at 70 Mhz. The entire data acquisition process of the imaging run took about 20 seconds.

FIG. 7(a) shows the reconstructed color projection image of the confluent HeLa cell sample. To illustrate the amount of detail in the constructed color image shown in FIG. 7(a), reconstructed images of selected regions of the HeLa sample are provided in FIGS. 7(b2) and 7(c2). FIGS. 7(b1) and 7(c1) are projection images of the selected regions of FIGS. 7(b2) and 7(c2). The image enhancement factor used in the algorithm to generate the reconstructed image of FIG. 7(a) was set at 13. In other words, each pixel at the low-resolution projection image level (2.2 µm) was enhanced into a 13×13 pixel block in the reconstructed image. The entire reconstructed image of FIG. 7(a) contains about 8.45×108 pixels. The e-Petri device 600 of FIGS. 13(b) and 13(c) took about 22 second to capture each sequence of projection images for each color. The solution for the reconstructed image was non-iterative, deterministic and was optimized in the Maximum-Likelihood sense. With the use of a graphics processing unit (GPU), image processing time may be less than one second for the entire image reconstruction. Since the primary use of ePetri device 610 would be for tracking cell culture growth directly from within an incubator, the data transfer or the processing speed limitations should not reduce efficiency of the system.

From the reconstructed high resolution color images in FIGS. 7(b2) and 7(c2), organelles within the HeLa cell sample can be discerned such as the multiple nuclear granules (indicated by red arrows), and the nucleus. FIG. 7(d) is a conventional microscopy image of similar cells using a microscope with 40x, NA=0.66 objective lens for comparison.

Figure 14:
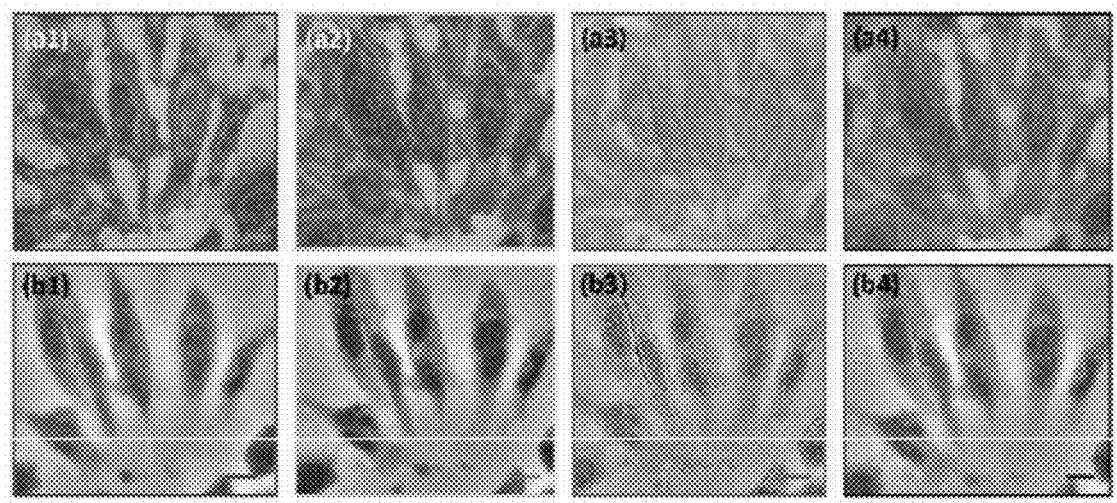
FIG. 14 (a1), FIG. 14(a2), and FIG. 14(a3) are conventional microscopy images with red, green and blue LED illuminations (20× objective, 0.5 N.A.).

In an experiment, a HeLa cell sample was cultured on a CMOS sensor chip and fixed and stained with Giemsa. FIG. 14 (a1), FIG. 14(a2), and FIG. 14(a3) are conventional microscopy images with red, green and blue LED illuminations (20x objective, 0.5 N.A.). FIG. 14 (a4) is the color image constructed based on the red, green, and blue images in FIG. 14 (a1), FIG. 14(a2), and FIG. 14(a3). Since the sensor chip is not transparent, the conventional microscopy images were taken in reflection mode. The color in FIG. 14 (a4) is due to the light interference between the sensor surface and sample. The grid pattern in FIG. 14 (a1) to FIG. 14 (a4) is the pixel array of the image sensor (2.2 μm pixel size). FIG. 14 (b1), FIG. 14(b2), and FIG. 14(b3) are reconstructed sub-pixel resolution images of a portion of HeLa cell sample as acquired by an e-Petri system 600 under red, green, and blue light source scanning respectively, according to an embodiment of the invention. FIG. 14 (b4) is the reconstructed sub-pixel resolution color image based on the red, green, and blue images in FIG. 14 (b1), FIG. 14(b2), and FIG. 14(b3), according to an embodiment of the invention. The scale bar shown in each of the images in FIG. 14 is 20 μm.

C. Long-Term Cell Imaging and Tracking

The e-Petri system 600 of embodiments can be automated to image confluent cell samples with sub-cellular resolution over a large field-of-view at intervals of a study or other experiment. As such, it is well suited to long-term cell culture imaging and tracking applications.

To demonstrate these capabilities, an e-Petri-system 600 such as shown in FIGS. 11 and 12 was used to perform a longitudinal cell imaging and study. A customized program stored on the second CRM 220 was used by the second processor 210 of the host computer 200 to automatedly reconstruct and display the reconstructed image onto the display 230 for user monitoring. The customized program included information such as the time period of the experiment, the time intervals for automatedly reconstructing and displaying the images, and other suitable information.

The e-Petri system 600 had an e-Petri device 610 such as shown in FIGS. 12 and 13(c). A specimen 150 having HeLa cells was seeded onto a specimen surface 140 of an e-Petri-dish 620 of an e-Petri device 600 of an embodiment as shown in FIG. 13(c). The e-Petri device 610 was placed into an incubator 800 such as shown in FIG. 12 during the longitudinal cell imaging and study. An Ethernet cable connected the e-Petri device 610 to the host computer 200 in the form of a personal computer located the incubator 800 for data transfer, as shown in FIG. 12. In this experiment, an automated reconstruction and displaying imaging run was performed at 15 minute intervals during the entire growth duration of 48 hours. Each imaging run included a single illumination cycle. During the 48 hour time period of the study, the number of HeLa cells grew from 40+ to hundreds.

Figure 15:
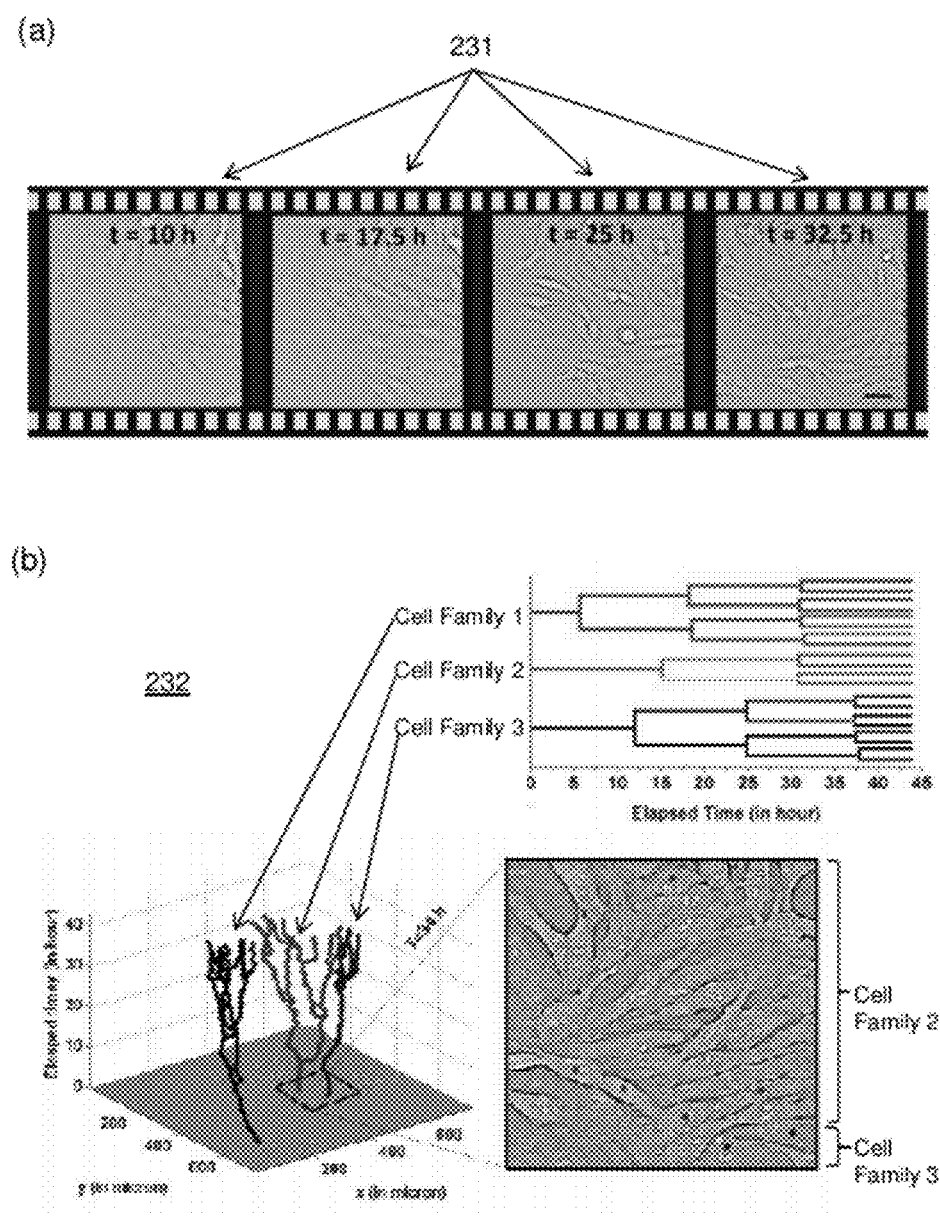
FIG. 15(a) are time-lapse reconstructed images of a portion of the HeLa cell sample from a specific sub-location, as acquired by an e-Petri system at starting at times, t=10 hr, t=17.5 hr, t=25 hr and t=32.5 hr during the time period of the study, according to an embodiment of the invention.
FIG. 15(b) are graphs of the tracking trajectories of three cell families annotated by a biologist and the lineage trees for these cell families that were processed by the second processor of the host computer of an e-Petri system, according to an embodiment of the invention.

FIG. 15(a) are time-lapse reconstructed images of a portion of the HeLa cell sample from a specific sub-location, as acquired by an e-Petri system 600 at starting at times, t=10 hr, t=17.5 hr, t=25 hr and t=32.5 hr during the time period of the study, according to an embodiment of the invention. Based on the time-lapse cell image data acquired by the e-Petri device 610, the e-Petri system 600 can detect and track each individual cell's movements in space and time, and generate corresponding lineage trees (i.e. mother-daughter relationship and otherwise analyze the data. FIG. 15(b) are graphs 232 of the tracking trajectories of three cell families annotated by a biologist and the lineage trees for these cell families that were processed by the second processor 210 of the host computer 200 of an e-Petri system 600, according to an embodiment of the invention.

D. Resolution

FIG. 8(a) is a example of a HR image of a specimen 150 having 500 nm microspheres (Polysciences) that may be acquired by an e-Petri system 600, according to an embodiment of the invention. The imaging process used to construct the image was identical the one used to reconstruct the images in FIG. 7. For a single 500 nm microsphere, the bright center of the microsphere was clearly resolved as shown in FIG. 8(a), with the full-width at half maximum (FWHM) of 690 nm. FIG. 8(b) is an example of a reconstructed image of a magnified small feature of the stained HeLa cell specimen 150 of FIG. 7 as acquired by an e-Petri system 600, according to an embodiment of the invention.

In some cases, microscopy resolution may be defined based on a given microscope's ability to resolve two closely spaced feature points. To establish resolution of an e-Petri system 600 of an embodiment based on this definition, two closely spaced microspheres were imaged by the e-Petri system 600. FIG. 8(a) shows the reconstructed images of two closely packed 500 nm microspheres with center-to-center distance of 660 nm, as acquired by the e-Petri system 600. The data trace in FIG. 8(a) shows a valley between the two peaks and, thus, establishes that the resolution may be 660 nm or better in some embodiments. To further verify this point, FIG. 8(b) shows the magnified small feature of the stained HeLa cell specimen of FIG. 7 and the FWHM of this feature was estimated to be about 710 nm. In one embodiment, the estimated resolution may be reduced if the specimen 150 is placed at a substantial distance above the sensor surface 160, such as described in Heng, X., et al, "*Characterization of light collection through subwavelength aperture from a point source,*" Optics express 14, pp. 10410-10425 (2006); and Wang, Y. M., Zheng, G., and Yang, C., "*Characterization of acceptance angles of small circular apertures,*" Optics Express 17, pp. 23903-23913 (2009), which are hereby incorporated by reference in their entirety for all purposes.

E. Additional Advantages

Embodiments of the invention provide one or more technical advantages. A general advantage of embodiments may be a lensless, sub-pixel resolution, wide field-of-view imaging device capable of imaging confluent cell culture with high resolution and incoherent light sources. Images acquired by embodiments may be closely comparable with those obtained with a conventional microscope. In an embodiment, an image with a resolution of 660 nm was acquired. The imaging method can be implemented on a smart e-Petri dish, which is capable of performing high resolution and autonomous imaging of cells plated on or growing on a low-cost CMOS sensor chip. The e-Petri dish of embodiments may be a useful tool for in-vitro long-term cell observations or other long term studies. To demonstrate that an e-Petri device 610 of an embodiment can be easily assembled, the e-Petri device was constructed out of blocks, a smartphone, and an imaging sensor chip.

An advantage of an e-Petri dish 620, e-Petri device 610, and e-Petri system 600 may be low cost. The e-Petri dish 620 can use a CMOS imaging sensor chip as the base substrate for cell culture growth. Post-experiment, the sensor chip can either be disposed or washed-and-reused. Given the low cost of these sensor chips, they are unlikely to represent a major cost component in most cell culture experiments.

Another of an e-Petri dish 620 may be that is can be disposable or recyclable. In certain biohazardous experiments, the ability to treat the sensor chips as disposable units would significantly reduce any associated risks.

Another advantage of an e-Petri system 600 may be that the host computer 200 outside the incubator 800 can display direct readout from the data acquired from inside the incubator 800. As shown in FIG. 12, the e-Petri device 610 of embodiments may be sufficiently compact to fit comfortably in a conventionally available incubator 800. In fact, given the footprint of the e-Petri device 600 of embodiments, it may be possible to fit multiple ePetri devices 610 into the same incubator 800, as shown in FIG. 11. Upon connecting the ePetri device 610 to an exterior processor 210 via an appropriate data cable, a user can start to collect images of the growing cell culture without removing the unit from the incubator 800. This advantage saves labor and cut down on the perturbations the cell culture is subjected to. In one embodiment, an e-Petri system 600 may include a compact and portable incubator 800 and ePetri device 610 combination that is suitable for point-of-care diagnostic and/or other uses.

Another advantage of an e-Petri system 600 may be the ability to continuously monitor a specimen 150 from the incubator 800. A user of an e-Petri system 600 may be able to monitor cell growth continuously. In bioscience research, this represents a good means for performing longitudinal studies. In medical applications, this can significantly cut down on the diagnostic time for medical procedures that requires culture growth based assessment. As an example, the ePetri dish 620 can replace the standard petri dish for tuberculosis, staph and other bacterial infection diagnosis. Whereas standard medical practice would start initiate a bacteria culture growth and then check the growth at relatively long time intervals (checking frequently would be too time consuming), a modified ePetri dish 620 may potentially be able to continuously and autonomously monitor for growth changes and notify the user to examine the sample when significant changes have been detected.

Another of an e-Petri dish 620 may be that it is a platform technology. Since the top surface of the light detector 160 in the form of a sensor chip may be unmodified in embodiments, a user is free to build upon it. It is very possible to simply use the ePetri as an imaging platform for a large number of sophisticated lab-on-a-chip designs, such as microorganisms detection based on the use of closed dielectrophoretic cages, microfluidics-based phenotyping imaging and screening of multicellular organisms, and high throughput malaria infected erythrocyte separation and imaging. An example of suitable closed dielectrophoretic cages can be found in Medoro, G. et al. "A lab-on-a-chip for cell detection and illumination," Optics letters 35, pp. 2188-2190 (2010), which is hereby incorporated by reference in its entirety for all purposes. An example of microfluidics-based phenotyping imaging and screening of multicellular organisms can be found in Crane, M., Chung, K., Stirman, J. & Lu, H., "Microfluidics-enabled phenotyping, imaging, and screening of multicellular organisms," Lab on a Chip 10, pp. 1509-1517 (2010), which is hereby incorporated by reference in its entirety for all purposes. An example of high throughput malaria infected erythrocyte separation and imaging can be found in Hou, H., et al., "Deformability based cell margination—A simple microfluidic design for malaria infected erythrocyte separation," Lab on a Chip 10, pp. 2605-2613 (2010), which is hereby incorporated by reference in its entirety for all purposes. It is also possible to modify the ePetri dish 620 to serve as a self-contained incubator and imaging unit. Also, to create a fluorescence imaging e-Petri dish 620, the light detector 160 may be coated with an appropriate filter material.

F. Flowchart

The e-Petri system 600 of embodiments can be automated to reconstruct and display sub-pixel resolution images 231 of a specimen 150 on an e-Petri dish 620 and other data 232 at intervals during an experiment for user monitoring. For example, a cell specimen 150 may be placed on an e-Petri dish 620 having a culture medium. The e-Petri dish 620 may then be placed into the support 180 of an e-Petri device 610 and the e-Petri device 610 with the e-Petri dish 620 may be placed in an incubator 180 for the duration of the experiment. The host computer 200 can receive a signal with data associated with the sub-pixel shifted projection images captured by the e-Petri dish 620 and reconstruct images 231 and other data 232 on the host computer at intervals during the experiment for user monitoring without having to remove the e-Petri device 610 from the incubator 800. The intervals may be at times $T=T_0, T_1 \ldots T_n$, where n can be any suitable integer (1, 2, 10, 100, etc.). $T_0$ refers to the initial time at the beginning of the experiment.

In some cases, a code may be used to automatedly reconstruct and display the images 231 and other data 232 at intervals. The code may be, for example, a customized program stored on the second CRM 220. The second processor 210 may use the code to automatedly reconstruct and display a sub-pixel resolution image on the display 230 for user monitoring. The customized program may include any suitable information regarding the imaging functions of the systems and the parameters. For example, the customized program may include the time intervals between illumination cycles, the time period of the experiment, the scanning pattern using during the illumination cycles, etc.

Figure 16:
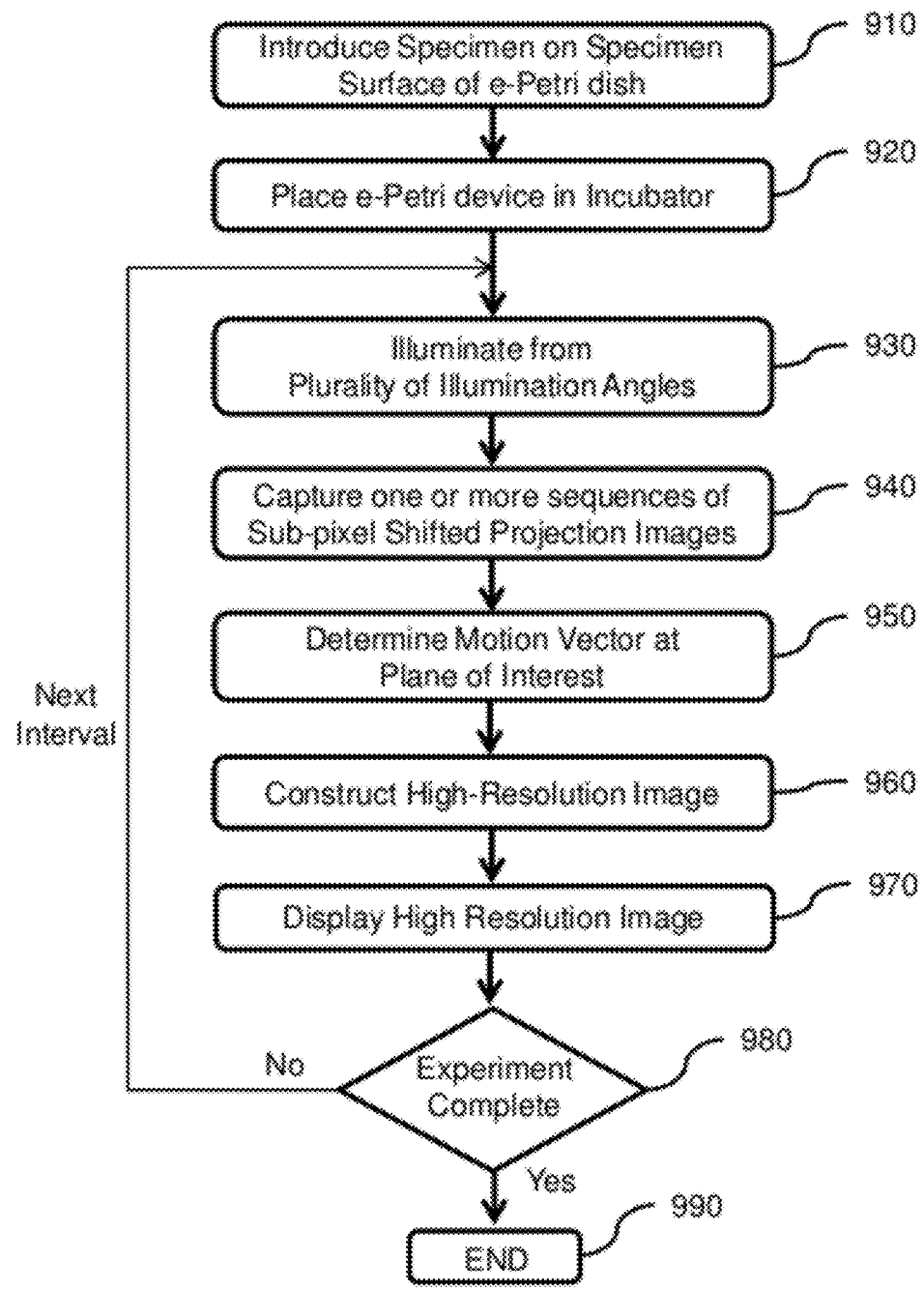
FIG. 16 is a flow chart of an exemplary method of automatedly reconstructing and displaying the sub-pixel resolution images and/or other data at intervals during an experiment by an e-Petri system, according to embodiments of the invention.

FIG. 16 is a flow chart of an exemplary method of automatedly reconstructing and displaying the sub-pixel resolution images 231 and other data 232 at intervals during an experiment by an e-Petri system 600, according to embodiments of the invention. In step 910, a specimen 150 is placed onto the specimen surface 140 of the e-Petri dish 620. If the e-Petri dish includes a well 170 with a peripheral wall 172, the specimen 150 is placed within the peripheral wall 172 of the well 170 on the specimen surface 140. The e-Petri dish 620 may also have a culture medium or other material located on the specimen surface 140 of the e-Petri dish 620. Once the specimen 150 is introduced, the e-Petri dish 620 is then placed in the e-Petri device 600. For example, the e-Petri dish 620 may be placed in a receiving portion of the support 180 of the e-Petri device 610.

In step 920, the e-Petri device 610 is located within an incubator 800 providing a pre-defined environment. The e-Petri device 610 can remain within the incubator 800 during the duration of the experiment, which may reduce contamination risks. Once in the incubator, the e-Petri system 600 can automatedly image the specimen 150 at time intervals $T=T_0, T_1 \ldots T_n$, where n can be any suitable integer (1, 2, 10, 100, etc.). $T_0$ refers to the initial time at the beginning of the experiment. The time intervals can be on a periodic basis such as every 15 minutes. The experiment may have any suitable duration. The e-Petri system 600 may also generate other data 232 associated with the data gathered by the e-Petri dish 620. For example, various graphs of the growth of different cell lineages may be generated and displayed at each interval. The e-Petri system 600 may use a code stored on the CRM 220 or other suitable memory. The code include processing instructions that are automated during the experiment. For example, the code may included instructions on reconstructing and displaying images 231 and other data 232 at intervals. The code may also include instructions regarding the illumination cycle at each interval and other instructions regarding functions of the e-Petri system 600.

In step 930, the specimen 150 is illuminated from a plurality of illumination angles at different times during an interval of the experiment. The e-Petri device 610 includes a scanning illumination source 110 at a distance, d, from the sensing surface 162 that provides light 118 from the plurality of illumination angles to the specimen 150 on the specimen surface 142. Light 180 from the plurality of illumination angles generates one or more sequences of sub-pixel shifted projection images on the sensing surface 162 of the light detector 160 of the e-Petri dish 620.

In one embodiment, the illumination source 110 may have an illuminating display 116 with a light element 117 providing the illumination 118 from different angles at different times during an illumination cycle during the interval of the experiment. The light element 117 is positioned at different positions at different times to provide the illumination 118 from the different angles. For example, the light element 117 may be different sets of illuminated light emitting elements of the illuminating display 116 at different times during the experiment. The illumination 118 can vary at different positions. For example, the light element 117 can provide illumination 118 of n different wavelengths $\lambda_1, \ldots, \lambda_n$ at different times during each illumination cycle to obtain a sequence of projection images for each wavelength. Any suitable number of wavelengths may be used (e.g., n=1, 2, 3, 4, 5, . . . , 20). In one embodiment, the light element 117 may provide illumination 118 of three wavelengths $\lambda_1, \lambda_{23}$, and $\lambda_3$ corresponding to red, green, blue colors at different sampling times. In some cases, the illumination 118 from one scanning location to a neighboring scanning location may have different wavelengths. In other cases, the illumination 118 may have a first wavelength during a first series of scanning positions, and then provide illumination 118 of a second wavelength during a second series of scanning positions, and so forth until n sequences of projection images corresponding to n different wavelengths have been captured. In some cases, the first processor 112 of the illumination source 110 may determine a scanning pattern having the different positions at the different times, properties (e.g., wavelength(s) of light used, the size and shape of the light element 117, the intensity(ies) of the light element, etc.) of the light element 117 at different scanning positions, the amount of sub-pixel shift desired in a sequence, the duration of the experiment, the interval time(s), descriptions of other data that may be displayed during each interval, and other suitable information related to the operation of the e-Petri system 600. The scanning pattern may be stored as code on the first CRM 114 or other suitable memory.

In step 940, the light detector 160 captures one or more sequences of sub-pixel shifted projection images of the specimen 150 during each illumination cycle of each interval during the experiment. The light detector 160 may capture a projection image at each illumination angle.

In step 950, the processor 230 uses a suitable method to determine the motion vector of the one or more sequences of sub-pixel shifted projection images captured during the interval of the experiment. The motion vector is determined based on a plane of interest such as the sensing surface 162 or plane through the specimen 150. Any suitable method of determining a motion vector can be used.

In step 960, the processor 210 uses an appropriate SR algorithm to construct one or more sub-pixel images of the specimen from the one or more sequences of sub-pixel shifted projection images and the determined motion vector during the interval of the experiment. The one or more sub-pixel resolution images are located (focused) at the plane of interest used to determine the motion vector. Depending on the scheme, the sub-pixel resolution images can be 2D monochromatic images, 2D color images, 3D monochromatic or color images. The processor 210 may also generate other data images 232 (e.g., lineage trees) based on data gathered during the interval.

In step 970, the processor 210 can display the one or more sub-pixel resolution images 231 to a display 230 during the interval of the experiment. In addition, other data 232 can be displayed.

In step 980, the processor 210 determines whether the experiment is complete. In some cases, the processor 210 determines whether the experiment is complete by determining the current time is at the end of the duration of the experiment. In other cases, the user of the e-Petri system 600 may provide input that determines that the experiment is complete. For example, the user may enter a stop experiment command at the host computer 200. If the experiment is not complete, the next interval of the experiment begins and the process goes to step 930. If the experiment is complete, the process ends at step 990.

IV. Subsystems

Figure 17:
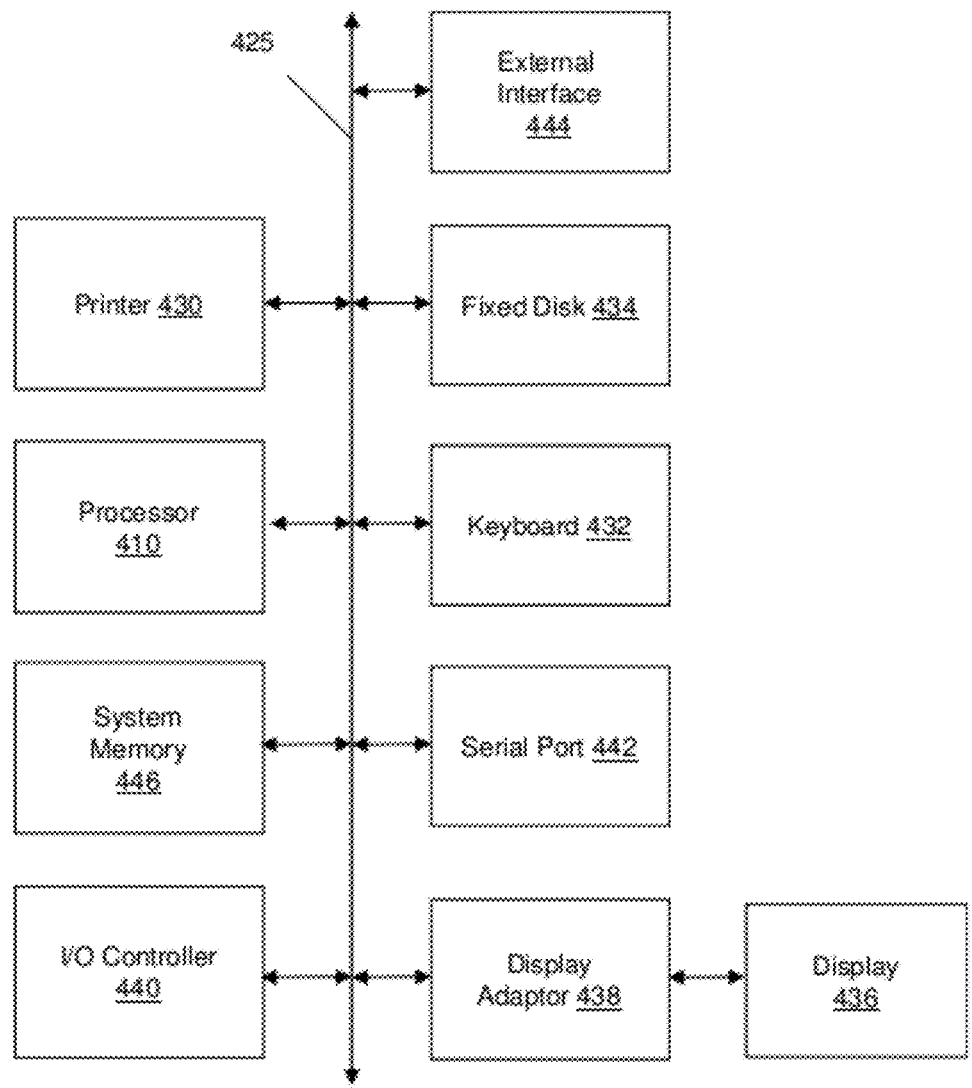
FIG. 17 is a block diagram of subsystems that may be present in the SPLM system or an e-Petri system, according to embodiments of the invention.

FIG. 17 is a block diagram of subsystems that may be present in the SPLM system 10 or in an e-Petri system 600, according to embodiments of the invention. For example, the SPLM system 10 and the e-Petri system 600 include a processor 410. The processor 410 may include first processor 112 and/or second processor 210. The processor 410 may be a component of the light detector 160 in some cases. The processor 410 may be a component of the illumination source 100 in some cases.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 17. The subsystems shown in FIG. 17 are interconnected via a system bus 425. Additional subsystems such as a printer 430, keyboard 432, fixed disk 434 (or other memory comprising computer readable media), display 436, which is coupled to display adapter 438, and others are shown. The display 436 may include the illuminating display 116 and/or the image display 230. Peripherals and input/output (I/O) devices, which couple to I/O controller 440, can be connected to the computer system by any number of means known in the art, such as serial port 442. For example, serial port 442 or external interface 444 can be used to connect the computer apparatus to a wide area network such as the Internet, a mouse input device, or a scanner. The interconnection via system bus allows the processor 410 to communicate with each subsystem and to control the execution of instructions from system memory 446 or the fixed disk 434, as well as the exchange of information between subsystems. The system memory 446 and/or the fixed disk 434 may embody a first CRM 114 and/or a second CRM 220. Any of these elements may be present in the previously described features.

In some embodiments, an output device such as the printer 430 or display 436 of the SPLM system 10 or the e-Petri system 600 can output various forms of data. For example, the SPLM system 10 or the e-Petri system 600 can output 2D/3D HR color/monochromatic images, data associated with these images, or other data associated with analyses performed by the SPLM system 10 or the e-Petri system 600.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. An e-Petri dish comprising:
   a light detector;
   a transparent layer disposed on the light detector and having a specimen surface; and
   a processor,
   wherein the light detector is configured to sample a sequence of sub-pixel shifted projection images of a specimen when the specimen is located on the specimen surface and while light incident the specimen from an illumination source is shifted through a plurality of illumination angles, wherein the illumination source comprises sets of light emitting components at different locations, the sets of light emitting components configured to sequentially illuminate to generate the light from the plurality of illumination angles,
   wherein each sub-pixel shifted projection image is sampled at a different sampling time while the illumination source provides light from one of the illumination angles, and
   wherein each sub-pixel shifted projection image is associated with light passing through the specimen, and
   wherein the processor is configured to generate a sub-pixel resolution image of the specimen using image data from the sequence of sub-pixel shifted projection images of the specimen and a motion vector, wherein the processor is further configured to determine the motion vector, the motion vector associated with a plane of interest and the sub-pixel resolution image is focused at the plane of interest.

2. The e-Petri dish of claim 1, further comprising a well coupled to the transparent layer, the well configured to contain the specimen.

3. The e-Petri dish of claim 1, wherein there is no lens in the illumination path between the illumination source and the light detector.

4. The e-Petri dish of claim 1, wherein the illumination source is a coherent light source.

5. The e-Petri dish of claim 1, wherein the light detector and the illumination source are on opposing sides of the specimen surface.

6. The e-Petri dish of claim 1, wherein the illumination angles range from −60 degree to +60 degrees with respect to the sensing surface.

7. The e-Petri dish of claim 1, wherein the transparent layer has a thickness in a range of several hundred nanometers to microns.

8. The e-Petri dish of claim 1, wherein each of the sets of light emitting components is a set of one or more pixels of a display.

9. The e-Petri dish of claim 8, wherein the display is a liquid crystal display or a light emitting diode display.

10. The e-Petri dish of claim 1, wherein each of the sets of light emitting components is a set of one or more pixels of a smartphone screen.

11. The e-Petri dish of claim 1, wherein the light detector is an image sensor.

12. The e-Petri dish of claim 1, wherein the light detector and the transparent layer are in the form of a CMOS image sensor comprising a PDMS layer disposed on a sensing surface.

13. An e-Petri device comprising:
    a light detector;
    a transparent layer disposed on the light detector and having a specimen surface;
    an illumination source comprising sets of light emitting components at different locations, the sets of light emitting components configured to provide light from a plurality of illumination angles to a specimen located on the specimen surface; and
    a processor,
    wherein the light detector is configured to sample a sequence of sub-pixel shifted projection images of the specimen when the specimen is located on the specimen surface and while light incident the specimen from the illumination source is shifted through the plurality of illumination angles, wherein each of the sub-pixel shifted projection images is sampled at a different sampling time while the illumination source provides light from one of the illumination angles, wherein each sub-pixel shifted projection image is associated with light passing through the specimen, and wherein the sequence of sub-pixel shifted projection images is sampled at different sampling times corresponds to the plurality of illumination angles, wherein the processor is configured to generate a sub-pixel resolution image of the specimen based on the sequence of sub-pixel shifted projection images of the specimen and a motion vector based on the sequence of sub-pixel shifted projection images, and wherein the processor is further configured to determine the motion vector, the motion vector associated with a plane of interest wherein the sub-pixel resolution image is focused at the plane of interest.

14. The e-Petri device of claim 13, wherein the sets of light emitting components provide light of different light intensities at different locations.

15. The e-Petri device of claim 13, wherein the sets of light emitting components provide light of a plurality of wavelengths at different locations;

wherein the sequence of sub-pixel shifted projection images comprises a plurality subsequences of sub-pixel shifted projection images associated with the plurality of wavelengths; and wherein the processor is further configured to generate a plurality of sub-pixel resolution images associated with the plurality of wavelengths and configured to combine the plurality of sub-pixel resolution images associated with the plurality of wavelengths to generate a multi-color sub-pixel resolution image of the specimen.

16. The e-Petri device of claim 13, further comprising a well defining by a peripheral wall coupled to the specimen surface.

17. The e-Petri device of claim 16, further comprising a cover located over the well.

18. The e-Petri device of claim 16, wherein the well includes an array of chambers.

19. The e-Petri device of claim 13, further comprising a dielectric cage.

20. The e-Petri device of claim 13, further comprising a fluid channel.

21. The e-Petri device of claim 13, wherein the light detector includes the processor.

22. The e-Petri device of claim 13, wherein each of the sets of light emitting components is a set of one or more pixels of a display.

23. The e-Petri device of claim 13, wherein each of the sets of light emitting components is a set of one or more pixels of a smartphone screen.

24. The e-Petri device of claim 13, wherein the light detector is an image sensor.

25. The e-Petri device of claim 13, wherein the light detector and the transparent layer are in the form of a CMOS image sensor comprising a PDMS layer disposed on a sensing surface.

26. An e-Petri system comprising:

one or more e-Petri devices, each e-Petri device comprising a light detector;

a transparent layer disposed on the light detector and having a specimen surface;

an illumination source comprises sets of light emitting components at different locations, the sets of light emitting components configured to sequentially shift illumination through a plurality of illumination angles to a specimen located on the specimen surface; and wherein the light detector is configured to sample a sequence of sub-pixel shifted projection images of the specimen when the specimen is located on the specimen surface and while light incident the specimen from the illumination source is shifted through the plurality of illumination angles, wherein each of sub-pixel shifted projection images is sampled at a different sample time while the illumination source provides light from one of the illumination angles, and wherein each sub-pixel shifted projection image is associated with light passing through the specimen; and a processor configured to generate a sub-pixel resolution image of the specimen based on the sequence of sub-pixel shifted projection images from at least one of the one or more e-Petri devices and a motion vector based on the sequence of sub-pixel shifted projection images, wherein the processor is further configured to determine the motion factor, wherein the motion is associated with a plane of interest and the sub-pixel resolution image is focused at the plane of interest.

27. The e-Petri system of claim 26, further comprising a relay in communication with the processor to receive data from the one or more e-Petri devices; and further comprising a host computer in communication with the relay to receive data from the one or more e-Petri devices.

28. The e-Petri system of claim 26, wherein the sets of light emitting components provide light of different light intensities at different locations.

29. The e-Petri system of claim 26, wherein the sets of light emitting components provide light of a plurality of wavelengths at different locations;

wherein the sequence of sub-pixel shifted projection images comprises a plurality subsequences of sub-pixel shifted projection images associated with the plurality of wavelengths; and wherein the processor is further configured to generate a plurality of sub-pixel resolution images associated with the plurality of wavelengths and configured to combine the plurality of sub-pixel resolution images associated with the plurality of wavelengths to generate a multi-color sub-pixel resolution image of the specimen.

30. The e-Petri system of claim 26, further comprising an incubator configured to maintain a pre-defined environment, the one or more e-Petri devices located within the incubator.

31. The e-Petri system of claim 26, wherein each e-Petri device further comprises a support holding the illumination source with respect to the specimen surface.

32. A method of automatedly generating a sub-pixel resolution image of a specimen using an e-Petri system at intervals during an experiment, the method comprising:

introducing the specimen on a specimen surface of a transparent layer disposed over a light detector of an e-Petri dish;

during each interval, using an illumination source to shift light incident the specimen through a plurality of illumination angles, wherein the sequentially illuminating different sets of light emitting components of an illuminating display;

during each interval, using the light detector to sample a sequence of sub-pixel shifted projection images corresponding to the plurality of illumination angles, wherein each of the sub-pixel shifted projection images is sampled at a different sampling time while the illumination source provides light from one of the illumination angles and wherein each sub-pixel shifted projection image is associated with light passing through the specimen; and during each interval, constructing a sub-pixel resolution image of the specimen based on the sequence of sub-pixel shifted projection images and a motion vector; and focusing the sub-pixel resolution image at a plane of interest by determining the motion vector based on the plane of interest.

33. The method of claim 32, further comprising during each interval, displaying the sub-pixel resolution image of the specimen.

34. The method of claim 32, wherein providing light from a plurality of illumination angles comprises sequentially illuminating different sets of light emitting components of an illuminating display.

35. The method of claim 32, wherein each of the sets of light emitting components is a set of one or more pixels of a display.

36. The method of claim 32, wherein each of the sets of light emitting components is a set of one or more pixels of a smartphone screen.

37. The method of claim 32, wherein the light detector is an image sensor.

38. An e-Petri dish comprising:
an image sensor chip;
a transparent well disposed on the image sensor chip; and
a processor,
wherein the image sensor chip is configured to sample a sequence of sub-pixel shifted projection images of a specimen when the specimen is located in the transparent well and while light from an illumination source is shifted through a plurality of illumination angles, wherein the illumination source comprises sets of light emitting components at different locations, the sets of light emitting components configured to sequentially illuminate to generate the light from the plurality of illumination angles, wherein each sub-pixel shifted projection image is sampled at a different sampling time while the illumination source provides light from one of the illumination angles, and wherein each sub-pixel shifted projection image is a measurement of light from the illumination source transmitted through the specimen, and wherein the processor is configured to generate a sub-pixel resolution image of the specimen using image data from the sequence of sub-pixel shifted projection images of the specimen and a motion vector, wherein the processor is further configured to determine the motion vector, the motion vector associated with a plane of interest and the sub-pixel resolution image is focused at the plane of interest.

39. The e-Petri dish of claim 38, wherein each of the sets of light emitting components is a set of one or more pixels of a display.

40. The e-Petri dish of claim 38, wherein each of the sets of light emitting components is a set of one or more pixels of a smartphone screen.

* * * * *